(12) United States Patent
Buchwald et al.

(10) Patent No.: US 7,687,272 B1
(45) Date of Patent: *Mar. 30, 2010

(54) METHOD AND APPARATUS FOR DETERMINING BLOOD OXYGEN TRANSPORT

(76) Inventors: Henry Buchwald, 6808 Margaret's La., Edina, MN (US) 55439; Hector J. Menchaca, 13834 Essex Trail, Apple Valley, MN (US) 55124; Van N. Michalek, 2839 Aglen Ave. North, Roseville, MN (US) 55113; Thomas J. O'Dea, 925 Arbogast St., Shoreview, MN (US) 55120; Thomas D. Rohde, 702 Third Ave., SE., Minneapolis, MN (US) 55414

( * ) Notice: Subject to any disclaimer, the term of this patent is extended or adjusted under 35 U.S.C. 154(b) by 1661 days.

This patent is subject to a terminal disclaimer.

(21) Appl. No.: 09/645,236

(22) Filed: Aug. 24, 2000

Related U.S. Application Data

(63) Continuation-in-part of application No. 09/600,094, filed as application No. PCT/US99/00613 on Jan. 12, 1999, now Pat. No. 6,806,091, and a continuation-in-part of application No. 09/005,474, filed on Jan. 12, 1998, now Pat. No. 6,037,181.

(51) Int. Cl.
*G01N 33/00* (2006.01)
*G01N 33/50* (2006.01)

(52) U.S. Cl. .......................... 436/71; 422/68.1; 422/73; 422/82.05; 422/82.09; 422/83; 436/63; 436/66; 436/68; 436/127; 436/136; 436/138; 436/164; 436/167; 436/168; 436/172; 436/181; 435/2

(58) Field of Classification Search .................. 436/63, 436/66, 68, 71, 127, 136, 138, 164, 167, 436/168, 172, 181; 422/68.1, 73, 82.05, 422/82.08, 82.09, 83, 88, 99; 435/2
See application file for complete search history.

(56) References Cited

U.S. PATENT DOCUMENTS

| | | | |
|---|---|---|---|
| 3,647,299 | A | 3/1972 | Lavallee |
| 3,779,708 | A | 12/1973 | Runck et al. |
| 4,013,417 | A | 3/1977 | Raffaele |
| 4,120,658 | A | 10/1978 | Bruttig |
| 4,133,874 | A | 1/1979 | Miller et al. |

(Continued)

FOREIGN PATENT DOCUMENTS

EP 0 240 742 A2 10/1987

(Continued)

OTHER PUBLICATIONS

Anderson, H.V., et al., "Coronary artery flow monitoring following coronary interventions," *European Heart Journal*, (Supplement J) 16:71-73 (1995).

(Continued)

*Primary Examiner*—Maureen M Wallenhorst
(74) *Attorney, Agent, or Firm*—Brian R. Dorn; Merchant & Gould

(57) ABSTRACT

The present invention relates to a method and apparatus for determining blood oxygen transport, and to measure lipid levels by correlating these levels with the rate at which oxygen diffuses through the red blood cell membrane.

25 Claims, 19 Drawing Sheets

U.S. PATENT DOCUMENTS

| | | | |
|---|---|---|---|
| 4,209,300 | A | 6/1980 | Thibault |
| 4,880,304 | A * | 11/1989 | Jaeb et al. ..................... 356/41 |
| 5,604,105 | A | 2/1997 | Jackowski |
| 5,686,300 | A | 11/1997 | Berndt |
| 6,388,247 | B2 * | 5/2002 | Asada et al. ................ 250/221 |

FOREIGN PATENT DOCUMENTS

| | | |
|---|---|---|
| JP | 01088340 | 4/1989 |
| RU | 2073485 | 2/1997 |
| SU | 1739295 | 6/1992 |
| WO | WO96/03655 | 2/1996 |
| WO | WO99/21002 | 4/1999 |

OTHER PUBLICATIONS

Clark, Jr., A. et al. "Oxygen Delivery From Red Cells," *Biophysical Journal*, 47:171-181 (Feb. 1985).

Di Mario, C. et al., "Principles of interpretation of coronary velocity and pressure tracings," *European Heart Journal*, (*Supplement J*), 16:53-59 (1995).

Guyton, A.C., *Textbook of Medical Physiology* —eighth edition; sections on coronary blood flow; diffusion; oxygen capacity of blood, pp. 186, 237, 43-44; 434-439 (WB Saunders, Philadephia, Pa. 1991).

Huxley, V. H., et al., "Effect of Diffusion Boundary Layers on the Initial Uptake of $O_2$ by Red Cells. Theory versus Experiment," *Microvascular Research*, 26:89-107 (1983).

Mendelson, Y. et al., "In-vitro Evaluation of a Dual Oxygen Saturation/Hematocrit Intravascular Fiberoptic Catheter," *Biomedical Instrumentation & Technology*, 24:199-206 (May/Jun. 1990).

Page, T.C. et al., "Chapter 9—Experimental Simulation of Oxygen Transport in Microvessels," pp. 132-145 1996.

Page, T. C. et al., "Oxygen Transport by Erythrocyte/Hemoglobin Solution Mixtures in an in Vitro Capillary as a Model of Hemoglobin-Based Oxygen Carrier Performance," *Microvascular Research*, 55:54-64 (1998).

Popel, A.S., "Theory of Oxygen Transport to Tissue," *Critical Reviews in Biomedical Engineering*, 17(3):257-321 (1989).

Steinbach, J. H. et al., "High Blood Cholesterol Reduces in Vitro Blood Oxygen Delivery," *Journal of Surgical Research*, 16:134-139 (1974).

Tsai, A. G. et al., "Chapter 8—Microvascular Oxygen Distribution: Effects Due to Free Hemoglobin in Plasma," pp. 124-131 (undated).

Villars, F.M. et al., *Physics with Illustrative Examples from Medicine and Biology*, vol. 2. Statistical Physics; sections on the diffusion equation; Particle Conservation and Fick's Law; Transport of Water and Solute Across Biological Membranes, pp. 2-46 to 2-47; 2-66 to 2-79; 2-81 to 2-83; 2-92 to 2-97; 2-106; 2-192 to 2-203 (Addison-Wesley, Reading, Mass., 1974).

Stathopoulos, N. et al., "Oxygen Transport Studies of Normal and Sickle Red Cell Suspensions in Artificial Capillaries", *Microvascular Research*, vol. 34, 1 pg., Abstract only (Sep. 1987).

Weatherall, D. et al., "Red Cells I: Inherited Anaemias", *The Lancer*, vol. 355, pp. 1169-1175 (Apr. 1, 2000).

Koyama, T. et al., "Difffusion Pathway of Oxygen in Ox Lung." *Advances in Experimental Medicine and Biology*, 222: 63-68 (1988).

Kon, K. et al., "A Method for Studying Oxygen Diffusion Barrier in Erythrocytes: Effects of Haemoglobin Content and Membrane Cholesterol," *The Journal of Physiology*, 309: 569-590 (1980).

* cited by examiner

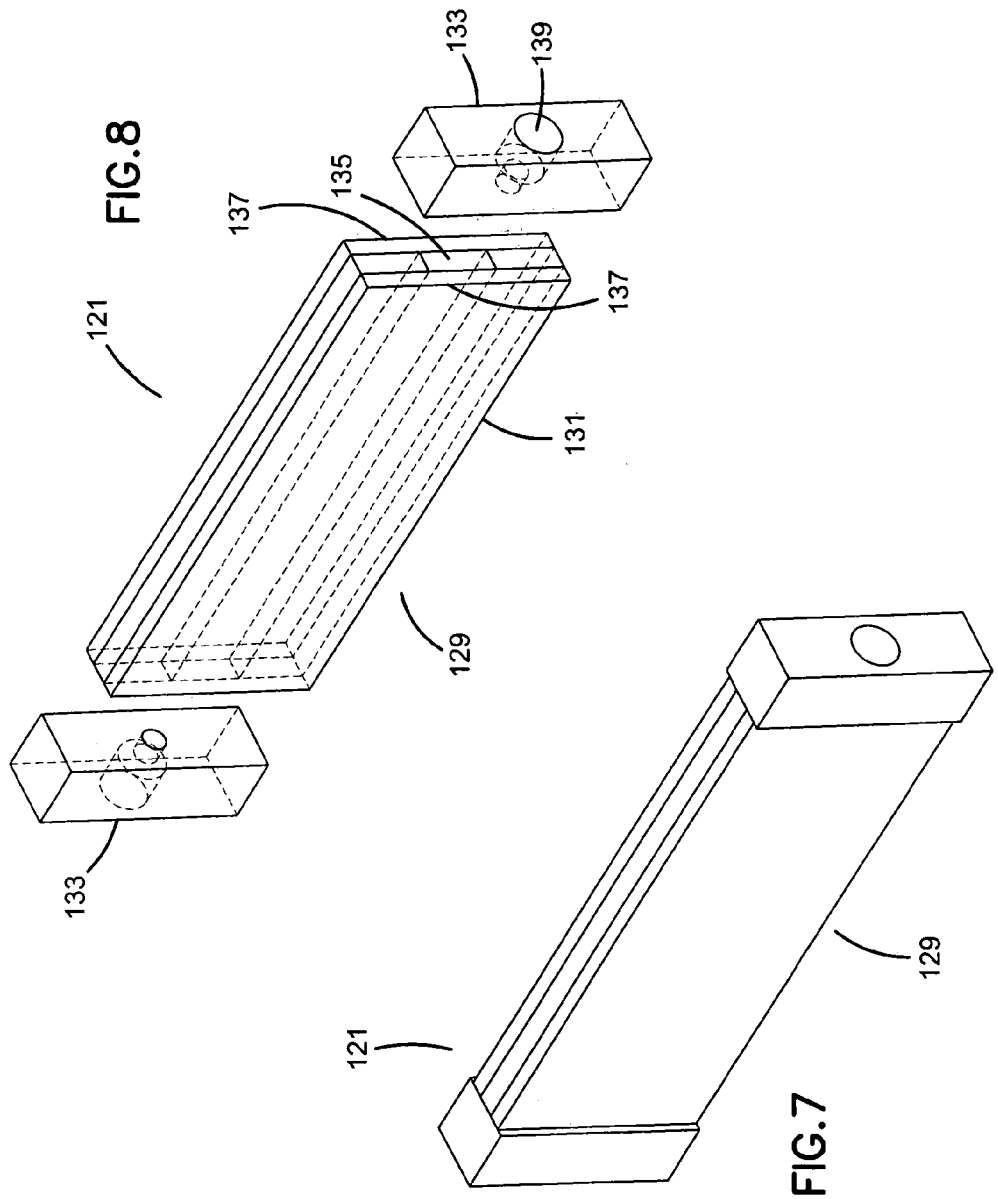

Sensor, pump and environmental control sequence

METHOD AND APPARATUS FOR DETERMINING BLOOD OXYGEN TRANSPORT

CROSS REFERENCE TO RELATED APPLICATION

The present application is a continuation in part of U.S. patent application Ser. No. 09/600,094, now U.S. Pat. No. 6,806,091, issued on Oct. 19, 2004 which is a national stage filing from international application no. PCT/US99/00613 filed Jan. 12, 1999 and a continuation in part of U.S. patent application Ser. No. 09/005,474 filed Jan. 12, 1998 now U.S. Pat. No. 6,037,181 issued on Mar. 14, 2000.

BACKGROUND OF THE INVENTION

The relationship between elevated blood lipids, particularly cholesterol (and especially low-density-lipoprotein cholesterol) and atherosclerosis has been known for many years. More recently, reduction of LDL cholesterol by means of surgery or drugs has been shown to reduce the risk of coronary heart disease. However, the reduction of cardiac events achieved by cholesterol lowering does not correlate well with the relatively small amount of physical regression in the amount of atherosclerotic plaque seen in the coronary arteries following treatment. In addition, relief of angina pectoris (ischemic chest pain) often occurs in a matter of weeks following cholesterol lowering; whereas, documentable changes in the inside diameters of coronary arteries may take years to occur, if they occur at all. The pain associated with angina pectoris is attributable primarily to lactic acid produced when heart muscle cell metabolism occurs in the absence of oxygen. Coronary artery narrowing can limit the amount of blood-transported oxygen that reaches the heart muscle tissue, but, the above observation suggests oxygenation of heart muscle tissue can be improved without increasing blood flow through the coronary vessels.

The way in which changes in blood lipids, such as cholesterol, might affect oxygen delivery to heart muscle tissue has remained unclear. There is abundant oxygen in blood. In fact, oxygenated (arterial) blood contains approximately as many molecules of oxygen per 1000 mL as are found in 200 mL of oxygen gas. Almost all (98–99%) of this oxygen is bound to hemoglobin molecules within the red blood cells; the remainder is physically dissolved in plasma and intracellular red blood cell fluid. For oxygen to reach tissues, such as cardiac muscle tissue, oxygen must be released from hemoglobin and then diffuse across the red blood cell membrane into the plasma and from there into tissues. The movement of oxygen across the red blood cell membrane occurs by passive diffusion and is governed by concentration gradients; there is no active membrane transport system for oxygen. Furthermore, the composition of a subject's red blood cell membrane changes with changes in the subject's lipid status. Therefore, the red blood cell membrane, the immediate surroundings of the red blood cell (the boundary layer), or the contours of the red blood cell membrane can be a significant barrier to release of oxygen into tissue such as cardiac muscle tissue.

What is needed is a method and apparatus to measure the rate at which oxygen diffuses through a red blood cell membrane and to employ measurements of this rate for diagnosing or aiding treatment of diseases and disorders.

SUMMARY OF THE INVENTION

The present invention relates to an apparatus and method for determining the rate at which oxygen crosses the red blood cell membrane. The present method and apparatus can aid in the diagnosis, treatment, and study of diseases and disorders that affect oxygen release or uptake. The apparatus and method provide a way to assess diseases or disorders of the heart, lung, or circulation; disease or disorder of endothelial function; a disease or disorder of the release of transmitters; and other diseases or disorders related to oxygen transport. Advantageously, the apparatus and method of the invention can be used to assess a patient's susceptibility to, or the frequency and severity of, disorders or diseases of blood oxygen transport, such as angina pectoris and chronic obstructive pulmonary disease. The method also includes embodiments directed to methods of evaluating lipid-lowering treatments, methods of diagnosing or assessing the risk of heart and circulatory disorders such as angina pectoris, and the like.

The present method measures a rate or rates of oxygen diffusion across a red blood cell membrane from the patient. Advantageously, red blood cell samples are standardized to generally uniform conditions of gas content by exposing the red blood cell to oxygen and exposing the red blood cell to an environment depleted of oxygen as part of the measurement process. Preferably, the rate at which oxygen moves across the red blood cell membrane or its boundary layer is determined by monitoring either a blood plasma level of oxygen, a level of oxygen bound to hemoglobin, or both.

The present method of determining a patient's blood lipid level, and its impact, includes measuring a rate or rates of oxygen diffusion across a red blood cell membrane from the patient. The rate indicates the blood lipid level, for example, through correlating a measured rate with a previously determined rate or range of rates for an established level of blood lipid. Advantageously, red blood cell samples are standardized to generally uniform conditions of gas content by exposing the red blood cell to oxygen and exposing the red blood cell to an environment depleted of oxygen as part of the measurement process. Preferably, the rate at which oxygen moves across the red blood cell membrane is determined by monitoring either a blood plasma level of oxygen, a level of oxygen bound to hemoglobin, or both.

In one embodiment, the method of the invention can be used to assess a patient's susceptibility to, or the frequency or severity of, a disease or disorder of blood oxygen transport, such as angina pectoris or chronic obstructive pulmonary disease. This embodiment includes measuring a rate of oxygen diffusion across a membrane of a red blood cell from the patient. This rate indicates the patient's susceptibility to the disease or disorder of blood oxygen transport, for example, by correlating the measured rate with the susceptibility to the disease or disorder of blood oxygen transport observed in a control or standardized population, or in the patient, at the measured rate.

In another embodiment, the method of the invention can be used to follow the course of a therapy for a disease or disorder of blood oxygen transport, such as a lipid-lowering therapy. This embodiment includes measuring a rate of oxygen diffusion across a membrane of a red blood cell from the patient. This rate determines the effectiveness of a therapy for a disease or disorder of blood oxygen transport, for example, by correlating the measured rate with the presence or severity of therapy for a disease or disorder of blood oxygen transport, and comparing this to the patient's previous degree of the disease or disorder of blood oxygen transport.

The apparatus of the invention, which is suitable for conducting the methods of the invention, measures diffusion of oxygen across a red blood cell membrane and includes an oxygen level detector, a gas exchange system, and a red blood cell transport system. The red blood cell transport system is adapted and configured for transporting red blood cells through the gas exchange system and the oxygen level detector. The gas exchange system is adapted and configured to exchange gasses with the red blood cell. The oxygen level detector is adapted and configured for detecting oxygen levels in a red blood cell or in fluid (e.g., plasma) surrounding a red blood cell.

In a preferred embodiment, the apparatus of the invention includes a modular transport system. Preferably, the modular transport system includes a sampling apparatus, a pump, a diffusion apparatus, and a transparent optical system. The modular transport system is adapted and configured for reversibly coupling to a main body of the apparatus. The sampling apparatus is adapted and configured for introducing a fluid containing red blood cells into the red blood cell transport system. The pump is adapted and configured for moving a fluid containing red blood cells into the red blood cell transport system, and through the diffusion apparatus and the transparent optical system. The diffusion apparatus is adapted and configured for providing contact between a gas and a red blood cell. The transparent optical system is adapted and configured for providing a generally transparent pathway for light to access the fluid containing red blood cells.

In a preferred embodiment, the main body of the apparatus includes a gas inlet, a gas outlet, a pump motor, a measuring system, and a control system. The main body can also define a portion of a chamber or environmental chamber. In this embodiment, the gas exchange system includes the gas inlet, gas outlet, a main body portion of the environmental chamber, and the diffusion system. The gas inlet, gas outlet, and the main body portion of the environmental chamber are adapted and configured for coupling and cooperating with the diffusion system. The red blood cell transport system includes the pump and pump motor. The pump motor is adapted and configured for coupling to and driving the pump. The oxygen level detector includes the measuring system and the transparent optical system. The measuring system is adapted and configured for directing light upon the transparent optical system.

BRIEF DESCRIPTION OF THE DRAWINGS

FIG. 7 illustrates a cuvette.

FIG. 8 illustrates an exploded view of the cuvette of FIG. 7 showing the cuvette body and the fittings.

DETAILED DESCRIPTION OF THE INVENTION

Figure 1:
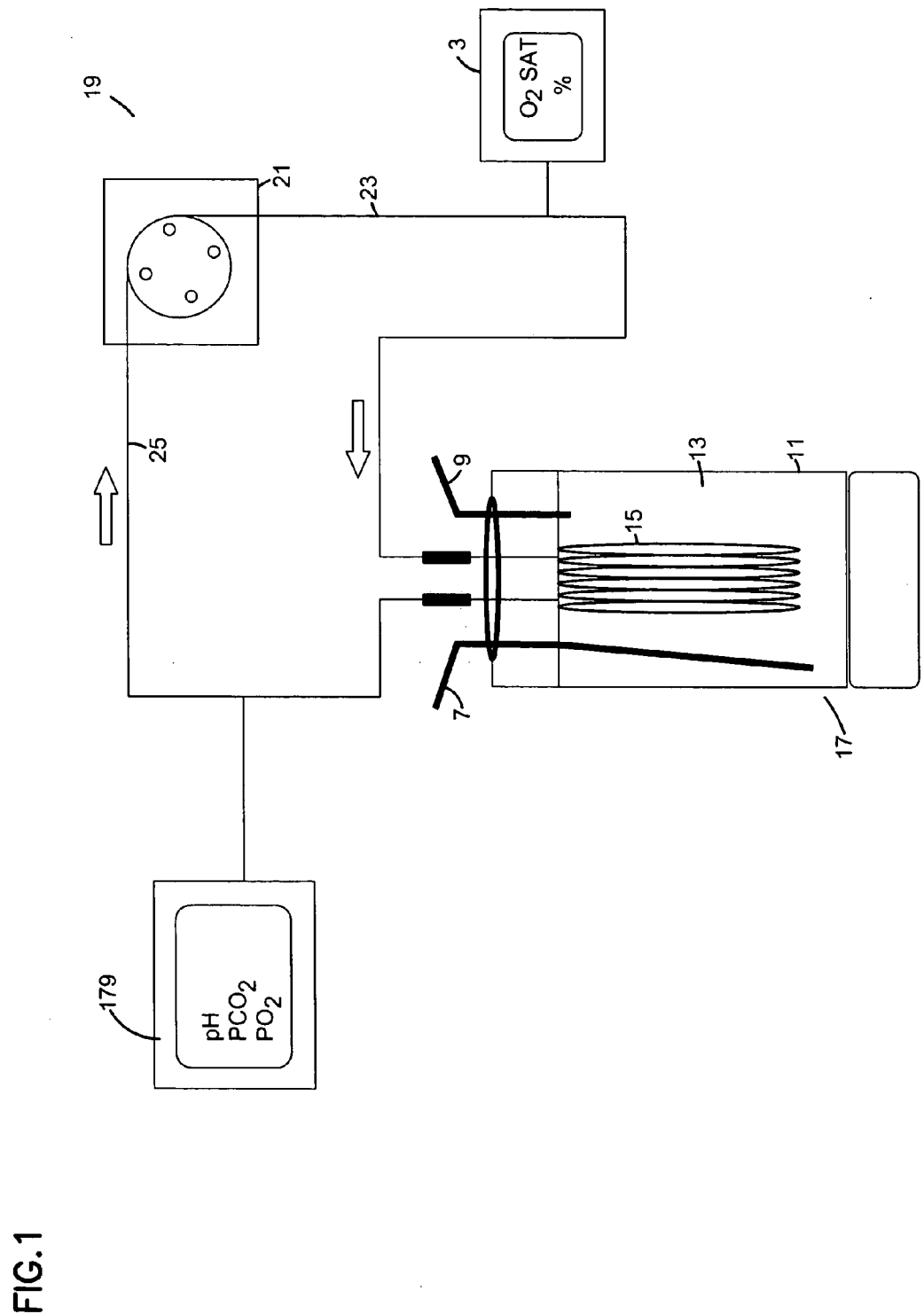
FIG. 1 illustrates an embodiment of the apparatus of the invention.

The present invention relates to a method and apparatus for measuring the rate of oxygen diffusion across a red blood cell membrane. The method and apparatus can be employed to determine a patient's blood oxygen transport, which includes release and/or uptake of oxygen by blood, specifically red blood cells. The method and apparatus of the invention can monitor treatment of, diagnose, or determine susceptibility to diseases and disorders of oxygen release or uptake, such as diseases or disorders of the blood, heart, lungs, and/or circulation, such as angina pectoris or chronic obstructive pulmonary disease. The method and apparatus can also be employed for determining a patient's blood lipid level.

This method can also determine the effect of therapeutic agents and/or protocols on a disease or disorder of oxygen release or uptake. This method can serve as a valuable adjunct to or replacement for a stress test in the evaluation of heart or lung disease, especially in patients whose physical condition make standard stress testing painful or risky.

Oxygen Diffusion Through Red Blood Cell Membranes

Measuring Oxygen Levels in Plasma and Red Blood Cells

Oxygen levels in gasses, in liquids, in blood, such as in blood cells or plasma, and in tissues can be measured in several ways and using a variety of instruments that are known in the art. An oxygen electrode detects free molecular oxygen in a liquid and can be used with biological fluids such as blood, plasma, and the like. Oxygen can also be detected by known spectrophotometric methods, either free or as part of a complex with another molecule.

In red blood cells, nearly all oxygen present is complexed with hemoglobin. Such complexes can be detected by numerous methods known in the art, including spectrophotometric methods, fluorometric methods, potentiometric methods, and the like. For example, for absorption of light in the uv/visible range, the greatest difference in absorbance between hemoglobin and oxygenated hemoglobin occurs at 660 nm. At 805 nm, the isobestic point, there is no difference in absorbance between oxygenated hemoglobin and hemoglobin. Typically, scattering of light by blood components is accounted for by determining absorbance at a wavelength where neither hemoglobin nor oxygenated hemoglobin significantly absorb light. After accounting for scattering, the difference in absorbance at 660 nm yields the concentration of oxygenated hemoglobin. Various instruments exist for convenient and automated measurements of levels of oxygenated hemoglobin.

A small amount of the oxygen present in blood is not complexed with hemoglobin, and can be detected as oxygen in plasma. Plasma oxygen can be detected by numerous methods known in the art, including spectrophotometric methods, fluorometric methods, potentiometric methods, and the like. For example, excitation of a plasma sample at 385 nm results in fluorescence of plasma oxygen which is detectable at 515 nm. Light scattering can be taken into account by a measurement at a wavelength outside the range of fluorescence of absorption of oxygen in plasma. Various instruments exist for convenient and automated measurements of levels of plasma oxygen.

Employing one or more instruments that can determine oxygenated hemoglobin and, optionally, determine plasma oxygen in a system allows both forms of oxygen to be determined in a single sample. In the method and apparatus of the invention a single instrument or detector can determine both oxygenated hemoglobin and plasma oxygen. Measurement of one or both of the plasma oxygen level and/or the level of oxygenated hemoglobin determines a rate at which oxygen crosses the red blood cell membrane to move from being oxygenated hemoglobin to being plasma oxygen. Either or both of these levels can be monitored continuously or intermittently. Alternatively, measuring an amount or level after a predetermined time period can also yield a rate of diffusion across the red blood cell membrane.

Methods Including Measuring Oxygen Diffusion Across a Red Blood Cell Membrane

The present invention relates to a method for determining blood oxygen transport including measuring the rate at which oxygen diffuses across the red blood cell membrane. Delivery of oxygen to tissues from red blood cells and uptake of oxygen into red blood cells from the lungs is vital to life. Blood travels through arteries and capillaries in a tissue to deliver oxygen to the tissue. The speed at which the heart pumps blood determines the amount of time the blood spends in the arteries and capillaries in a tissue. In healthy tissue, blood spends enough time in the tissue for oxygen to leave the red blood cells and diffuse into the tissue in quantities sufficient to keep the tissue healthy.

In a subject suffering from a disease or disorder, the time the blood spends in a tissue can be shorter than the time it takes for sufficient oxygen to leave the red blood cell and enter the tissue. This can be due to factors including slow release of the oxygen from the red blood cell, slow diffusion into the tissue, or both. In this situation, the tissue does not receive sufficient oxygen to remain healthy. For example, in myocardial tissue the residence time of a normal red blood cell and the rate of release of oxygen are typically closely matched. If the myocardial tissue experiences an oxygen deficit, the heart pumps faster and residence time decreases. If the diffusion of oxygen from a red blood cell is abnormally slow, faster pumping increases the number of red blood cells that pass through the tissue, but not the amount of oxygen delivered.

Blood travels through veins and capillaries into the lung to pick up oxygen. In a healthy subject, blood spends enough time in capillaries in the alveoli to pick a full charge of oxygen. In certain diseases and disorders, oxygen transport into the red blood cell is too slow for the cell to pick a full charge of oxygen. This can be due to factors including slow uptake of the oxygen by the red blood cell, slow diffusion from the lung, or both.

The present method can aid in the diagnosis, treatment, and study of diseases and disorders that affect oxygen release or uptake. For example, in certain conditions or disorders, the rate at which a red blood cell delivers or takes up oxygen indicates the presence of, severity of, or susceptibility to the disorder. The present method can be applied to disorders such as heart disease, pulmonary disease, peripheral vascular disease, a disease or disorder of endothelial function, a disease or disorder of the release of transmitters, an endocrine disease, a cerebral disease, a combination thereof, and the like.

Heart disease can include coronary artery disease, angina pectoris, coronary insufficiency, heart failure, disrhythmia, valvular disease, congenital disease, a combination thereof, and the like. Pulmonary disease can include chronic obstructive pulmonary disease emphysema, pneumonia, pulmonary hypertension, chronic infection, congenital disorder, and the like. Peripheral vascular disease can include a slow healing skin disease (e.g. a decubitis ulcer), limb salvage, claudications, arterial or venous insufficiency, diabetes, a combination thereof, and the like. The method also includes embodiments directed to methods of evaluating lipid-lowering treatments, methods of diagnosing or assessing the risk of heart and circulatory disorders such as angina pectoris, and methods of determining a patient's blood lipid level.

The lipid content, particularly the cholesterol content, of the red blood cell membrane is believed to be one factor that affects the diffusion of oxygen through the red blood cell membrane. The cholesterol content of the red blood cell membrane in turn reflects blood cholesterol levels. Therefore, the rate at which oxygen crosses the red blood cell membrane provides a measure of blood cholesterol levels and is useful in diagnosis and treatment of coronary artery disease and other heart and circulatory disorders. The present method of determining a patient's blood lipid level typically includes the steps of obtaining a blood sample from a patient, measuring a rate of oxygen diffusion across a membrane of a red blood cell, and, preferably, correlating the measured rate with established levels of blood lipid to determine the patient's effective blood lipid level.

Measuring the rate of oxygen diffusion across a membrane of a red blood cell preferably includes exposing the red blood cell to oxygen; exposing the red blood cell to an environment depleted of oxygen; and monitoring either a blood or plasma level of oxygen, a level of oxygen bound to hemoglobin, or both. A blood sample obtained from a patient or subject can contain varying amounts of oxygen, and the rate at which oxygen crosses the red blood cell membrane can, in certain conditions, depend on the amount of oxygen present. Exchanging gasses, either by exposing the red blood cells to oxygen or by exposing the red blood cell to an environment depleted of oxygen, standardizes the blood sample to a predetermined level of oxygen and allows significant comparison of numerous blood samples. The red blood cell can be first exposed to oxygen and subsequently exposed to an environment depleted of oxygen. When exposure to oxygen precedes depletion, oxygen is released from red blood cells during and after depletion, and monitoring, typically, monitors this release. Alternatively, the red blood cell can be first exposed to an environment depleted of oxygen and subsequently exposed to oxygen. When depletion of oxygen precedes exposure to oxygen, oxygen is taken up by the red blood cells during exposure, and monitoring, typically, monitors this uptake.

For example, exposing the red blood cell to oxygen can include circulating a blood sample in a closed circuit diffusion system 17. Typically the closed circuit diffusion system 17 includes a chamber 13 containing an atmosphere including oxygen. The level of oxygen in chamber 13 can be varied and be controlled over a wide range. The red blood cells can be exposed to any concentration suitable for standardizing the oxygen level between no oxygen and 100% oxygen. Preferably, the partial pressure of oxygen in chamber 13 is approximately oxygen's partial pressure in air. That is, the atmosphere in chamber 13 includes oxygen at atmospheric gas pressure, for example, 160 mm Hg $O_2$ with 4 mm Hg $CO_2$. Alternatively, the partial pressure of oxygen in chamber 13 can be approximately oxygen's partial pressure in a capillary. That is, the atmosphere in chamber 13 includes oxygen at a pressure, for example, of about 23 mm Hg $O_2$ with 46 mm Hg $CO_2$. Preferably the blood reaches equilibrium with oxygen or with both oxygen and carbon dioxide. In one embodiment, this step of circulating the blood in the closed circuit system lasts for about 0.1 to about 60 minutes.

Exposing the red blood cell to an environment depleted of oxygen can include circulating a blood sample in closed circuit diffusion system 17, with closed circuit diffusion system 17 including chamber 13 containing an atmosphere depleted of oxygen. For example, a suitable oxygen depleted atmosphere is nitrogen or another inert gas, preferably nitrogen. Typically, a commercial or medical grade of nitrogen gas can be employed. Preferably, this depleting step results in complete or nearly complete removal of oxygen from chamber 13, gas permeable tubing 15, and the fluid containing the red blood cells (e.g., plasma). Although considerable deoxygenation is typically observed in the first about 30 seconds, typically, this circulating step lasts longer, in one embodiment about 15 minutes.

Monitoring either a blood level of oxygen, a level of oxygen bound to hemoglobin, or both can be accomplished employing a variety of methods or instruments, as described herein. Monitoring can take place continuously or intermittently through the exposing and circulating steps, or only at two or more discrete time points. For example, the method can include the step of determining the level of saturation of hemoglobin with oxygen achieved during the step of exposing the red blood cell to oxygen. Preferred methods are based on measurements of oxygen saturation of hemoglobin.

In one embodiment, measuring the rate of oxygen diffusion across a red blood cell membrane includes monitoring the ratio of $SO_2$ and $PO_2$ and plotting this ratio as a function of time under the following conditions. $SO_2$ is percent oxygen saturation of hemoglobin and $PO_2$ is the partial pressure of $O_2$ in plasma.
  a) The blood sample is oxygenated, preferably to its maximum, by subjecting compartment three to 1–100% oxygen. Then, $SO_2/PO_2$, $SO_2$, and/or $PO_2$ can be measured.
  b) The blood sample is subjected to a 0% oxygen environment (e.g., 100% nitrogen or another inert gas) in compartment three. Then, $SO_2/PO_2$, $SO_2$, and/or $PO_2$ can be measured, preferably continually, over time.

In these conditions, free oxygen has been depleted, but oxygenated hemoglobin remains a source of oxygen. Release of oxygen from oxygenated hemoglobin, which decreases the level of oxygenated hemoglobin, supplies oxygen to the plasma by diffusion through the red blood cell membrane. To the extent that this diffusion is slowed by the membrane, the plasma levels of oxygen ($PO_2$) remain depressed and the oxygen saturation ($SO_2$) of the hemoglobin remains high for a longer period. Therefore, the rate at which plasma oxygen levels increase, and the rate at which oxygen saturating levels decrease, provide a measure of the rate of diffusion of oxygen through the red blood cell membrane.

In another embodiment, measuring the rate of oxygen diffusion across a red blood cell membrane includes monitoring the ratio of $SO_2/PO_2$ and plotting this ratio as a function of time under the following conditions:
  a) The blood sample is subjected to a 0% oxygen environment (e.g., 100% nitrogen or another inert gas) in compartment three. Then, $SO_2/PO_2$, $SO_2$, and/or $PO_2$ can be measured.
  b) The blood sample is oxygenated, preferably to its maximum, by subjecting compartment three to atmosphere or 100% oxygen. Then, $SO_2/PO_2$, $SO_2$, and/or $PO_2$ can be measured, preferably continually, over time.

In these conditions, oxygenated hemoglobin has been depleted, but free oxygen remains a source of oxygen. Uptake of oxygen by oxygenated hemoglobin, which increases the level of oxygenated hemoglobin, depletes oxygen from the plasma by diffusion through the red blood cell membrane. To the extent that this diffusion is slowed by the membrane, the plasma levels of oxygen ($PO_2$) remain high and the oxygen saturation ($SO_2$) of the hemoglobin remains low for a longer period. Therefore, the rate at which plasma oxygen levels decrease, and the rate at which oxygen saturation levels increase, provide a measure of the rate of diffusion of oxygen through the red blood cell membrane.

Employing the Methods for Diagnosis and Treatment of Disorders

The rate (or amount in a unit of time) of oxygen diffusion through a red blood cell membrane has been shown to correlate with blood oxygen transport, diseases and disorders of blood oxygen transport, and diseases or disorders of oxygen release and/or uptake. Thus, the rate of oxygen diffusion through red blood cell membranes can be useful in treatment and diagnostic regimes for numerous disorders of blood oxygen transport. In addition, the capacity for the red blood cells to take up oxygen from the lungs may be measured by measuring the time for red blood cells to go from a fully deoxygenated state to fully oxygenated state under atmospheric conditions. Similar applications of this method and apparatus exist in peripheral vascular disease and other diseases or processes influenced by oxygen release time and, thereby, oxygen tissue availability.

Since the present method and apparatus require only a blood sample, they offer an alternative to existing methods, which can be invasive and/or expensive. In addition, the present device and method allow earlier monitoring of therapy for a disorder of blood oxygen transport compared to waiting for a measurable effect on the tissue.

Treatment of most disorders of blood oxygen transport involves a therapeutic agent or protocol. Current methods for following such therapies are expensive and time-consuming. In one embodiment, the method of the invention can be used to follow the course of such a therapy. This embodiment includes measuring a rate of oxygen diffusion across a membrane of a red blood cell of the patient. This rate determines the effectiveness of therapy for the disorder or diseases of blood oxygen transport. This can be determined, for example, by correlating the measured rate of oxygen transport with the presence, severity, or susceptibility to the disease or disorder of blood oxygen transport, or with the patient's rate before and after therapy.

Certain disorders of blood oxygen transport have a frequency and severity that correlate with a rate of oxygen diffusion across a membrane of a red blood cell. In one embodiment, the method of the invention can be used to assess a patient's susceptibility to a disease of blood oxygen transport. This embodiment includes measuring a rate of oxygen diffusion across a membrane of a red blood cell from the patient. This rate indicates the patient's susceptibility to a disease or disorder of blood oxygen transport, for example, by correlating the measured rate with the susceptibility to this disease or disorder as observed in a control population, or in the patient, at the measured rate.

Certain diseases or disorders of blood oxygen transport can be related to insufficient uptake or delivery of oxygen to or from a tissue. Under certain undesirable conditions, the blood will reside in a tissue for a shorter time than is required for complete or sufficient delivery or uptake of oxygen. Thus, the present method can provide a way to assess susceptibility to a disease or disorder of blood oxygen transport based on correlation with residence time of blood in a tissue. This method also includes measuring a rate of oxygen diffusion across a membrane of a red blood cell from the patient. The rate indicates the patient's susceptibility to the disorder of blood oxygen transport, for example, by correlating the measured rate with the susceptibility to this disorder as observed in a control population, or in the patient, at the measured rate, and, optionally, correlating the measured rate with residence time of blood the tissue during this disorder.

Pulmonary Disorders

The rate (or amount in a unit of time) of oxygen diffusion through a red blood cell membrane can correlate with the susceptibility to, presence of, or severity of a pulmonary disorder, such as chronic obstructive pulmonary disease. Thus, the rate of oxygen diffusion through a red blood cell membrane can be useful and treatment in diagnosis of such disorders. Since the present method and apparatus require only a blood sample, they offer an alternative to existing methods, such as pulmonary stress tests, and are noninvasive and less expensive. In addition, the present device and method allow earlier monitoring of a therapy for a pulmonary disorder compared to waiting for a noticeable effect on a tissue of the lung, such as the size of an airway or the function of a bronchiole.

Treatment of most pulmonary diseases includes therapeutic agents and protocols, such as inhalation therapies, positive pressure aids, nebulizers, etc. Current methods of following the progress of such therapies are expensive and time-consuming. In one embodiment, the method and device of the invention can be used to follow therapies for pulmonary diseases. This embodiment includes measuring a rate of oxygen diffusion across a membrane of a red blood cell of the patient. This rate determines the effectiveness of a therapy for a pulmonary disorder, for example, by correlating the measured rate with the presence or degree of the pulmonary disease, and comparing this presence or degree to the patient's previous level of disease.

Certain pulmonary diseases, such as chronic obstructive pulmonary disease, have a frequency and severity that correlate with a rate of oxygen diffusion across a membrane of a red blood cell. In one embodiment, the method of the invention can be used to assess a patient's susceptibility to a pulmonary disease. This embodiment includes measuring a rate of oxygen diffusion across a membrane of a red blood cell from the patient. This rate indicates the patient's susceptibility to the pulmonary disease, for example, by correlating the measured rate with susceptibility to the disease observed in a control population, or in the patient, at the measured rate.

Certain pulmonary diseases are characterized by insufficient uptake of oxygen from the lungs. This can result from the situation in which oxygen transport from the lungs has been slowed by the disease, oxygen uptake by the blood has been slowed by the disease, or blood is in the lung for a shorter time due to the disease. In such a disease, the rate at which oxygen is taken up by the blood may be too slow. Thus, the present method can provide another way to assess susceptibility to or the presence of a pulmonary disease based on correlation with residence time of blood in the lungs. This method also includes measuring a rate of oxygen diffusion across a membrane of a red blood cell from the patient. This rate indicates the patient's susceptibility to the pulmonary disease, for example, by correlating the measured rate with the susceptibility to the pulmonary disease observed in a control population, or in the patient, at the measured rate and, optionally, correlating the measured rate with residence time of blood in the lung.

Heart and Circulatory Disorders

The rate (or amount in a unit of time) of oxygen through a red blood cell membrane correlates with susceptibility to, presence of, or severity of a heart or circulatory disease. Thus, the rate of oxygen diffusion through a red blood cell membrane can be useful in treatment and diagnostic regimes, as well as assessment of the effectiveness of therapies, for numerous heart or circulatory disorders. Since the present method and apparatus require only a blood sample, they offer an alternative to existing methods, such as arteriography, and are noninvasive and less expensive. In addition, the present device and method allow earlier monitoring of therapy, rather than waiting for a noticeable effect on the tissue of the heart or blood vessels.

Treatment of most heart and circulatory disorders employs a therapeutic agent or protocol. Current methods of following such therapies typically are expensive and time-consuming. In one embodiment, the method of the invention can be used to follow the course of such a therapy for a heart or circulatory disorder. This embodiment includes measuring a rate of oxygen diffusion across a membrane of a red blood cell of the patient. This rate determines the effectiveness of the therapy for a heart or circulatory disorder, for example, by correlating the measured rate with the measured rate at a particular disease state in a control population, or in the patient.

Certain heart and circulatory disorders have a frequency and severity that correlate with a rate of oxygen diffusion across a membrane of a red blood cell. In one embodiment, the method of the invention can be used to assess a patient's susceptibility to a heart or circulatory disorder. This embodiment includes measuring a rate of oxygen diffusion across a membrane of a red blood cell from the patient. This rate indicates the patient's susceptibility to the heart or circulatory disorder, for example, by correlating the measured rate as observed in a control population, or in the patient, at the measured rate.

Certain heart and circulatory disorders are related to insufficient delivery of oxygen to a tissue. For example, under certain conditions, blood is in the arteries supplying the tissue for a shorter time or with inadequate tissue distribution than in the absence of the disorder. Therefore, the rate at which oxygen diffuses out of the red blood cell and the blood vessel and reaches the tissue may be too slow to release oxygen during the short residence time in the tissue. Thus, the present method can provide another way to assess susceptibility to the heart disease or circulatory disorder based on the correlation with residence time of blood in the tissue. This method also includes measuring a rate of oxygen diffusion across a membrane of a red blood cell from the patient. This rate indicates the patients susceptibility to the heart or circulatory disorder, for example, by correlating the measured rate with the susceptibility to the disorder as observed in a control population, or in the patient, at the measured rate, and, optionally, correlating the measured rate with residence time of blood in the tissue.

Angina and Other Lipid-Related Heart and Circulatory Disorders

The rate (or amount in a unit of time) of oxygen diffusion through a red blood cell membrane has been shown to correlate with blood lipid, particularly cholesterol, levels in the cell membrane and in plasma. This knowledge makes the rate of oxygen diffusion though red blood cell membranes useful in treatment and diagnostic regimes for numerous heart or circulatory disorders, such as angina pectoris. Since the present method and apparatus require only a blood sample, they offer an alternative to existing methods, such as arteriography, and are noninvasive and less expensive. In addition, the present device and method allow earlier monitoring of therapy rather than waiting for a noticeable effect on a parameter such as the diameter of a coronary artery.

Treatment of heart and circulatory disorders involves therapy, such as administration of many medicines, directed at lowering a patient's blood lipid levels. Current methods of following the cardiovascular progress of lipid-lowering therapies are expensive and time-consuming. In one embodiment, the method of the invention can be used to follow the course of such lipid-lowering therapy. This embodiment includes measuring a rate of oxygen diffusion across a membrane of a red blood cell of the patient. This rate determines the effectiveness of a lipid-lowering therapy, for example, by correlating the measured rate with lipid levels to determine the patient's relative or absolute lipid level, and comparing the patient's lipid level to the patient's previous lipid levels.

Certain heart and circulatory disorders, such as angina pectoris, have a frequency and severity that correlate with blood levels of cholesterol and like lipids. In one embodiment, the method of the invention can be used to assess a patient's susceptibility to angina pectoris. This embodiment includes measuring a rate of oxygen diffusion across a membrane of a red blood cell from the patient. This rate indicates the patient's susceptibility to angina pectoris, for example, by correlating the measured rate with the susceptibility to angina observed in a control population, or in the patient, at the measured rate.

Angina can also be related to insufficient delivery of oxygen to the tissue of the heart. Under high stress blood is in the arteries supplying the heart for a shorter time than during periods of low stress. Therefore, the rate at which oxygen diffuses out of the red blood cell and the blood vessel may be too slow to release oxygen during the short residence time in the heart during high stress. This rate may be sufficient to deliver oxygen to the tissue during the longer residence times of low stress. Thus, the present method can provide another way to assess susceptibility to angina based on the correlation with residence time of blood in the heart. This method also includes measuring a rate of oxygen diffusion across a membrane of a red blood cell from the patient. This rate indicates the patient's susceptibility to angina pectoris, for example, by correlating the measured rate with the susceptibility to angina observed in a control population, or in the patient, at the measured rate, and, optionally, correlating the measured rate with residence time of blood in the heart during stress.

Diagnosis and Treatment

In the context of the present invention, the terms "treat" and "therapy" and the like refer to alleviate, slow the progression, prophylaxis, attenuation or cure of existing disease. Prevent, as used herein, refers to putting off, delaying, slowing, inhibiting, or otherwise stopping, reducing or ameliorating the onset of such diseases or disorders. The method of the present invention may be used with any mammal. Exemplary mammals include, but are not limited to rats, cats, dogs, horses, cows, sheep, pigs, and more preferably humans.

Apparatus for Measuring the Rate of Oxygen Diffusion Across a Red Blood Cell Membrane An Overview of the Apparatus The present invention also relates to an apparatus for measuring the rate of oxygen diffusion across the membrane of a red blood cell. The apparatus includes a system for receiving and transporting the red blood cell, a system for subjecting the red blood cell to conditions where oxygen will diffuse across its membrane, and a system for measuring the amount of oxygen inside and/or outside of the red blood cell. Embodiments of the apparatus are illustrated schematically in FIGS. 1–4.

FIG. 1 schematically illustrates a first embodiment of the apparatus for measuring the rate of oxygen diffusion across a red blood cell membrane. This embodiment includes an oxygen level detector, a gas exchange system, and a red blood cell transport system. The red blood cell transport system is adapted and configured for transporting red blood cells through the gas exchange system and the oxygen level detector. The gas exchange system is adapted and configured to exchange gasses with the red blood cell. The oxygen level detector is adapted and configured for detecting oxygen levels in a red blood cell or in fluid surrounding a red blood cell. Each of these detectors and systems is described in greater detail below.

Figure 2A:
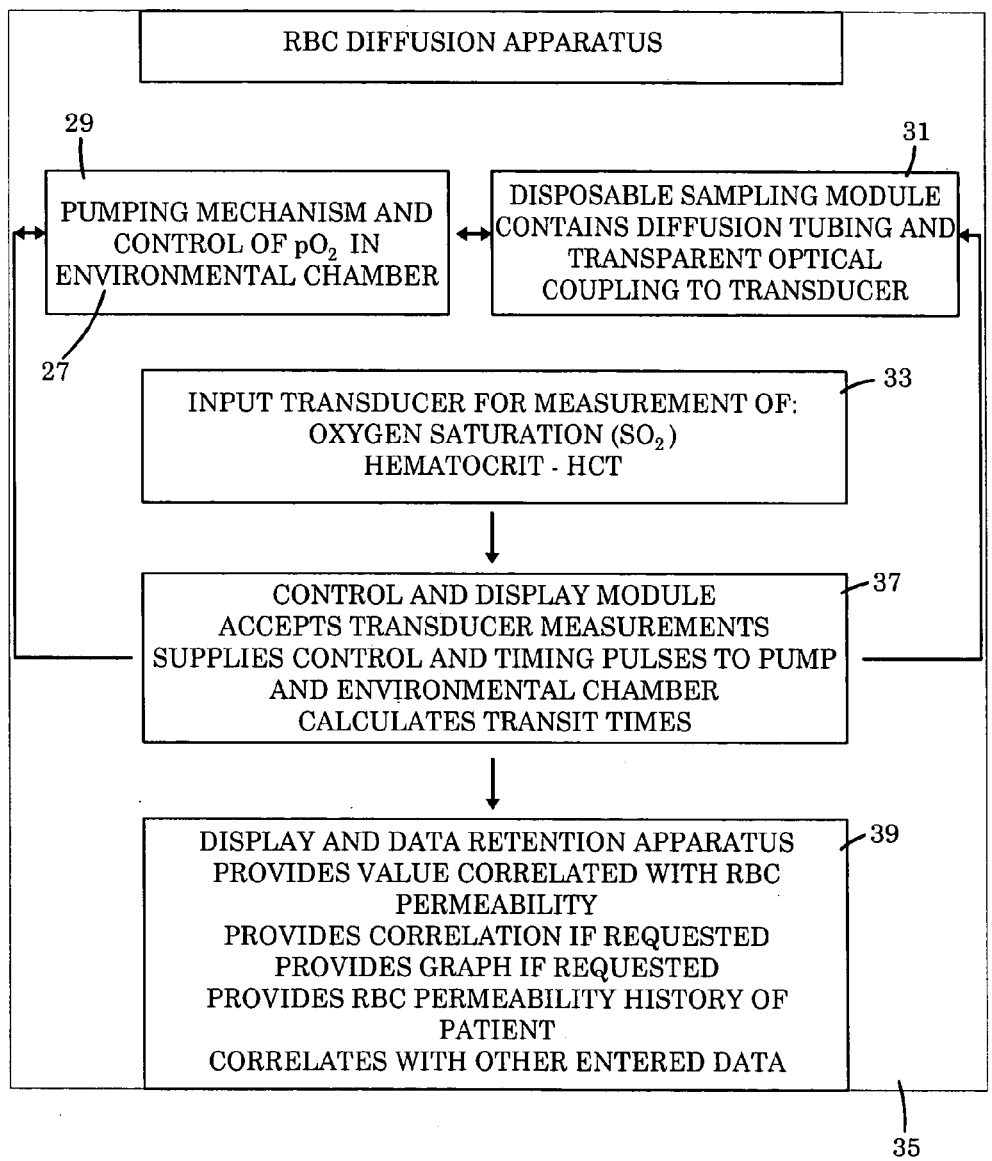
FIGS. 2A and 2B are schematic illustrations of preferred embodiments of an apparatus according to the invention.
Figure 2B:
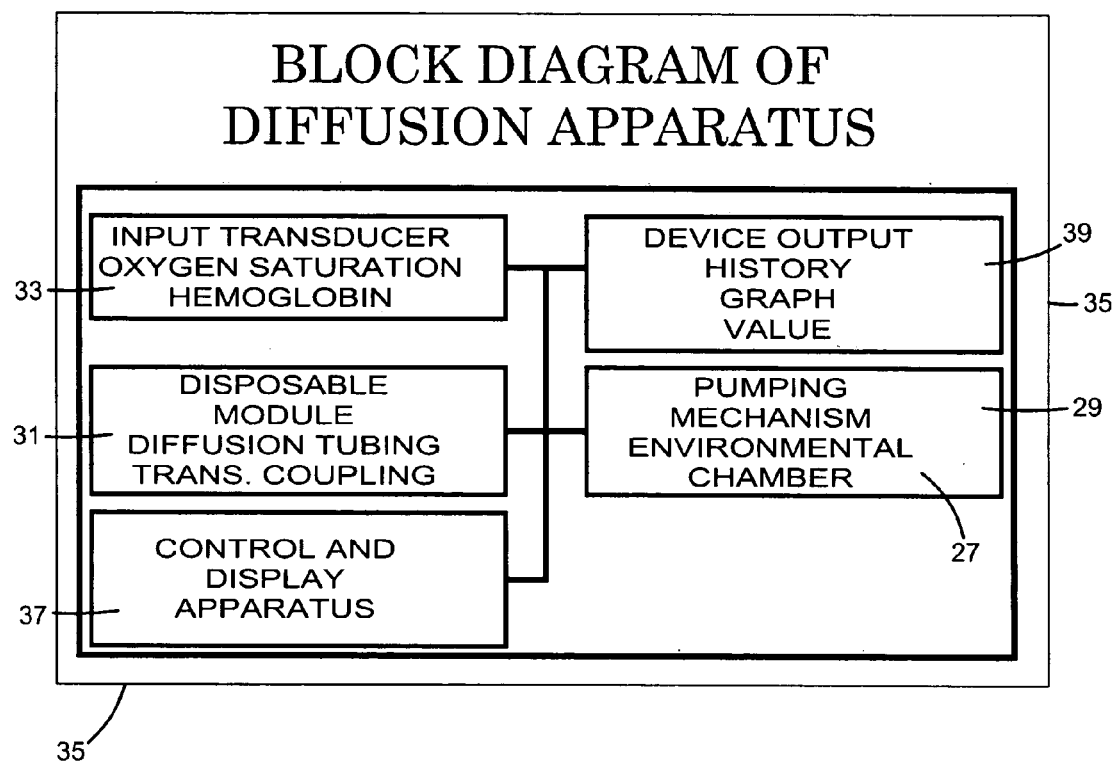

FIGS. 2A and 2B schematically illustrate a second and preferred embodiment of the apparatus for measuring the rate of oxygen diffusion across a red blood cell membrane. This embodiment is illustrated around five components. The gas exchange system 3, includes a chamber 13, which in this embodiment is the first component, an environmental chamber 27. Red blood cell transport system 19 includes the second and third components, a pump system 29 and a sample receiving and diffusion system 31, respectively. The fourth component, a measuring system 33, includes oxygen level detector 3. The fifth component is a control system 35. Each component is coupled, for example, either mechanically or electrically, to one or more of the other components. Each of the components operates cooperatively with one or more of the other components. Such coupling and cooperation is described below. Each of these components in a preferred embodiment can have a variety of preferred characteristics, which are described herein below.

Functional Considerations

In a typical embodiment, the apparatus employs a cyclical process to measure the rate at which oxygen crosses the membrane of a red blood cell. In one such cyclical process, a blood sample passes several times through a gas exchange system and becomes homogeneous between passes. For example, the process can include completely oxygenating a blood sample followed by passing the blood through a deoxygenator at a predetermined transit time. As the blood passes through the deoxygenator, the sample releases oxygen and the $S_{O2}$ changes. Although a portion of the sample is always in the deoxygenator, the sample is a homogenized before the oxygen level is read, at the beginning of the next cycle. Thus, the residence time of the blood sample in the deoxygenator is a weighted function of the size of the deoxygenator compared to the size of the blood sample. Typically, the blood is transported at a fast flow rate and the deoxygenator has a small volume compared to its surface area and the residence time does not affect the measured rate. The residence time in the deoxygenator can be made directly comparable to the time the blood spends in a tissue.

According to the method of the present invention, the apparatus can measure either the plasma oxygen level ($PO_2$) or the oxygen saturation ($SO_2$) of the hemoglobin, or both. The time for measuring the oxygen saturation level is typically faster than the measurement time of the plasma oxygen level. Additionally, the rate of change of the oxygen saturation level is faster than the rate of change of the plasma oxygen level, thus an accurate $SO_2$ level can be determined in a shorter time period.

The cycle time to perform a test, that is, to determine the oxygen diffusion rate across the red blood cell membrane, can be regulated by the components of the apparatus. In particular, the gas permeable tubing (e.g. 15 in FIG. 1) or microporous hydrophobic membrane (e.g. 123 in FIGS. 3 and 4) can be sized to provide the desired test cycle time. For example, a smaller diameter tubing provides more surface area per volume of blood sample, thereby decreasing the time for diffusion from the blood sample. A decrease in the thickness of the tubing can also decrease the diffusion time. Various shapes of tubing can also decrease the time by increasing the surface area; tubing cross sections such as flat or rectangular shapes provide more surface area per volume than does a circular cross section. A longer tubing length will also increase the surface area. However, the sample size might have to be increased, which can be disadvantageous because a smaller blood sample volume will provide quicker results.

Red Blood Cell Transport System

The apparatus employs a red blood cell transport system to transport the red blood cells through the various parts of the apparatus. For example, the red blood cell must be transported into the apparatus, through the system for subjecting the red blood cell to conditions where oxygen will diffuse across its membrane, and through the system for measuring the amount of oxygen inside and/or outside of the red blood cell. Specific and preferred embodiments of the red blood cell transport system are schematically illustrated in FIGS. 1–4.

FIG. 1 schematically illustrates an embodiment of red blood cell transport system 19. As illustrated, red blood cell transport system 19 includes a pump 21, inflow tubing 23, and outflow tubing 25. Red blood cell transport system 19 transports plasma or another fluid containing red blood cells through one or more oxygen level detectors 3, into gas exchange system 5, and from gas exchange system 5 back to pump 21. Pump 21 can be a peristaltic pump, or any other suitable pump for transporting fluid containing red blood cells. Alternatively, red blood cell transport system 19 can include an aspirator, an apparatus that causes flow based on capillary action, or any of several other suitable apparatus for transporting fluids containing red blood cells.

FIGS. 2A and 2B schematically illustrate an embodiment of red blood cell transport system 19 including a pump 21, e.g. pump system 29, and a receiving and diffusion system 31. Receiving and diffusion system 31 includes sampling apparatus 117, diffusion apparatus 119, and transparent optical system 121. Sampling apparatus is adapted and configured to introduce fluid containing red blood cells into red blood cell transport system 19. For safety in handling blood, a preferred receiving and diffusion system 31 is adapted and configured so that when filling, coupling to the apparatus, or uncoupling from the apparatus, no blood leaves the system. In this way, an operator cannot come into contact with blood from the system. In one embodiment, sampling apparatus 117 includes a port that can receive an injection of blood or another fluid containing red blood cells, e.g. from a syringe. Preferably, blood can be introduced into red blood cell transport system 19 directly from a vacutainer without removing the cap of the vacutainer by employing sampling apparatus 117 (see also FIG. 9).

This can be accomplished by a sampling apparatus 117 that employs a puncture system 41 with a puncture spike 43, such as a plastic puncture spike 45. Preferably, puncture system 41 is adapted and configured to increase user safety, that is, to reduce the possibility that the user will come into contact with or suffer a puncture from puncture spike 43 or plastic puncture spike 45. One embodiment increases user safety by positioning plastic puncture spike 45 in a spike well 47. Spike well 47 can be defined by a casing or housing at least partially surrounding puncture spike 43. Advantageously, the container of blood is vented and air is allowed into the container during transfer of blood into red blood cell transport system 19. Venting can be accomplished by employing puncture spike 43 or plastic puncture spike 45 in cooperation with a vent (not shown).

Pump

Typically, blood is withdrawn from a container and into red blood cell transport system 19 by pump 21, e.g. pump system 29. Pump 21 can be actuated by coupling a container of fluid containing red blood cells to the apparatus, or manually by the operator. A preferred sample receiving and diffusion system 31 can receive an approximately 10 ml or smaller sample of whole blood from a syringe or vacutainer. Preferably, the blood sample has a volume less than about 3 ml, preferably less than about 1 ml. Preferably pump 21, e.g. pump system 29, can empty the container of blood or other fluid containing red blood cells rapidly. That is, the pump empties the container in a time suitable for running a test in a clinical laboratory, preferably less than about 3 minute, preferably less than about 1 minute. Further, a preferred receiving and diffusion system 31 can be flushed of blood and filled with air or liquid, typically in a short time such as less than one minute.

Pump 21, e.g. pump system 29, can pump a sample of blood or another fluid containing red blood cells through environmental chamber 27. Preferably, receiving and diffusion system 31 is adapted and configured to cooperate with environmental chamber 27 to achieve conditions effective for diffusion of oxygen across the membrane of a red blood cell. For example, pump 21, e.g. pump system 29, and receiving and diffusion system 31 typically cycle the blood sample through environmental chamber 27 at a rate effective for diffusion of oxygen across the membrane of a red blood cell. In one embodiment, pump 21 pumps the fluid containing red blood cells through environmental chamber 27 at a rate effective to assure complete oxygenation with a single pass through environmental chamber 27.

Preferably pump 21, e.g. pump system 29, can maintain a low flow rate during oxygenation and withdrawing blood from a container and a high flow rate during deoxygenation. In one embodiment pump 21, can maintain a steady or rapid pulsatile flow of about 5 to about 10 ml of blood without touching the sample (e.g. through tubing). Preferably, pump 21, e.g. pump system 29, can accurately maintain a pumping rate within a range of the desired rate plus or minus 20%, preferably 10%. Preferably, pump 21, e.g. pump system 29, maintains a substantially constant volume of fluid in the apparatus during pump cycles. Although a volumetric change during the pumping cycle could be accommodated by adding a buffer chamber (not shown) to pump 21, e.g. pump system 29, this would affect the captured volume accuracy. Such system distensibility might add variability to the volume against pressure curve for the apparatus, thus affecting the captured volume accuracy. In one preferred embodiment, pump 21, e.g. pump system 29, can pump the fluid at up to 15 ml/min, which can, for example, take the entire sample past any point in about 20 seconds.

Figure 5:
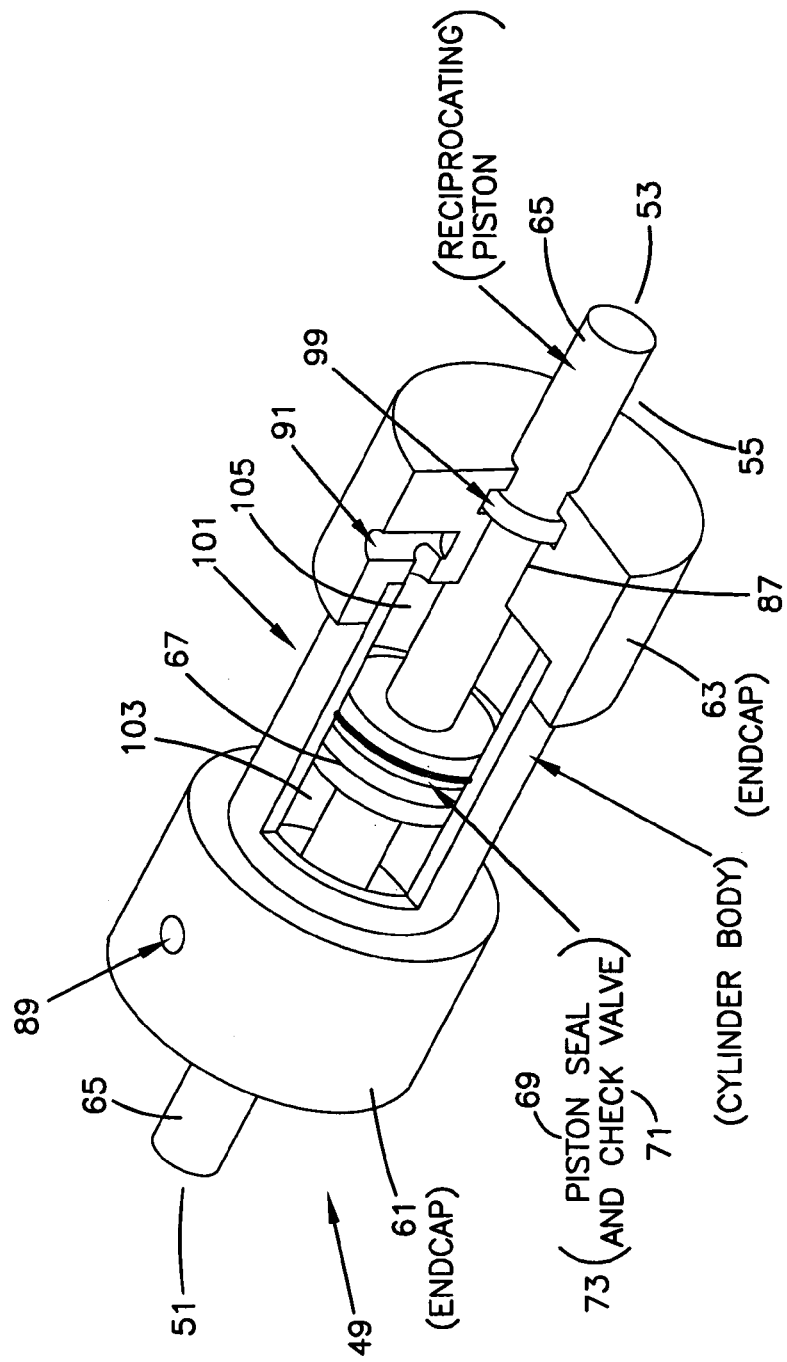
FIG. 5 illustrates a cutaway view of a pump according to the invention.
Figure 6:
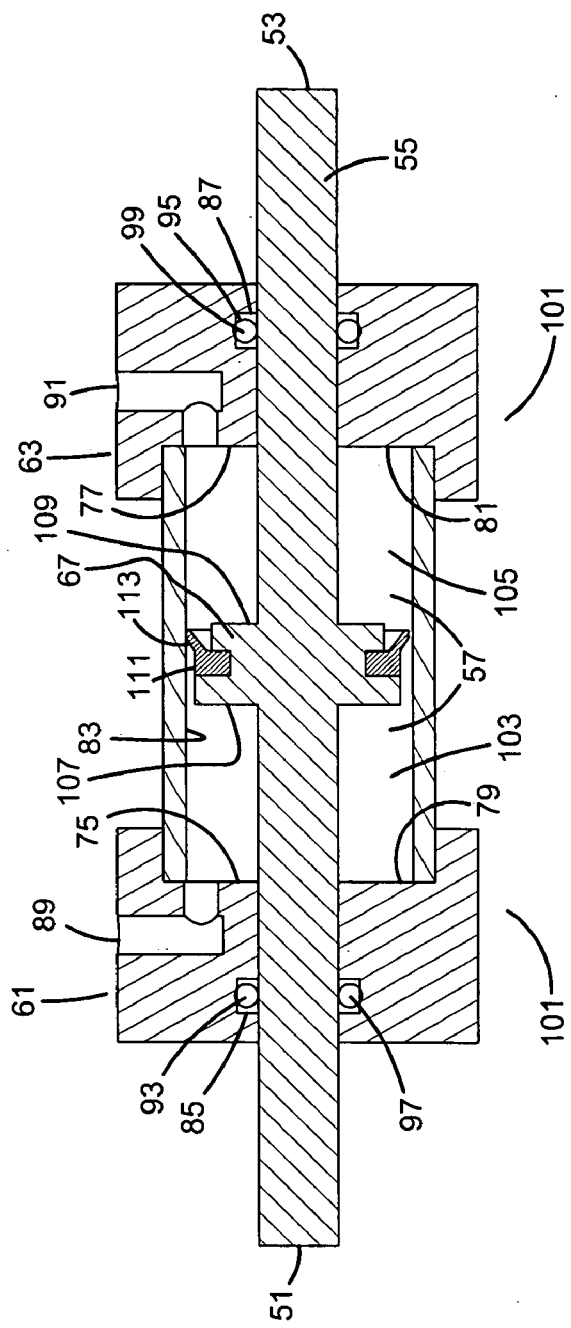
FIG. 6 illustrates a cross sectional view of a pump according to the invention.

In one embodiment pump 21 or pump system 29 includes a reciprocating piston pump 49. Such a pump 21 can include a pump check valve 51. FIGS. 5 and 6 illustrate cut away and cross sectional views, respectively, of an embodiment of a reciprocating piston pump 49. Reciprocating piston pump 49 can be made from injection molded parts. One or more cams 187 (FIG. 13) can drive reciprocating piston pump 49 by pushing on first end 51 and second end 53 of piston 55. Such a reciprocating piston pump 49 can expel virtually all of the cylinder 57 volume each cycle. Thus, reciprocating piston pump 49 preferably has little tendency to harbor air bubbles.

Reciprocating piston pump 49 includes a reciprocating piston 55 at least partially enclosed within a pump housing 101. Preferred pump housing 101 includes a cylinder body 59 and first and second endcaps 61 and 63, respectively. Cylinder body 59 together with first and second endcaps 61 and 63 define generally cylindrical cylinder 57. For example, cylinder body 59 can fit into a generally cylindrical or disk shaped depression (75 and 77) defined by each of endcaps 61 and 63. The bottoms (79 and 81) of each cylindrical depression together with an interior wall 83 of cylinder body 59 define cylinder 57. In the illustrated embodiment, each of first and second endcaps 61 and 63, respectively, defines a generally axial and generally centered through bore, 85 and 87, respectively. Typically, each endcap also defines an annular groove (93 and 95) around each of through bores 85 and 87. Each of annular grooves 93 and 95 are configured to house a shaft seal, 97 and 99, respectively. Each endcap 61 and 63 also defines a through bore for fluid communication between cylinder 57 and the apparatus exterior to the pump. For example, first endcap 61 defines a inlet bore 89 and second endcap 63 defines an outlet bore 91.

Piston 55 includes a piston shaft 65, which can be a unitary body, a piston body 67, a piston seal, 69 and a piston check valve 71. A single member can form both piston seal 69 and piston check valve 71. Such a member is referred to as a combined piston seal and check valve 73. Piston shaft 65 is at least partially housed within and generally coaxial with cylinder body 59. Piston shaft 65 typically extends through first through bore 85 of first endcap 61 and through second through bore 87 of second endcap 63. Piston shaft 65 sealingly engages each of shaft seals 97 and 99, to effectively prevent fluid from escaping from cylinder 57 by way of either through bore 85 or 87. Piston body 67 extends generally radially from piston shaft 65 and is generally disk shaped. Piston body 67 extends to a diameter slightly less than inside diameter of cylinder body 59. Piston seal 69 is adapted and configured to prevent unwanted fluid flow around the edge of piston body 67. Piston check valve 71 is adapted and configured to allow desired fluid flow around the edge of piston body 67.

During operation of the pump, reciprocal motion of piston body 67, piston seal 69, and piston check valve 71 draw fluid into and expel fluid from cylinder 57. Advantageously, movement of piston body 67, piston seal 69, and piston check valve 71 in the direction of second endcap 63 both draws fluid into first portion 103 of cylinder 57 through inlet 89 and expels fluid from second portion 105 of cylinder 57 through outlet 91. Advantageously, movement of piston body 67, piston seal 69, and piston check valve 71 in the direction of first endcap 61 displaces fluid from first portion 103 of cylinder 57 into second portion 105 of cylinder 57, but not through either inlet 89 or outlet 91. This can be accomplished in cooperation with a check valve external to pump 49 but in fluid communication with either inlet 89 or outlet 91. First portion 103 of cylinder 57 is generally defined by interior wall 83, first bottom 79, and first surface 107 of piston body 67. Second portion 105 of cylinder 57 is generally defined by interior wall 83, second bottom 81, and second surface 109 of piston body 67.

Preferably, in this embodiment, pump 49 includes a combined piston seal and check valve 73. Combined piston seal and check valve 73 typically includes a seal body 111 and a valve flap 113. Piston body 67 is adapted and configured to retain seal body 111, for example, within an annular groove 115 around the circumference of piston body 67. Valve flap 113 projects from seal body 111 flexibly and is generally directed toward a surface of piston body 67, for example, toward first surface 107 or second surface 109, preferably second surface 109. When the piston is at rest, valve flap 113 sealingly contacts cylinder body 59 along its interior surface 83. When the piston is moving, its direction of movement can be described with reference to the direction in which the valve flap 113 extends from seal body 111 or by the surface of piston body 67 that is being moved toward an end of cylinder 57. For example, in the preferred embodiment with valve flap 113 is directed toward second surface 109 of piston body 67, and also toward second endcap 63 or second surface 81. In this embodiment, movement of piston body 67 toward second endcap 63 urges valve seal 113 into sealing engagement with cylinder body 59. Movement of piston body 67 toward first endcap 61 urges valve flap 113 away from cylinder body 59, which allows fluid flow around the piston body and from first portion of cylinder 57 into second portion of cylinder 57. Such an arrangement provides a pump that draws fluid in through inlet 89 and expels fluid from outlet 91.

Diffusion Apparatus

In a preferred embodiment, red blood cell transport system 19 includes a diffusion apparatus 119 that works in cooperation with gas exchange system 5 and environmental chamber 27. Red blood cell transport system 19 transports red blood cells into and through gas exchange system 5 to expose the red blood cells to different concentrations and compositions of gases, which allows oxygen diffusion across the red blood cell membrane. Diffusion apparatus 119 provides the apparatus in which red blood cells encounter these different concentrations and compositions of gases. Diffusion apparatus 119 is adapted and configured to provide contact between one or more gases in gas exchange system 5 and the red blood cell.

Diffusion apparatus 119 can include gas permeable tubing 15. Gas permeable tubing 15 has a lumen (not shown) that is used to contain, preferably flowing, fluid containing red blood cells. A preferred fluid containing red blood cells is blood that has been treated with an anticoagulant. Gas permeable tubing 15 is adapted and constructed to allow diffusion of gases from chamber 13 or environmental chamber 27 into the lumen and into any fluid in the lumen. Gas permeable tubing 15 can be constructed from a hydrophobic microporous material that allows gas to diffuse relatively freely, but that will not allow liquid to pass through the material. Gas permeable tubing 15 can be composed of silicone or silastic material. Gas permeable tubing 15 can be a component of a cartridge-type insert which can be easily inserted into and removed from gas exchange system 5. Preferably, such a cartridge-type insert is priced and constructed to be disposable.

Gas permeable tubing 15 can be adapted and configured as a hollow fiber filtration apparatus. In one embodiment of the hollow fiber apparatus, gas flows through the hollow fibers. Blood or another fluid containing red blood cells flows around and contacts the outside of the fibers. The fibers are arrayed in a manner that ensures high contact area and high-performance.

Diffusion apparatus 119 preferably includes one or more hydrophobic microporous membranes 123. Hydrophobic microporous membrane 123 is adapted and configured to allow gas to diffuse through it relatively freely, but is impermeable to liquid. Advantageously, hydrophobic microporous membrane 123 allows gas bubbles to pass through it, and is effective for de-bubbling blood or other fluid containing red blood cells. Compared to hollow fibers, a hydrophobic microporous membrane 123 has more consistent permeability and thickness. Hence, employing hydrophobic microporous membrane 123, compared to a hollow fiber, provides more consistent transfer of gases between chamber 13 or environmental chamber 27 and the fluid containing red blood cells. The apparatus can include a first hydrophobic microporous membrane 123 for bringing red blood cells to a condition employed for the start of the measurement and a second hydrophobic microporous membrane 123 for exposing red blood cells to conditions that induce diffusion of oxygen across the red blood cell membrane. Advantageously, the apparatus employs a single hydrophobic microporous membrane 123. Hydrophobic microporous membrane 123 can be made of silicone, silastic material, polypropylene, or any other suitable hydrophobic material that yields the necessary rate and quantity of gas movement. Preferably hydrophobic microporous membrane 123 is made of polypropylene.

Preferably, the time for equilibration under a given sequence of conditions of oxygen diffusion is short enough to provide a convenient test in a medical laboratory. For example, a simple comparative test can be conducted in less than about 20 min, preferably less than about 6 min, more preferably less than about 2 min. A more complex time course test can be conducted and analyzed in less than about 40 min, preferably less than about 15 min, preferably less than about 5 min.

Diffusion apparatus 119 can also include a debubbler 125. Debubbler 125 is preferably down stream of hydrophobic microporous membrane 123. Debubbler 125 includes a hydrophobic filter 127 with a pore size sufficiently large that blood or another fluid containing red blood cells flows freely through it, yet it still traps bubbles. The trapped bubbles leave the liquid and are vented.

Transparent Optical System

In a preferred embodiment, red blood cell transport system 19 includes a transparent optical system 121 that works in cooperation with oxygen level detector 3 and/or measuring system 33. Transparent optical system 121 is arranged and configured for spectrophotometric, fluorometric, or other light-based detection of oxygen levels in plasma or bound to hemoglobin. Typically, transparent optical system 121 provides a structure that can contain blood or another fluid containing red blood cells and that provides light a generally transparent pathway for interacting with or passing through the fluid. Preferably, transparent optical system 121 includes cuvette 129.

Cuvette 129 typically includes cuvette body 131 and one or more fittings 133 (FIGS. 7 and 8). Cuvette body 131 defines a passage 135 through which fluid can pass. Typically, passage 135 is defined by at least two parallel sides formed of a transparent or optically clear material such as glass or plastic, preferably polycarbonate. Preferably, passage 135 has a square or rectangular cross-section (FIGS. 7 and 8). In the illustrated embodiment, each end of passage 135 is sealingly capped with a fitting 133. Fitting 133 includes a through bore 139, which is adapted and configured for conducting fluid through fitting 133 and into passage 135. Through bore 139 is also, advantageously, adapted and configured to couple with the remainder of the tubing or other apparatus through which fluid flows in the red blood cell transport system 19.

Valves

In a preferred embodiment, red blood cell transport system 19 can include one or more valves, preferably check valves. Red blood cell transport system 19 can include a valve or check valve at any point where the valve improves performance of the apparatus. For example, red blood cell transport system 19 advantageously includes a first check valve 141 between sampling apparatus 117 and pump 21, e.g. between puncture system 41, reciprocating piston pump 49. Such a check valve can facilitate filling the red blood cell transport system with fluid and prevent back flow into the container originally holding the fluid. In addition, such a check valve can prevent dripping of blood from the apparatus. Preferably, red blood cell transport system 19 includes a second check valves 43 positioned downstream from the outlet from pump 21, e.g. reciprocating piston pump 49. Such a check valve can prevent back flow into the pump and also assist in maintaining pressure in the red blood cell transport system 19 beyond or downstream of second check valve 143.

In a preferred embodiment, the portion of red blood cell transport system 19 cooperating with oxygen level detector 3 and/or measuring system 33 and with gas exchange system 17 and/or environmental chamber 27 is maintained at a positive pressure. In this embodiment, red blood cell transport system 19 can include a third check valve 145 downstream of second check valve 143, oxygen level detector 3 or measuring system 33, and gas exchange system 17 or environmental chamber 27. Preferably, third check valve 145 is a check valve that requires a positive pressure to open, and which also readily closes at this pressure. Such a check valve can be called a high-pressure check valve. Preferably, third check valve 145 opens at about 3.6 PSI, or 0.25 bar, although other opening pressures are also effective.

Transport System Circuits

Figure 3:
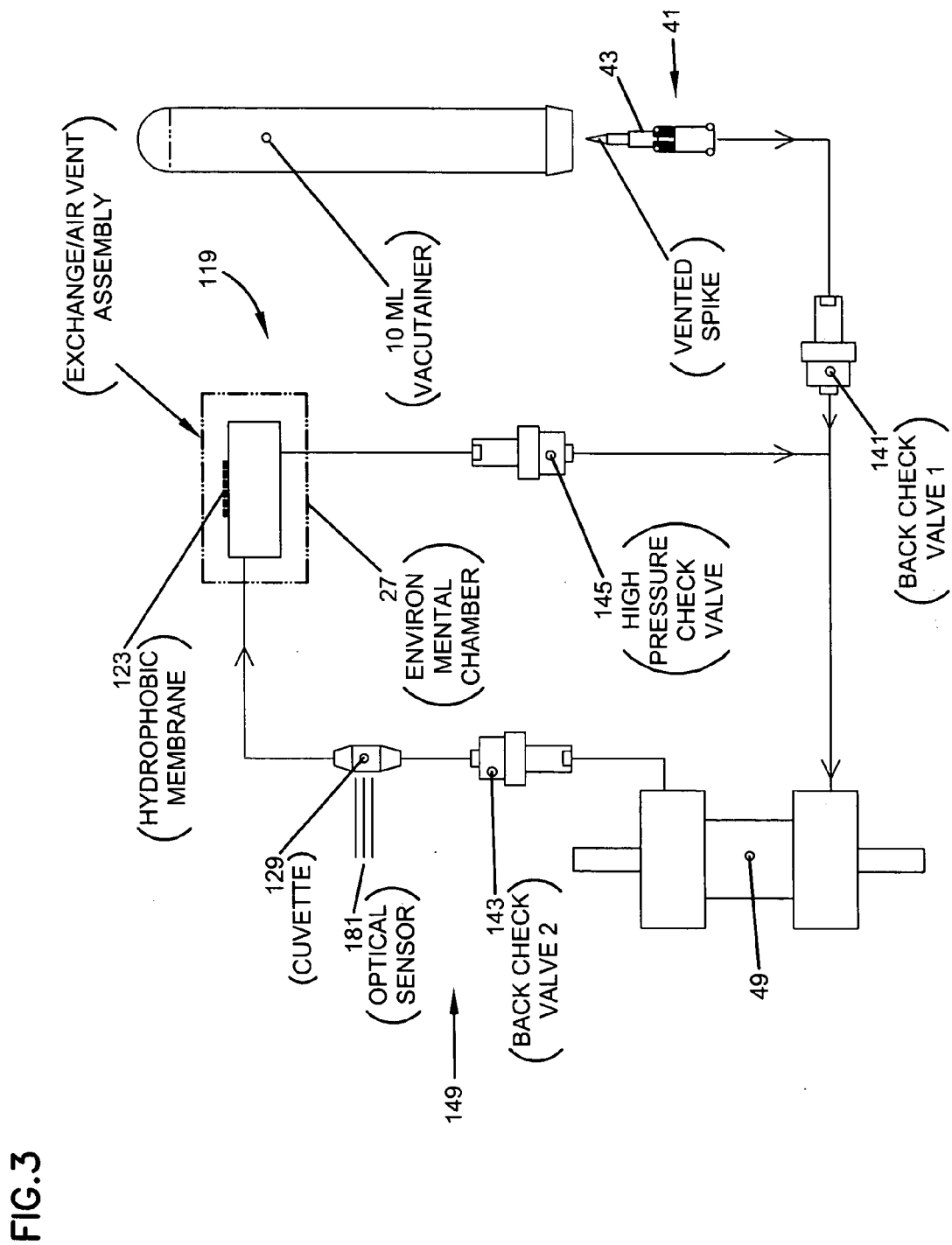
FIG. 3 illustrates schematically a preferred embodiment of an apparatus according to the invention including a schematic diagram of a first fluid circuit.
Figure 4:
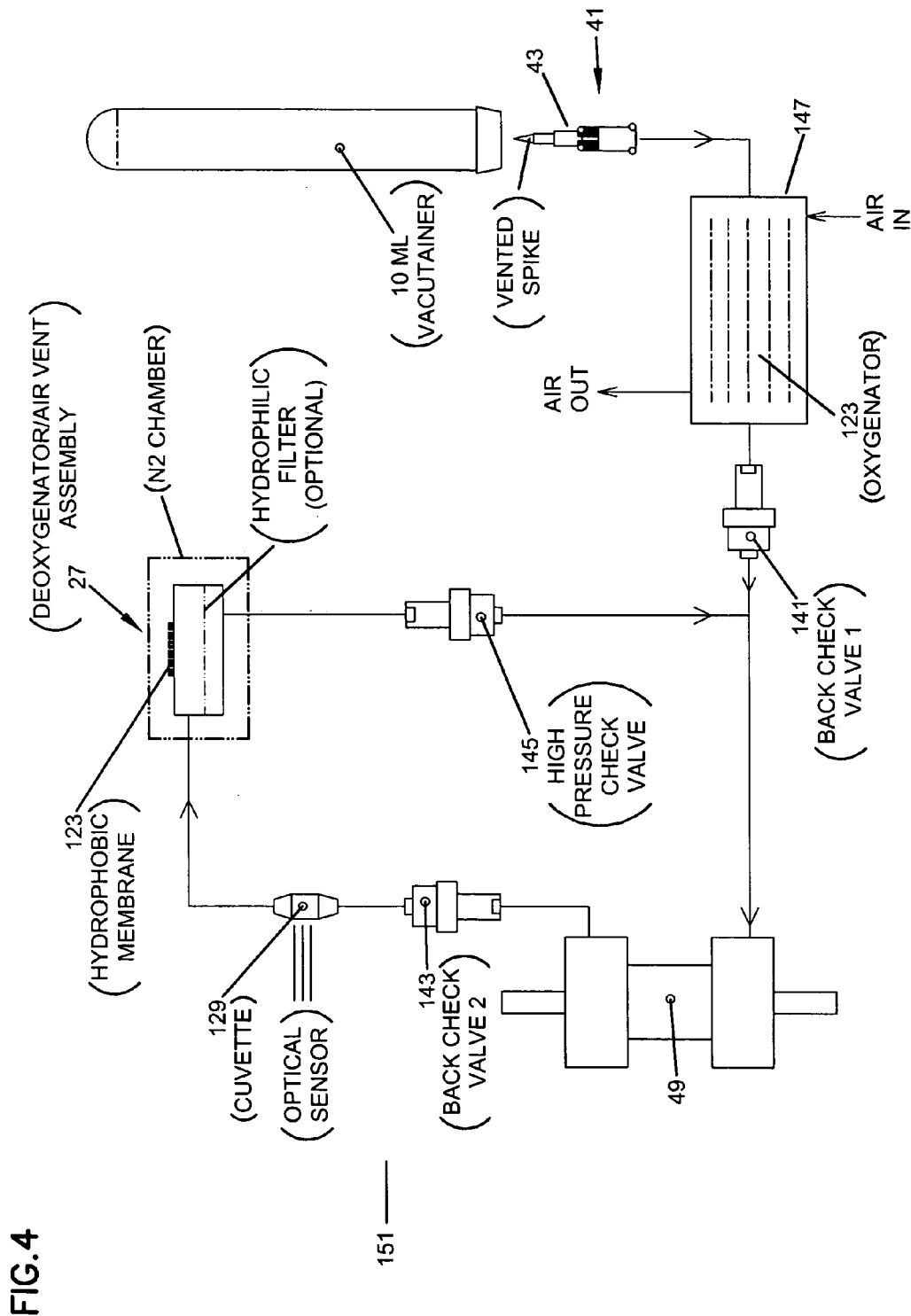
FIG. 4 illustrates schematically another embodiment of an apparatus according to the invention including a schematic diagram of a second the fluid circuit.

FIGS. 3 and 4 illustrate fluid circuits of components forming embodiments of red blood cell transport system 19.

FIG. 3 illustrates first fluid circuit 149. Employing first circuit 149, a container of blood or another fluid containing red blood cells, e.g. a vacutainer, can be pierced by spike 43 of puncture system 41. Reciprocating piston pump 49 then draws the fluid into the system through first check valve 141. Pump 49 pumps the fluid through second check valve 143, cuvette 129, and into contact with hydrophobic microporous membrane 123. From there, the fluid moves is strong through third check valve 145 back to pump 49, and the circuit can be repeated.

FIG. 4 illustrates an alternative embodiment, second fluid circuit 151, of the red blood cell transport system 19. In this embodiment, pump 49 draws blood or another fluid containing red blood cells through puncture system 41 and into an oxygenator 147. Oxygenator 147 brings the red blood cells to their initial oxygen concentration before they enter the circuit. Upon leaving oxygenator 147, the fluid is pulled through first check valve 141 and into pump 49. Pump 49 then pushes the fluid through second check valve 143, cuvette 129 and into contact with hydrophobic microporous membrane 123. From there, the fluid is drawn through third check valve 145 back to pump 49, and the circuit can be repeated.

Modular Transport System

Each of the components described above for red blood cell transport system 19 can be organized as a modular transport system, such as a cartridge-type insert or a cassette, that conveniently couples with a bench or counter top portion of the apparatus. Typically, the modular transport system includes a sampling apparatus, a pump, a diffusion apparatus, and a transparent optical system. The modular transport system is adapted and configured for reversibly coupling to a main body of the apparatus. The bench or counter top portion of the apparatus can include systems such as an apparatus main body, an oxygen level detector 3, a measuring system 33, a gas exchange system 5, an environmental chamber 27, a control system 35, a display system, and the like.

For example, gas permeable tubing 15 may be included in a modular transport system, such as a cartridge-type insert. The cartridge type insert can be easily removed and discarded from the larger portion of the apparatus, after which a new, sterile gas permeable tubing 15 cartridge can be inserted. A removable, and preferably disposable, tubing cartridge increases the testing productivity of the apparatus by drastically decreasing the amount of time lost to cleansing and sterilizing the gas permeable tubing 15 between tests. Further, disposable tubing cartridges decrease the possibility of cross contamination of blood samples, which may lead to inaccurate readings.

In another embodiment, a preferred receiving and diffusion system 31 is adapted and configured as a modular transport system that reversibly couples to the remainder of the apparatus. Advantageously, the modular transport system is constructed and priced to be disposable. For example, such a modular system can reversibly snap or clip into the remainder of the apparatus, fitting similarly to a audio or video cassette into a player. That is, such a modular system can couple both to pump system 29 for pumping fluid through receiving and diffusion system 31, and to measuring system 33 for measuring characteristics (such as oxygen content) of the blood in receiving and diffusion system 31.

Figure 10:
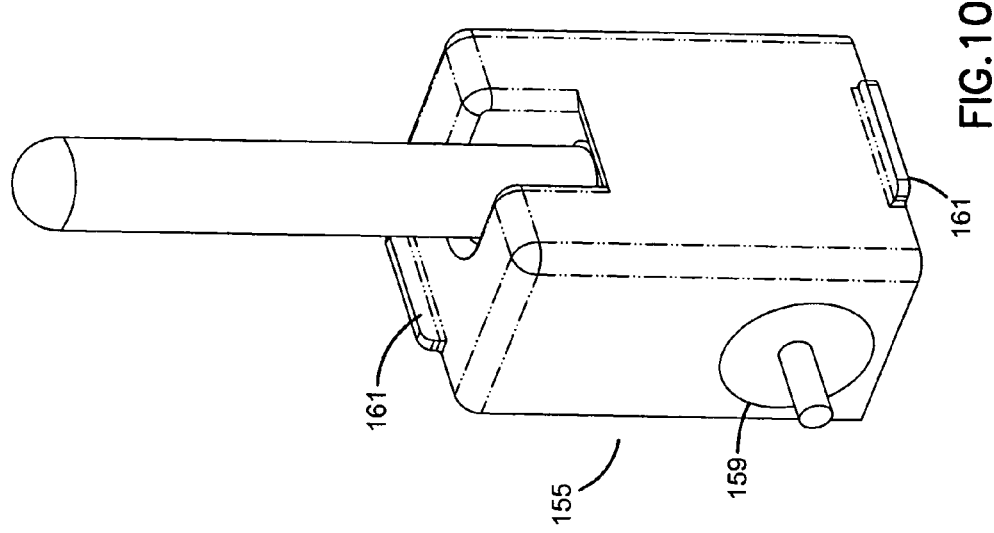
FIG. 10 illustrates a cassette of the present invention having received a container on its puncture system.
Figure 9:
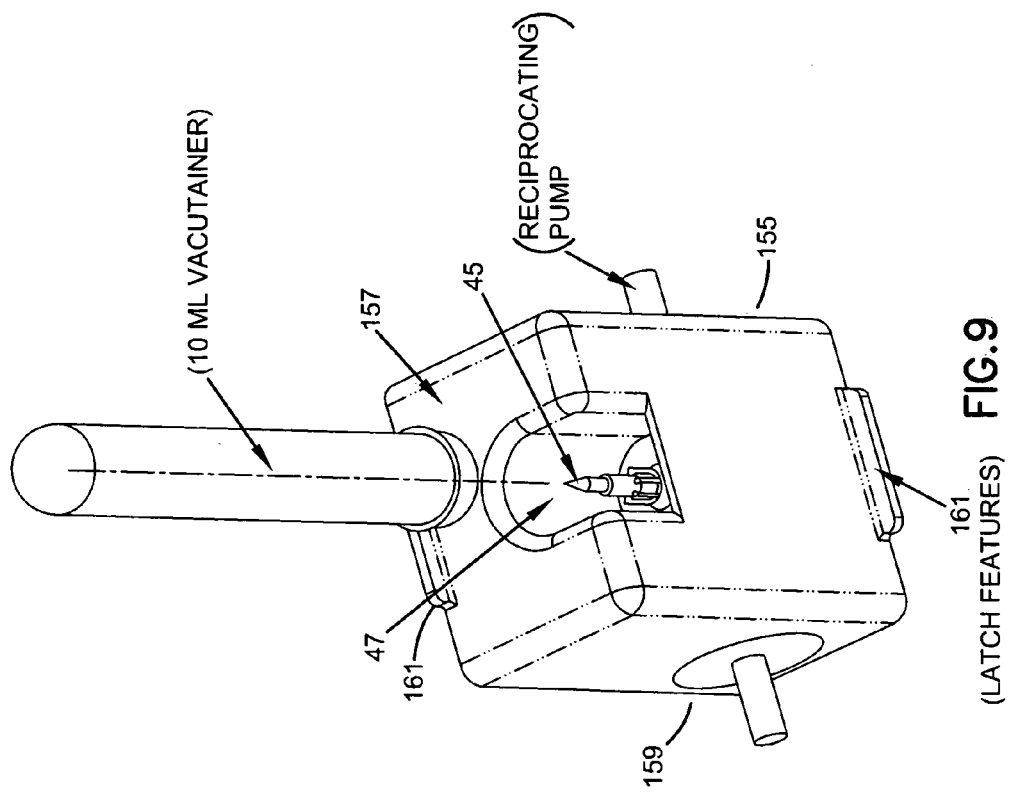
FIG. 9 illustrates a cassette of the present invention and a container that can be received by the puncture system.

In a preferred embodiment, each of the components of first fluid circuit 149 or second fluid circuit 150 can be housed in a modular transport system, such as cassette 155. FIGS. 9 and 10 illustrate an embodiment of cassette 155. Components of cassette 155 are housed by cassette housing 157. Cassette housing 157 defines spike well 47, a pump aperture 159, optical measure window (not shown), and one or more latch tabs 161. Spike well 47 provides a recess that reduces the risk of an operator puncturing their skin on spike 45. Spike well 47 accommodates and can help support a container of blood or another fluid containing red blood cells, e.g. vacutainer 153. FIG. 9 illustrates spike well 47 and spike 45. FIG. 10 illustrates a vacutainer 153 accommodated within spike well 47, and impaled upon spike 45. Preferably, when accommodated by spike well 47, the container of red blood cells is above an oxygenator, if present.

Cassette housing 157 is dimensioned so that at least one end of piston shaft 65 protrudes through pump aperture 159. In addition, pump aperture 159 can mate with pump endcap 61 or 63 to orient and/or retain reciprocating piston pump 49 within cassette 155. Preferably, cassette housing 157 defines to pump apertures 159. In this embodiment, the protruding ends of piston shaft 65 can engage one or more cams 187 on a motor for powering reciprocating piston pump 49. One or more latch tabs 161, or another suitable device, are employed to couple cassette 155 to the remainder of the apparatus.

Preferably, cassette 155 is disposable and reciprocating piston pump 49 and the other components housed by cassette 155 are priced and constructed to be disposable. A disposable cassette 155 preferably minimizes contamination of red blood cell samples, instrument surfaces, the operator, and instruments surroundings. The red blood cell sample remains and circulates within cassette 155 as it is circulated through the chambers and detectors as a rate of oxygen diffusion is measured. At the end of the test, cassette 155 containing the red blood cells is properly disposed of.

Cassette 155 is removable from the remainder of the apparatus, but preferably latches into engagement with the apparatus simply, securely, and readily. This requires that both the pump and the latch portions of cassette 155 simply, securely, and readily engage the apparatus and the motor contained therein. Preferably, piston shaft 65 aligns itself with the motor during engagement without extra manipulation on the part of the operator. Preferably, proper engagement of cassette 155 with the instrument results in visual, tactile, or audible feedback that confirms engagement of cassette 155. Cassette 155 can be adapted and configured to be removable by a simple, continuous motion, such as squeezing.

Preferably employing cassette 155, it is engaged with or put into the remainder of the apparatus before engaging the vacutainer or other container of red blood cells. Engaging cassette 155 with the instrument and container e.g. vacutainer 153, with the cassette can automatically began drawing blood from the container into the cassette 155. Alternatively, the operator can initiate loading of the cassette. A preferred cassette will be fully loaded with 5 ml or less of fluid.

Interfaces

Red blood cell transport system 19 includes any sensors, transducers, devices, or systems suitable for coupling to or communicating with the remainder of the apparatus. For example, red blood cell transport system typically includes components necessary for monitoring and recording flow rates and like characteristics as a function of time.

A preferred pump 21, e.g. pump system 29, includes a control system 35 that can interface with automated (e.g. PC based) laboratory data acquisition and control systems, such as a PC Labview system, or other internal or external automated systems as required to control, calibrate, or validate pump 21, e.g. pump system 29.

Gas Exchange System

The apparatus employs a gas handling system, such as a gas exchange system 5, environmental chamber 27, and/or sample receiving and diffusion system 31 to expose a red blood cell sample to various environments of gas content, humidity, and/or temperature. A gas handling system subjects the red blood cell to conditions where oxygen will diffuse across the cell membrane. The gas handling system operates cooperatively with the red blood cell transport system 19, and certain of its components, to achieve a measurable rate of oxygen diffusion across a red blood cell membrane.

Gas exchange system 5 typically includes a source of gas (not shown), a gas inlet 7, a gas outlet 9, a housing 11 that defines a chamber 13, and a gas permeable tubing 15. These components are typically assembled as a closed circuit diffusion system 17. Gas permeable tubing 15 has a lumen (not shown) that is used to contain, preferably flowing, fluid containing red blood cells. A preferred fluid containing red blood cells is blood that has been treated with an anticoagulant. Gas permeable tubing 15 is constructed to allow diffusion of gasses from chamber 13 into the lumen and into any fluid in the lumen and can be made of silicone or silastic material. Gas permeable tubing 15 may be a component of a cartridge-type insert, such as cassette 155, which can be easily removed and discarded, after which a new cartridge-type insert including sterile gas permeable tubing 15 can be inserted. A removable, and preferably disposable, tubing cartridge insert increases the testing productivity of the apparatus by decreasing the amount of time lost to cleaning and sterilizing the gas permeable tubing 15 between tests. Further, a disposable tubing cartridge insert decreases the possibility of cross contamination of blood samples, which may lead to inaccurate readings.

Gas is introduced into chamber 13 through gas inlet 7, and exits through gas outlet 9. Preferably, gas flows through chamber 13 to remove any gas that diffuses from gas permeable tubing 15 and to replace any gas the diffuses into gas permeable tubing 15. Housing 11 can be a stoppered laboratory flask, such as an Erlenmeyer flask. Gas exchange system 5 can be any of several suitable systems for exchanging gas into red blood cells, blood, or another fluid.

Chamber 13 or environmental chamber 27 can be any suitable configuration for containing a, preferably flowing, defined gas atmosphere. Preferably, housing 11 or environmental chamber 27 is adapted and configured to expose gas permeable tubing 15, diffusion apparatus 119, and/or hydrophobic microporous membrane 123 to a flowing defined gas atmosphere. As described above, housing 11 can be any of a variety of vessels, suitable for containing a flowing, defined gas atmosphere. In an embodiment in which gas permeable tubing 15 or hydrophobic microporous membrane 123 is a component of a cartridge-type insert, a modular system, or cassette 155, housing 11 or environmental chamber 27 is adapted and configured to defined chamber 13 in cooperation with the insert, module, or cassette 155. For example, a portion of cassette 155 including hydrophobic microporous membrane 123 can be inserted into or be sealingly contacted with housing 11 to define chamber 13 or environmental chamber 27. Preferably, gas inlet 7 and gas outlet 9 are components of the body of the apparatus rather than of cassette 155. For example, main body 183 and/or housing 11 of the apparatus can be in fluid communication with a tank of air, oxygen, or nitrogen and can be adapted and configured with valves or other apparatus to control the flow of these gases into chamber 13 or environmental chamber 27.

A preferred gas exchange system includes chamber 13 or environmental chamber 27 and certain components of sample receiving and diffusion system 31, which together are adapted and configured for exchanging gas into red blood cells, blood, or another fluid. A preferred environmental chamber 27 can cycle under one or more of the following sets of conditions. For example, at the start of the measurement the chamber houses an oxygen atmosphere at a concentration and in a configuration capable of increasing the $S_{O2}$ of an about 5 to about 10 ml blood sample in the sample receiving and diffusion system 31 to above about 97.5% in no more than about 1 minute. For a measurement under normal conditions, the chamber houses an atmosphere of $pO_2$ (about 40 mm Hg) in a configuration capable of decreasing $S_{O2}$ of an about ten ml blood sample in the sample receiving and diffusion system 31 to about 75% or less in a short time. For a measurement under maximum stress conditions, the chamber houses an atmosphere of $pO^2$ (about 20 mm Hg) in a configuration capable of decreasing $SO_2$ of a ten ml blood sample in the sample receiving and diffusion system 31 to about 40% or less in a short time. In this context a short time is less than about 20 min, preferably less than about 6 min, preferably less than about 2 min.

Fluid containing red blood cells can be transported in a and the various components of red blood cell transport apparatus 19 can be coupled by tubing, fittings, connectors, and the like known to those of skill in the art for transporting fluids containing red blood cells. For example, FIG. 1 illustrates an apparatus in which each of the components of red blood cell transport system 19, and the other components of the apparatus, are coupled by tubing, through which the red blood cells flow. FIGS. 3 and 4 illustrate embodiments of the apparatus in which the fluid circuit can be made from the various components connected by tubing, by couplings, or even embedded in a solid material with channels in the solid material forming passages through which the fluid containing red blood cells flows. Preferred fittings are made from an inert plastic such as polyterfluoroethylene, polypropylene, and the like.

Oxygen Level Detector

The apparatus employs an oxygen level detector 3 such as measuring system 33 to determine the level of oxygen in a fluid containing red blood cells. Oxygen level detector 3 or measuring system 33 can detect oxygen present as oxygen bound to hemoglobin or oxygen in the fluid surrounding the red blood cells, such as a plasma oxygen. Oxygen level detector 3 or measuring system 33 can employ any of a variety of known electrochemical or light-based methods for detecting oxygen.

Oxygen level detector 3 can be any of several detectors suitable for detecting oxygen levels in plasma or another fluid and/or for detecting oxygenated hemoglobin or another oxygen complex. For example, oxygen detector 3 can include an oxygen electrode, a spectrophotometric detector, a fluorometric detector, or a combination of such electrodes and/or detectors. Preferably, oxygen level detector 3 includes detectors for spectrophotometric determination of oxygenated hemoglobin. Preferably in one embodiment, oxygen level detector 3 is a dual or multiple wavelength spectrophotometer.

In one embodiment, oxygen level detector 3 includes: a light source capable of producing light of 385 nm, 660 nm, 805 nm and an absorption free wavelength; one or more filters to sequentially submit a blood sample to these wavelengths; a cell to allow blood to flow through this light system; and photopickups to detect the transmission of light through the sample at each wavelength. Preferably, oxygen level detector 3 is coupled to appropriate electronics and microprocessors to derive the amounts of, or changes in amounts of, plasma oxygen and/or oxygenated hemoglobin from the comparative signals.

A preferred oxygen level detector 3 or measuring system 33 is adapted and configured for taking measurements of oxygen levels that yield both oxygen saturation and hematocrit. This can be accomplished by a measuring system including three light emitting diodes (LEDs) and a sensor. A first LED emits at about 650 nm (referred to as $I_{red}$), which can be absorbed strongly by deoxygenated hemoglobin. A second LED emits in the infrared range at about 805 nm and is referred to as $I_{irnear}$. A third LED also emits in the infrared range at about 805 nm and is referred to as $I_{irfar}$. The wavelengths emitted by the second and third LEDs are equally absorbed by oxygenated and deoxygenated hemoglobin (the isobestic wavelength). The ratio Of $(I_{red}/I_{irnear})$ gives the oxygen saturation and the ratio of $(I_{irnear}/I_{irfar})$ gives a signal proportional to the hematocrit. The signals can be separated, i.e. $SO_2$ and hematocrit are independent. However, there is some non-linearity so the apparatus preferably generates a calibration and a "look up table".

Figure 11:
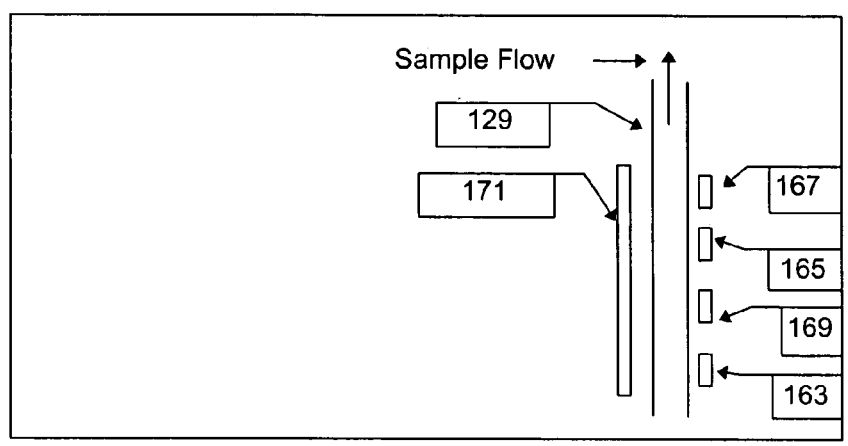
FIG. 11 illustrates an embodiment of an oxygen level detector of the present invention; this oxygen level detectors configured for sequential measurement of $SO_2$ and hematocrit.

FIG. 11 illustrates an embodiment of measuring system 33 including the three LEDs. The Figure illustrates sample flowing through cuvette 129 presenting transparent faces to each of the first, second, and third LEDs (163, 165, and 167), detector 169, and reflector 171. As described above, first LED 163 emits at about 650 nm, and second and third LEDs, 165 and 167, each emit at 805 nm. Second LED 165 is the near infrared LED and third LED 167 is the far infrared LED. In this embodiment, the light emitted by first, second, and third LEDs, 163, 165, and 167, passes through a transparent wall of cuvette 129, through the fluid containing red blood cells, and through a second transparent wall of cuvette 129. The light then impinges upon and is reflected by reflector 171. The reflected light can be detected by detector 169. The detector can be a photoelectric detector, which then transmits a signal to a processor or control system for detecting the level of hemoglobin bound oxygen, hematocrit, and like parameters.

A preferred oxygen level detector 3, such as measuring system 33, can monitor $SO_2$, preferably noninvasively. Advantageously, a measuring system 33 can monitor the $pO^2$ of the gas mixture over a range sufficient to provide the diffusion conditions described above. For example, the range of $pO_2$ is advantageously from about 100 mm Hg to about 20 mm Hg. Advantageously, a measuring system 33 can monitor the $S_{O2}$ of a blood, or other, sample over a range sufficient to provide the diffusion conditions described above. For example, the range of $S_{O2}$ is advantageously from about 100% to about 40%, or less.

Advantageously, each measurement is made with accuracy and reproducibility sufficient to aid in the diagnosis, treatment, and study of diseases and disorders that affect oxygen release or uptake. Such diseases and disorders include heart disease, pulmonary disease, peripheral vascular disease, a disease or disorder of endothelial function, a disease or disorder of the release of transmitters, a combination thereof, and the like. The method preferably makes measurements with sufficient accuracy and reproducibility for detecting alterations in cholesterol levels produced by therapy such as diet or medicine, detecting alterations in the ability of red blood cells to deliver oxygen to the heart, detecting alterations in the ability of red blood cells to pick up oxygen to the lungs, and the like.

Preferably, measuring system 33 can measure $S_{O2}$ or $pO_2$ with a frequency suitable for making simple two point comparisons of values, or for measuring a timecourse of oxygen release or uptake. Measuring system 33 can take a measurement in response to the operator, according to a predetermined program for measurement, by a combination of such procedures, and the like. Advantageously, a measuring system 33 can measure $SO_2$ at least once each 15 seconds in a predetermined program. Preferably, measuring system 33 is adapted and configured for providing a signal communicating the measurement and any associated information to a processor or computer for control and data gathering.

Measuring system 33 can advantageously be calibrated to assure accuracy and precision of measurements of oxygen amounts. For example, a standard solution can be place in position for measurement. The standard solution can be in a specialized calibration module, such as a receiving and diffusion system 31 adapted to contain a standard solution and, advantageously, to communicate to the apparatus that a calibration standard is in the apparatus. Alternatively, a one or more standard solutions can be sequentially added to a typical receiving and diffusion system 31 and the system can be calibrated according to the solution in the system.

Control System

Once the $SO_2$ or $PO_2$ rate is determined, the apparatus records and/or displays the value. The apparatus may be configured to provide a final rate, a rate at a determined time period, or an average rate. For some tests it may be desirable for the apparatus to provide a continuous rate display or a graphical representation of the rate over time.

The apparatus can be controlled by employing a control system 35 that, for example, controls calibration, display, mechanical actions (e.g. pumping), and measurement by the apparatus. Control system 35 can be manipulated by the operator and/or by a predetermined program to, for example, calibrate the apparatus, monitor that the apparatus is within calibration, start and stop pump system 29 and any other mechanical or electrical systems of the apparatus, recognize a properly inserted receiving and diffusion system 31, and control and communicate with the measurement system.

Control system 35 can incorporate a processor 37 for displaying and performing analysis of measurements taken by the apparatus. For example, advantageously, control system 35 can gather $S_{O2}$ measurement data at least about each 15 seconds and then plot natural log $S_{O2}$ against time. From such data, a preferred control system 35 can calculate the slope of the plot which represents permeability of red blood cells. Advantageously control system 35 includes data retention apparatus 39 that provides for statistical analysis of any measurements and data, entry of additional patient or clinical information either by the operator or another processor, and the like. Such information can include a hematocrit, a cholesterol level, and the like. A preferred control system 35 can display the information and test or measurement data either as a table or graph, and provide output suitable for screen display or printing. Control system 35 can include a display 193 and/or printer 191 suitable for display and/or printing and one or more data ports 197 suitable for communication of data to and from control system 35. Control system 35 can also include a key pad 195 for entry information.

Advantageously control system 35, preferably employing data retention apparatus 39, can store, by methods standard in the data processing arts, patient data either to internal memory or to remote memory and then correlate patient data from a test with patient data from other, typically previous, tests on the same patient. Alternatively, control system 35 can access a database of population data for patient populations similar to or contrasting with the current patient, and conduct comparison of the current patient data with the population data.

Figure 12:
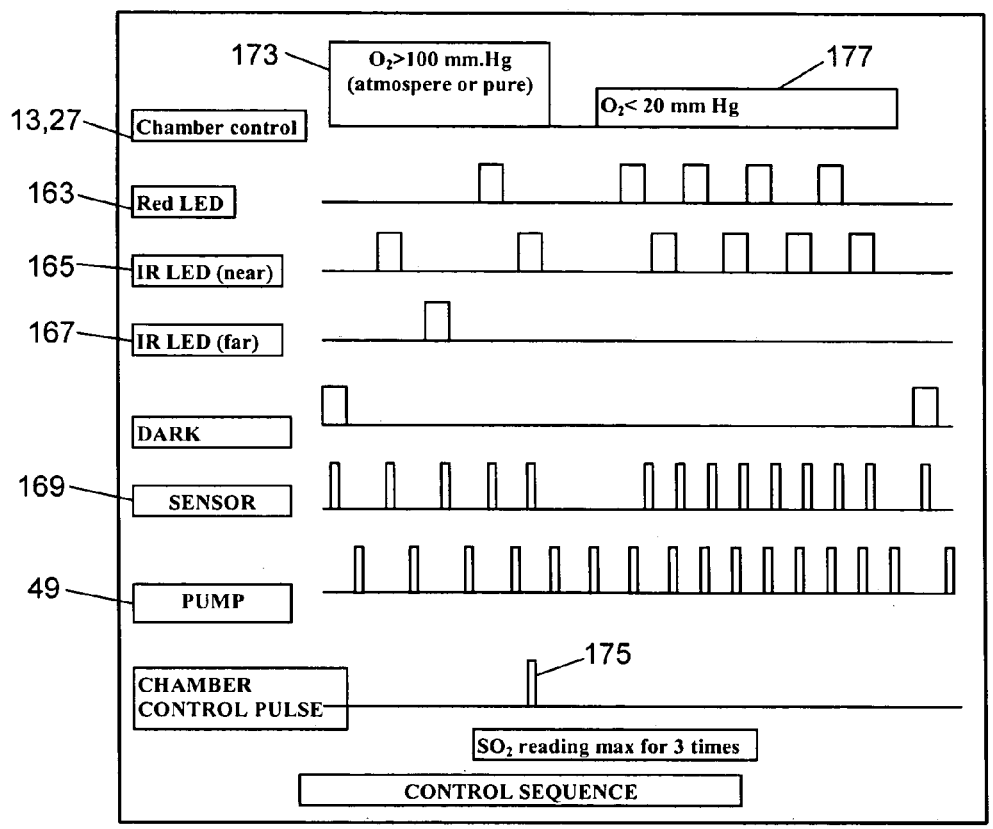
FIG. 12 illustrates control sequences for an oxygen level detector, a gas exchange system, and a red blood cell transport system according to the present invention.

FIG. 12 illustrates a control sequence for the pump, sensors, LEDs, and environmental chamber. Such a control sequence can be developed in applying commercially available software for controlling laboratory apparatus (Labview, National Instruments, Dallas, Tex.) and embodied in the apparatus of the invention as either software or hardware. For example, a control sequence can be embodied in a commercially available PIC microprocessor board. In employing an apparatus embodying this control sequence, a sample is first introduced into cassette 155 and cassette 155 is inserted into the rest of the apparatus. Control pulses to reciprocating piston pump 49 start the fluid containing red blood cells circulating through red blood cell transport apparatus 19, introduce an oxygen rich atmosphere into chamber 13 or oxygenation pulse box 173, test for maximum oxygenation of the sample, evacuate chamber 13 and introduce the oxygen depleted atmosphere, initiate sequential SO$_2$ measurements, and initiate data gathering and storage.

Preferably, any dissolved air is removed from the sample and the sample is oxygenated to up to about 100% oxygen saturation. The duration of oxygenation is illustrated by oxygenation pulse box 173. During the oxygenation procedure first LED 163, second LED 165, third LED 167, and detector 169 can be activated to take readings useful for purposes including determining whether oxygenation is complete and providing a baseline level for oxygen saturation and hematocrit. FIG. 12 illustrates sequences useful for these purposes. Once oxygenation is complete, control chamber pulse 175 activates gas exchange system 5 for changing the oxygen concentration in chamber 13 or environmental chamber 27. In the example illustrated in FIG. 12, the duration of exposure to low concentrations of oxygen, or deoxygenation, is shown by deoxygenation pulse 177. During the deoxygenation procedure first LED 163, second LED 165, third LED 167 and detector or 169 can be activated to take readings useful for purposes including determining a rate at which oxygen diffuses across the red blood cell membrane, determining oxygen saturation, determining hematocrit, and the like. During the deoxygenation phase, reciprocating piston pump 49 and the detector 169 are pulsed more frequently than during the oxygenation phase. An analogous control sequence can be employed with a deoxygenation phase preceding oxygenation. The system can also undertake quality control checks, such as checking for adequate seating of the cassette, acceptable dark current and sensitivity of the sensor, acceptable oxygenation and deoxygenation times, and adequate signal level.

The rate of oxygen diffusion across the membrane of a red blood cell can be derived from the data obtained during the control sequence by, for example, fitting relative values of SO$_2$ to an exponential curve of the form of Equation A below $$y = e^{-a \cdot t} : y = \text{ratio of } SO_2 \text{ at time } 't' \text{ to initial } SO_2 \quad \text{Equation A}$$

The constant "a" in this equation represents a rate constant for oxygen diffusion. The value determined by fitting to equation 1, and any data values of SO$_2$ can be displayed on a display system of the apparatus. In addition, the control system can, in certain embodiments, perform quality control checks on the data.

Operating Environment

Figure 20:
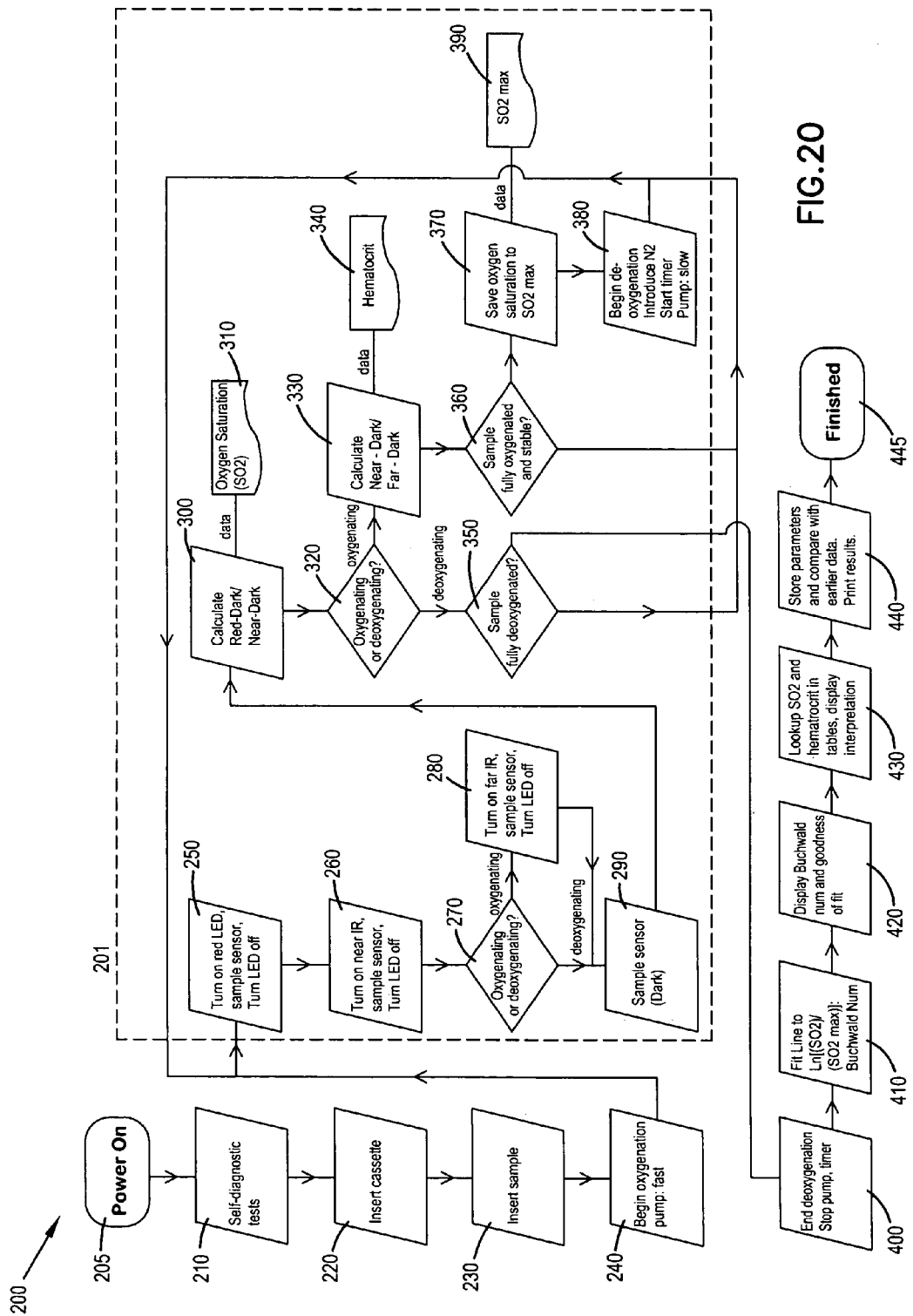
FIG. 20 illustrates one embodiment of an operating environment in wbkh the present invention can be implemented.

FIG. 20 illustrates an example of a suitable operating environment 200 in which the invention can be implemented. The operating environment 200 is only one example of a suitable operating environment and is not intended to suggest any limitation as to scope of use or functionality of the invention. Other well known computing systems, environments, and/or configurations may be suitable for use with the invention.

The invention can be described in the context of computer executable instructions, such as control blocks, executed by one or more computers or other devices. Generally, control blocks include routines, programs, objects, components, data structures, etc. that perform particular tasks or implement particular abstract data types. Typically the functionality of the program modules can be combined or distributed as desired in various embodiments.

FIG. 20 illustrates operating environment 200 for a particular embodiment of the present invention. FIG. 20 includes control blocks 205–445 that can be implemented using hardware contained within the apparatus of the invention or software processed by a computing device. The computing device can be designed as an integral component of the apparatus of the invention or can be designed as a separate component. One skilled in the art would understand that a particular control block illustrated in FIG. 20 could be implemented in hardware or software without departing from the scope of this invention.

Control block 205 initiates the operating environment 200 during power on for both the main body of the apparatus 183 used to manipulate a sample, such as a blood sample, as well as the computing device used to implement software instructions and process and store data. Diagnostic tests are performed in 210, which includes various self-calibration and error checking routines for the apparatus 183 and computing device.

In the next control block 220, a cassette 155 is inserted into the apparatus 183. Cassette 155, as part of the modular transport system, couples with the main portion of the apparatus 183 and can include a sampling apparatus 117, a pumping apparatus 29, a diffusion apparatus 119, and a transparent optical system 121. Control block 220 can monitor insertion of the cassette 155 and provide feedback to the user if the cassette is inserted incorrectly. With cassette 155 inserted, control block 220 can provide a signal indicating that apparatus 183 is ready to perform an analysis of a sample as provided in control block 230.

In the next control block 230, the sample is inserted into the apparatus 183. The sample can be inserted into the apparatus 183 by, for example, one of the various methods described above under the Red Blood Cell Transport System heading. After the sample is inserted using the desired method of insertion, control block 230 passes control to block 240 to allow apparatus 183 to commence analysis of the sample.

The sample is moved throughout the apparatus 183 by the modular transport system. Control of the pump 21 can be implemented using either circuitry maintained within apparatus 183 or through control by the computing device. The sample is initially moved throughout apparatus 183 by the pump 21 to oxygenate the sample. Once the oxygenation cycle is complete, the sample is deoxygenated. At different points throughout the process the oxygen levels within the sample are measured.

In 240 the sample is drawn into the modular transport system and pumped throughout apparatus 183 at a high flow rate during oxygenation.

Control blocks 250–390 make up the analysis phase 201 of the operating system 200. In the analysis phase 201, the sample is pumped throughout apparatus 183 as various tests and data are collected.

Control blocks 250–280 operate to control the transparent optical system 121 and include LEDs used to detect oxygen levels within the sample. Control of these LEDs can be implemented using circuitry contained within the apparatus 183 or software instructions processed by the computing device. In 250, a red LED 163 is activated, a detector 169 detects light passing through the sample, and the LED is turned off. In 260, a first infrared LED 165 is activated, the detector 169 detects light passing through the sample, and the infrared LED is turned off. Control block 270 then determines whether apparatus 183 is oxygenating or deoxygenating the sample. If apparatus 183 is in oxygenating mode, a second infrared LED 167 is activated, the detector 169 detects the light passing through the sample, and the LED is turned off. Data from the detector 169 readings performed in control blocks 250, 260 and 280 can be stored and manipulated by the computing device.

In control block 290, the detector 169 takes a dark sample reading with all LEDs turned off. This dark reading can be used as a reference value for calculations performed in blocks 300 and 330.

Control blocks 300–340 process the data received from the detector 169 in blocks 250, 260 and 280. The computing device calculates oxygen saturation and hemocrit. In 300, the computing device calculates the red minus dark divided by near minus dark calculations and computes an oxygen saturation (SO2), as shown in 310. In decision control block 320, if the apparatus 183 is deoxygenating the sample, further decision control block 350 determines whether the sample is fully deoxygenated or not. If the sample is fully deoxygenated, control is passed to block 400. Otherwise control is passed back to control block 250 and analysis phase 201 begins again.

If control block 320 determines that the sample is being oxygenated, then the computing device makes the near minus dark divided by far minus dark calculation for determining a hemocrit as shown in control blocks 330 and 340. Next, in decision control block 360 it is determined whether the sample is fully oxygenated and stable. If the sample is not fully oxygenated and stable, control is passed back to control block 250 and analysis phase 201 begins again. If, however, it is determined that the sample is fully oxygenated and stable, in 370 the computing device records the oxygen saturation level as the SO2 max, as shown in control block 390. Then deoxygenation is started in 380. $N_2$ is introduced into apparatus 183, a timer is started, and the pump rate is slowed. Control from 380 is then passed back to control block 250 to begin analysis phase 201 again.

If a sample is fully deoxygenated as determined by decision control block 350, the pump 21 and timer are stopped as shown in control block 400 and deoxygenation ends. In control blocks 410–440, the computing device performs calculations based on the data gathered by the detector 169 of apparatus 183. In 410, calculations are performed to fit the data to a plot of ln(SO2)/SO2 max) against time and calculate the Buchwald number used to describe the rate of oxygen diffusion across the blood cell membrane.

In 420 the computing device can display the Buchwald number and a statistical analysis of the fit of the observed data points compared to the calculated curve. In 430 the computing device can look up SO2 and hemocrit data and display this information. Finally, all parameters can be stored by the computing device and compared with earlier data as shown in 440. The results of this comparison can be displayed, stored, printed out in hard copy form, or otherwise communicated. Control block 445 completes data manipulation and display.

The computing device can also be used to perform any number of other calculations based on the data provided by apparatus 183. The computing device can calculate and display plots of different data readings, provide a statistical analysis of the measurements, allow for the entry of additional patient information, and perform other calculations. The computing device can display continuous or historical data and can modify control of apparatus 183 based on the data gathered. The computing device can also calculate and display desired values such as the rate at which oxygen departs or enters the red blood cell. These illustrations are provided to show the versatility that can be achieved using the computing device and are not meant as limitations.

The operating environment 200 has been described as a series of control blocks 205–445. It should be understood that the sequence of the blocks as provided in this embodiment are for illustrative purposes only, and deviations from the sequence of these blocks can be made without departing from the spirit of this invention. Particularly, the blocks provided in analysis phase 201 can be altered or their sequence changed. For example, hemocrit calculations performed in control blocks 330–340 can be performed before oxygen saturations calculations in control blocks 300–310.

Main Body of the Apparatus

Figure 13:
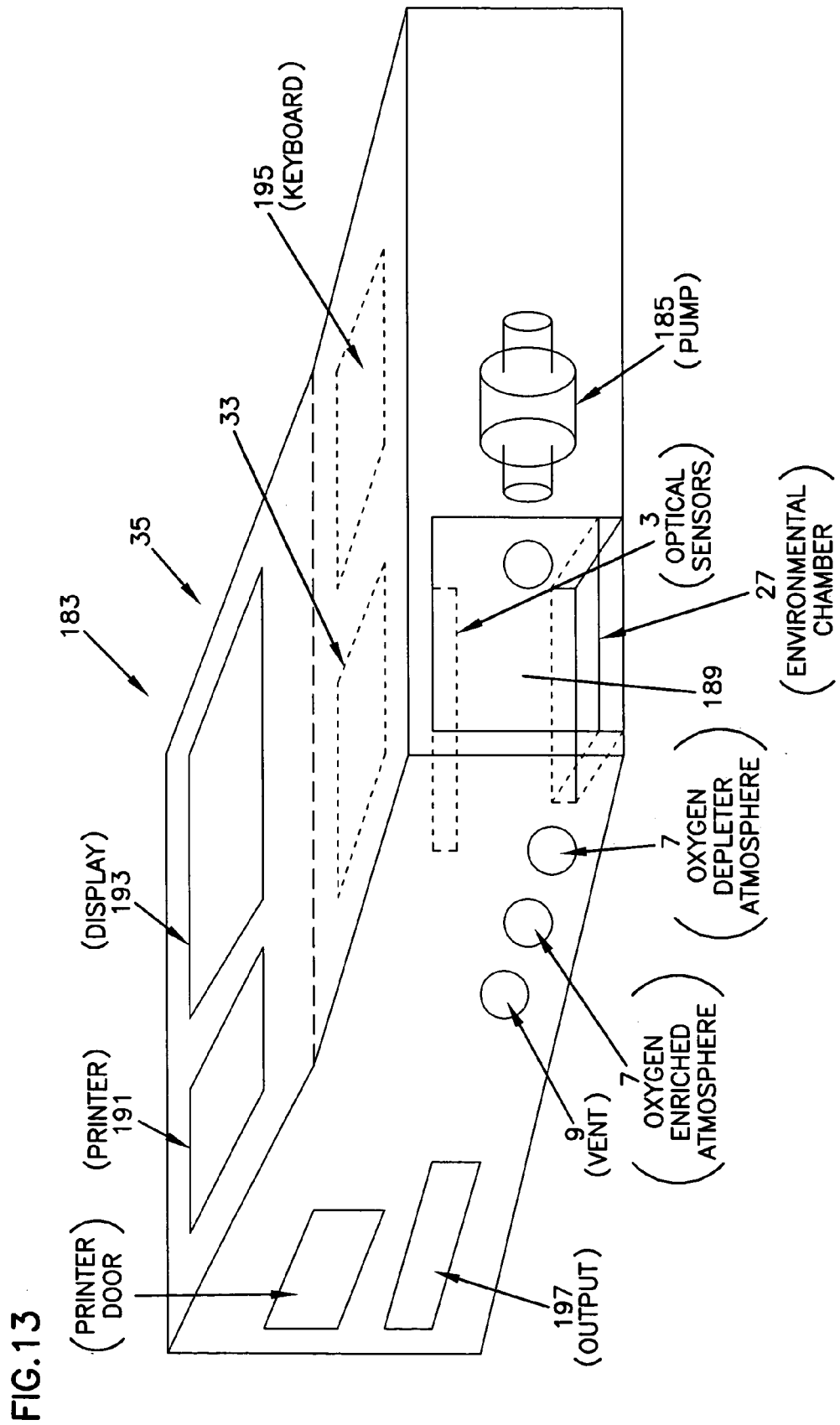
FIG. 13 illustrates an embodiment of a main body of the apparatus.

In a preferred embodiment, the modular transport system couples with a main body 183 of the apparatus (FIG. 13). Main body 183 of the apparatus can, for example, be a portion of the apparatus that remains on a bench or counter top. Alternatively, main body 183 can be portable. Main body 183 is a lasting and reusable portion of the apparatus. Modular transport system, in contrast to main body 183, is typically constructed and priced to be disposable. Main body 183 can include components of the apparatus such as gas inlet 7, gas outlet 9, housing 11, a pump motor 185, measuring system 33, control system 35, and any display systems. Main body 183 also defines one or more spaces or cavities including a portion of environmental chamber 27 and a cavity for receiving a modular transport system, such as cassette 155.

Typically, gas exchange system 5 includes components of main body 183 such as gas inlet 7 gas solenoid 5 and those portions of main body 183 housing 11 that define environmental chamber 27. The portion of main body 183 that defines environmental chamber 27 is adapted and configured for coupling with the portion of red blood cell transport system 19 that carries blood into chamber 13 or environmental chamber 27 and which provides for contact between gas and fluid. For example, main body 183 and diffusion apparatus 11 when there 7 can couple and cooperate to form environmental chamber 27. The environmental chamber thus formed is adapted and configured to retain a gas mixture in contact with a membrane, such as hydrophobic microporous membrane 123, of diffusion apparatus 117.

Typically, red blood cell transport system 19 includes pump 19 and pump motor 185. Pump motor 185 is adapted and configured for coupling to and driving pump 19. For example, when pump 19 is a reciprocating piston pump 49, pump motor 185 can include one or more cams 187 adapted and configured to reciprocatingly drive reciprocating piston 85.

Typically, oxygen level detector 3 includes measuring system 33 and transparent optical system with 121. Measuring system 33 is adapted and configured for directing light upon transparent optical system 121. For example, transparent optical system 121 can include cuvette 129 positioned with reflector 171 on one side and LEDs 163, 165, and 167 and detector 169 on the other side.

Illustrated Embodiments

FIG. 1 illustrates an embodiment of the apparatus according to the invention that can operate as follows. A fluid containing red blood cells can be introduced into, preferably, inflow tubing 23. Then, this fluid can be transported into closed circuit diffusion system 17 by red blood cell transport system 19, specifically pump 21. Inflow tubing 23 is typically coupled to gas permeable tubing 15 which enters or is in chamber 13. Within chamber 13, the fluid is exposed to a selected gas environment, which either oxygenates or deoxygenates the fluid sample and the red blood cells it contains. The environment within chamber 13 is defined by gas which enters through gas inlet 7 and leaves through gas outlet 9. The fluid flows through gas permeable tubing 15, gasses are exchange with the gasses in the chamber 13, and the fluid flows out and into outflow tubing 25. One or more detectors can be positioned to monitor the fluid as it travels through either inflow tubing 23 or outflow tubing 25. For example, oxygen level detector 3 can be coupled to either inflow tubing 23 or outflow tubing 25 in a manner such that an oxygen electrode, a spectrophotometric detector, a fluorometric detector or another type of detector can measure the oxygen level within the red blood cell, or within the plasma or other fluid surrounding the red blood cell. A secondary detector 179 can also be coupled to either inflow tubing 23 or outflow tubing 25 such a secondary detector 179 can measure the partial pressure of oxygen, the partial pressure of carbon dioxide, or pH. Each of red blood cell transport system 19, oxygen level detector 3, and secondary detector 179 can be coupled to appropriate electronics or microprocessors for recording, calculating, and displaying desired values, such as a rate at which oxygen departs or enters the red blood cell, and the like.

FIGS. 2A and 2B present schematic illustrations of another embodiment of an apparatus according to the present invention that can operate as follows. A fluid containing red blood cells is added into the disposable sampling module portion of sample receiving and diffusion system 31. Pumping mechanism portion of pump system 29 circulates the fluid through the diffusion tubing portion and transparent optical coupling portion of sample receiving and diffusion system 31. Diffusion tubing portion of sample receiving and diffusion system 31 interacts with environmental chamber 27 to expose the fluid to an appropriate concentration of oxygen for either oxygenating or deoxygenating the fluid sample containing red blood cells. The transparent optical portion of sample receiving and diffusion system 31 interacts with measuring system 33 for determining values such as oxygen saturation, a hematocrit, and oxygen bound to hemoglobin. These values are then communicated to control system 35 including processor 37 and data retention apparatus 39. Control system 35 can, thus, calculate and display relevant values, such as the rate at which oxygen enters or departs a red blood cell.

FIG. 3 illustrates yet another embodiment of the apparatus of the invention that can operate as follows. A container, such as a vacutainer, containing fluid with red blood cells can be impaled on spike 43. Reciprocating piston pump 49 draws fluid into a fluid circuit through first check valve 141. Fluid circuit is composed of components such as one or more valves, pumps, membranes, cuvettes, or the like coupled for fluid flow by tubing, connectors, or other apparatus suitable for fluid flow between these various components. The fluid passes through reciprocating piston pump 49 and through second check valve 143. The fluid then enters cuvette 129, which is optically coupled to optical sensor 181. Optical sensor 181 include sensors that can measure oxygen saturation of hemoglobin, hematocrit, plasma oxygen concentration, or other relevant parameters. The fluid flows through cuvette 129 and then along or in contact with hydrophobic microporous membrane 123 and diffusion apparatus 119. Diffusion apparatus 119 includes environmental chamber 27 in which the fluid sample is exposed to different gaseous atmospheres to either oxygenate or deoxygenate the fluid. The fluid continues through third check valve 145 into the pump and to optical sensor 181. Optical sensor 181 can then measure relevant characteristics of the oxygenated or deoxygenated fluid. The data gathered by optical sensor 181 can then be sent to control system 35 for processing as described above.

FIG. 4 illustrates a variation of the apparatus shown in FIG. 3. This variation operates only slightly differently than the embodiment shown in FIG. 3. Specifically, fluid from a container, such as a vacutainer, that contains red blood cells is drawn into the system through spike 43. The fluid is first drawn into oxygenate or 147, which oxygenate the fluid and its red blood cells before it enters the circuit through first check valve 141. Once the fluid has entered the circuit, the circuit operates quite similarly to the circuit described above for FIG. 3.

FIG. 13 illustrates an embodiment of main body 183 of the apparatus of the invention. As described above, main body includes gas inlet 7, gas outlet 9, housing 11, pump motor 185, measuring system 33, and control system 35. Main body 183 housing 11 defines gas cavity 199 which forms a portion of environmental chamber 27 board chamber 13. Main body 183 housing 11 also defines modular transport system cavity 189, which is adapted and configured to receive a modular transport system such as cassette 155. In the embodiment shown, control system 35 includes display 193, keypad 195, printer 191, and data port 197. Main body 183 can also include any of a variety of controls, components, labels, indices, ports, and connectors commonly employed on clinical and laboratory apparatus.

Model Systems for Analyzing Oxygen Transport

The Three Compartment Model

Figure 14:
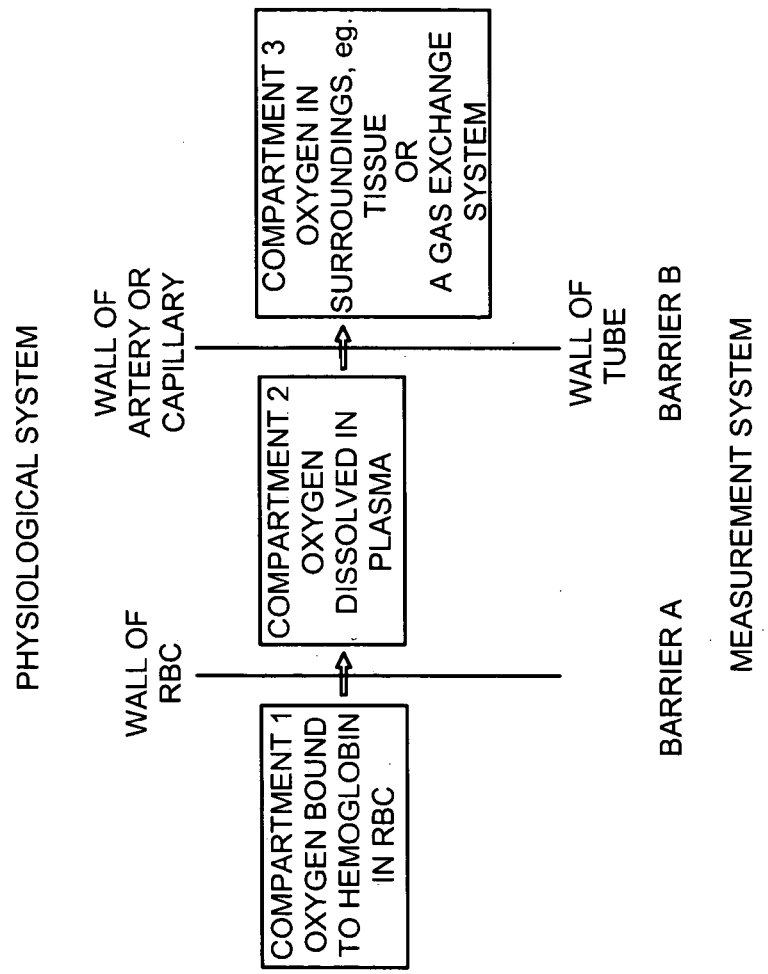
FIG. 14 illustrates three compartments associated with the circulation of blood, involved in oxygen transfer and utilization, and that can be modeled in an apparatus for measuring oxygen levels.

FIG. 14 shows three compartments and two barriers associated with circulation of blood, that are involved in oxygen transfer and utilization, and that can be modeled in an apparatus for measuring oxygen levels. Oxygen levels can be measured in any or all of these compartments.

Barrier A represents the aggregate of the exterior membranes of all the red blood cells in compartment one. Barrier B represents the diffusive system in which the plasma and the red blood cells are contained. This diffusive system can be, for example, a membrane or tube in an apparatus according to the invention or the walls of a blood vessel. When modeling a portion of the cardiac circulation, barrier B can represent a blood vessel wall in the myocardium.

Compartment one represents the interior of a red blood cell. A red blood cell lacks a nucleus, organelles, and any internal membranous structures. The cell membrane is the only membrane of a red blood cell; the red blood cell is basically a membranous sack containing hemoglobin. Oxygen in a red blood cell faces only two barriers to exiting the cell: dissociating from hemoglobin and diffusing across the red blood cell membrane. Dissociation from hemoglobin is fast compared to diffusion across the red blood cell membrane. Therefore, the rate at which oxygen leaves a red blood cell reflects the rate at which oxygen diffuses through or across the red blood cell membrane.

The level of oxygen in compartment one is the level of oxygenated hemoglobin in the red blood cell. Only negligible oxygen in a red blood cell is free of hemoglobin. In a red blood cell, total oxygen content can be measured by any of several known methods, for example, by the amount of hematocrit, or hemoglobin and the level of oxygen saturation ($S_{O2}$) of the hemoglobin. The level of oxygen saturation is defined by the concentration of oxygenated hemoglobin [HbO] divided by the concentration of total hemoglobin [Hb] times 100%; [HbO]/[Hb]×100%. This can be measured by a variety of methods and instruments known in the art.

Compartment two represents the blood outside of the red blood cell and can include other blood cells, proteins, plasma, serum components, laboratory additives (e.g. anticoagulants), and the like. Compartment two generally contains only a small amount of the total oxygen in blood. However, any oxygen entering or leaving the blood must cross through this compartment on its way to or from hemoglobin, the oxygen transport vehicle. Therefore, the level of oxygen in compartment two reflects the flux of oxygen from compartment one to compartment three, and also in the reverse direction. Oxygen levels in compartments one and three will affect the oxygen level in and the rate of change of oxygen level in compartment two.

The level of oxygen in compartment two can be represented by plasma oxygen levels. This can be measured as $P_{O2}$, the partial pressure of oxygen in plasma. This measurement can be conducted by a variety of methods and instruments known in the art. Since partial pressure measurements are affected only by gas molecules free in solution, oxygen that is bound to hemoglobin is not included in instantaneous $P_{O2}$ measurements. Over time, however, the hemoglobin does affect $P_{O2}$ values by acting as an oxygen sink, which removes excess oxygen from the plasma when levels are high and replaces plasma oxygen when levels are low.

Compartment three represents the surroundings of a vessel or tube carrying blood. In an animal, compartment three represents tissue that surrounds a blood vessel. Lung tissue supplies oxygen to the blood via diffusion of oxygen through the blood vessel wall and across the membrane of the red blood cell, leading to the formation of oxygenated hemoglobin. Other tissues are nourished by oxygen that dissociates from hemoglobin, crosses the red blood cell membrane, leaves the blood vessel, and enters the tissue. In an apparatus that measures oxygen levels in blood or blood components, compartment three typically represents the surroundings of a tube or membrane, such as a gas permeable silicon or silastic tube, containing blood. In such an apparatus, compartment three can be a gas or liquid (fluid) filled container from which oxygen can diffuse through the tube and into compartments two and one. In addition, in such an apparatus, oxygen can diffuse from compartments one and two into compartment three.

In the method and apparatus of the present invention, the oxygen concentration in compartment three can be controlled. This allows control of the direction and amount of flow of oxygen into and out of compartments one and two. In the method and apparatus of the invention, measuring the amount of oxygen in either or both of compartments one and two reveals the direction and rate of movement of oxygen. For example, depletion of oxygen in compartment three will deplete oxygen in the plasma, and oxygen will dissociate from oxygenated hemoglobin, diffuse through the membrane of the red blood cell and out of the cell. When the concentration of oxygen in compartment three is higher than the concentration in compartment two, the plasma will become oxygenated, and oxygen will diffuse through the membrane of the red blood cell and into the cell, and form oxygenated hemoglobin.

The diffusion and equilibria of oxygen in such a compartmentalized system can be modeled mathematically. Diffusion constants for each compartment are given in Table 1, which lists measured and calculated estimates constants affecting oxygen diffusion from the red blood cell. Additionally, the diffusion constant of molecular oxygen in water is approximately $2.0 \cdot 10^{-4}$ cm$^2$/sec at 310° K., about 10 times that of the red blood cell membrane.

TABLE 1

Table of values for red blood cell parameters from the literature

| RBC parameter | Symbol | Value | Unit | Source | Comment |
|---|---|---|---|---|---|
| Bunsen coefficient | $\alpha$ | $1.56 \cdot 10^{-9}$ | mole/cm$^3$/mm Hg | Popel Clark | Plasma O$_2$ |
| cell volume | V | $90 \cdot 10^{-12}$ | cm$^3$ | Kawai | |
| cell volume | V | $87 \cdot 10^{-12}$ | cm$^3$ | Huxley & Kutchai | |
| cell volume | V | $66 \cdot 10^{-12}$ | cm$^3$ | Groebe | |
| cell area | A | $0.7 \cdot 10^{-6}$ | cm$^2$ | Groebe | |
| cell area | A | $1.35–1.82 \cdot 10^{-6}$ | cm$^2$ | Huxley & Kutchai | |
| cell area | A | $1.60 \cdot 10^{-6}$ | cm$^2$ | Kawai | |
| cell area to volume | A/V | $6.96 \cdot 10^5$ | cm | Clark | |
| cell radius | r | $3.91 \cdot 10^{-4}$ | cm | Clark | |
| cell radius | r | $2.75 \cdot 10^{-4}$ | cm | Huxley & Kutchai | |
| cell radius | r | $2 \cdot 10^{-4}$ | cm | Groebe | |
| cell radius | r | $4 \cdot 10^{-4}$ | cm | Kawai | |
| Cell length | l | $2 \cdot 10^{-4}$ | cm | Clark | |
| Cell length | l | $5.2 \cdot 10^{-4}$ | cm | Groebe | |
| Diffusion coefficient | $D_0$ | $9.5 \cdot 10^{-6}$ | cm$^2$/sec | Groebe | Within RBC |
| Diffusion coefficient | $D_0$ | $16.0 \cdot 10^{-6}$ | cm$^2$/sec | Baxley & Hellums | Within RBC |
| Diffusion coefficient | $D_0$ | $18.0 \cdot 10^{-6}$ | cm$^2$/sec | Brower | Within RBC |
| Diffusion coefficient | $D_0$ | $9.5 \cdot 10^{-6}$ | cm$^2$/sec | Popel, Clark | averaged |
| Diffusion coefficient | $D_0$ | $20.0 \cdot 10^{-6}$ | cm$^2$/sec | Huxley & Kutchai | Within RBC |
| Diffusion coefficient | $D_0$ | $0.12 \cdot 10^{-6}$ | cm$^2$/sec | Popel | membrane DBL |
| Diffusion coefficient | $D_0$ | $7.0 \cdot 10^{-6}$ | cm$^2$/sec | Popel | membrane only |
| Diffusion coefficient | $D_{mus}$ | $10.0 \cdot 10^{-6}$ | cm$^2$/sec | Groebe | myocardium |
| Hb conc per RBC | $c_{RBC}$ | $29 \cdot 10^{-12}$ | g/cell | Huxley & Kutchai | |
| Hb conc in RBC | $c_{Hb}$ | $2.03 \cdot 10^{-5}$ or $1.2 \cdot 10^{-19}$ | mole/cm$^3$ or molecules/cm$^3$ | Clark | |
| membrane thickness | $\Delta x$ | $5.5 \cdot 10^{-4}$ | cm | Huxley & Kutchai | DBL |
| membrane thickness | $\Delta x$ | $1 \cdot 10^{-4}$ | cm | Huxley & Kutchai | membrane only |
| membrane thickness | $\Delta x$ | $2 \cdot 10^{-4}$ | cm | Huxley & Kutchai | DBL |
| membrane thickness | $\Delta x$ | $8 \cdot 10^{-7}$ | cm | Huxley & Kutchai | membrane only |
| membrane thickness | $\Delta x$ | $1.4–3.4 \cdot 10^{-4}$ | cm | Huxley & Kutchai | average |

Within the red blood cell, represented by compartment 1, the diffusion of $O_2$ is affected by hemoglobin and is approximately $7 \cdot 10^{-5}$ cm$^2$/sec. The diffusion constant through the red blood cell membrane (Barrier A) approximates $1.0 \cdot 10^{-5}$ cm$^2$ sec if the diffusion boundary layer is not included, and $1 \cdot 10^{-7}$ cm$^2$/sec if it is.

In the plasma, represented by compartment 2, the value is approximately $1 \cdot 10^{-5}$ cm$^2$/sec. The diffusion constant of the apparatus, barrier B, is significantly larger and depends on the $pO^2$ across the membrane but is in the area of $1 \cdot 10^{-3}$ cm$^2$/sec or more. Thus, the diffusion through the red blood cell membrane is the "slowest process". In addition, diffusion throughout the red blood cell can be assumed instantaneous because of the facilitation of diffusion by hemoglobin and the small radius of the red blood cell. However, diffusion through the plasma must be considered. Finally, the chemical dissociation of oxyhemoglobin into hemoglobin and oxygen has a dissociation constant of 44 sec$^{-1}$ or about 16 milliseconds, which will be seen to be at least 100 times shorter than the time constant for diffusion.

Compartment three can be made to mimic a physiological environment. Three factors are important in measuring the rate of oxygen gained or lost by the blood: the initial $O_2$ content, the final $O_2$ content, and the amount of time available to transfer the $O_2$ from blood to tissue, or tissues to blood. The partial pressure of oxygen ($pO_2$) of plasma and the oxygen saturation ($SO_2$) of the red blood cells are related by the oxygen dissociation curve and it is assumed that the tissue is in equilibrium with the plasma. The blood enters the tissue at a $pO^2$ of approximately 96 mm Hg or 97% $SO_2$. Under ordinary conditions, blood leaves at a $pO^2$ of approximately 40 mm Hg or 75% $SO_2$. Under conditions of maximum exertion, blood leaves at a $pO^2$ of approximately 15 mm Hg or 40% $SO_2$.

Under normal conditions, blood flow in the coronary artery system is 1.06 ml/sec or 63.6 ml/min., and transit time through the coronary system is 1–5 seconds (median time of 1.6 seconds). Under maximum exertion, blood flow in the coronary artery system is 2.53 ml/sec or 152 ml/min and transit time is less than that of normal exertion. The unloading time for a normal red blood cell is about 0.063 seconds under optimal conditions, i.e. if there is no "dead space" around the red blood cell and the $pO^2$ of the plasma is 0 mm Hg. If there is a dead space (compare the values of cell membrane thickness from Huxley and Kutchai in Table 1), the permeability decreases from 40 to 70 times, so the time for the red blood cell to unload a significant amount of $O_2$ is from 1 to 4 seconds, with time increasing as the $pO^2$ of the plasma becomes greater than 0 mm Hg. Thus, the transit time through the coronary artery system approaches the unloading time of the red blood cell. Since cholesterol has been shown to increase the membrane thickness and "stiffen" the red blood cell membrane, it could be expected to increase the "release time" for oxygen from red blood cells.

Mathematical Description of Oxygen Diffusion in Tissue and Apparatus

Blood to Tissue Oxygen Transport

Although not limiting to the present invention, transport of oxygen from red blood cells to surrounding tissue can be modeled as follows. Calculations are presented that show that the release time for $O_2$ from red blood cells is close to the residence time of the red blood cell in the coronary system. Sequential measurements of blood oxygen saturation ($SO_2$) are made when oxygenated blood is subjected to conditions similar to the myocardium. The natural logarithm of the relative value of the $SO_2$ at time t compared to the initial value of the $SO_2$ can be fitted to a straight line whose slope is proportional to the parameters of the red blood cell membrane, the sample size, the hematocrit and the diffusion parameters of the apparatus.

For practical calculations, the $O_2$ content of a single red blood cell is difficult to work with. A more suitable estimate of tissue bed $O_2$ availability can be derived by calculations based on a milliliter of whole blood. Under normal physiologic conditions, each gram of hemoglobin (Hb) can bind 1.34 of $O_2$, and each 100 ml of whole blood contains about 15 g of Hb, so that each 100 ml of whole blood can bind up to 20.1 ml of $O_2$ or 0.201 ml $O_2$/ml (20 volume %). Normal arterial blood at a $pO^2$ (partial pressure of $O_2$ dissolved in the blood plasma) of 95.7 mm Hg releases about 0.045 ml of $O_2$/ml blood as the $pO^2$ drops to that of mixed venous blood where the $pO^2$ is 40 mm Hg. This process of unloading takes the $O_2$ saturation of Hb from 97% to 75%. For any Hb value, the $O_2$ concentration of saturated whole blood is equal to 1.34·g Hb/ml. By determining the red blood cell $O_2$ saturation ($SO_2$) the $O_2$ concentration of unsaturated whole blood is equal to $SO_2 \cdot 1.34 \cdot Hb$/ml.

In addition to the $O_2$ contained in the red blood cells, the blood contains $O_2$ dissolved in the plasma, which obeys Henry's law, where $[O_2] = \alpha \cdot pO_2 \cdot (1-Hct)$ ($\alpha = 2.04 \cdot 10^{-5}$ ml $O_2$/mm Hg, Hct=hematocrit). At maximum plasma $pO_2$ of 149 mm Hg (1 atmosphere) and a Hct of 40%, about 0.002 ml of $O_2$ can be carried by 1 ml of plasma—about 1% of the carrying capacity of the red blood cell (2). The plasma $O_2$ content is, therefore, negligible. Rather, the primary influence of the plasma $O_2$ content on tissue oxygenation is in the plasma $pO^2$ regulation of $SO_2$, as depicted in the oxygen dissociation curve of hemoglobin.

As stated, the $SO_2$ of arterial blood delivered to the tissues under ordinary conditions is about 97%. From the $O_2$ dissociation curve of Hb, this $SO_2$ corresponds to a $pO^2$ of 95.7 mm Hg. Thus, $[O_2]_{red\ blood\ cell}$=0.195 ml $O_2$/ml blood, $[O_2]_{plasma}$=0.002 ml $O_2$/ml blood, and $[O_2]_{blood}$=0.197 ml $O_2$/ml blood. The $SO_2$ of mixed venous blood leaving the tissues under ordinary conditions is about 75%, corresponding to a $pO^2$ of about 40 mm Hg. Thus, $[O_2]_{red\ blood\ cell}$=0.151 ml $O_2$/ml blood, $[O_2]_{plasma}$=0.001 ml $O_2$/ml blood, and $[O_2]_{blood}$=0.152 ml $O_2$/ml blood.

Under conditions of maximum stress and increased tissue $O_2$ demand, the $SO_2$ of arterial blood does not change appreciably in normal healthy patients. However, the $SO_2$ of mixed venous blood, equal to that of the perfused tissues, does change to a remarkable degree. The $SO_2$ of mixed venous blood leaving the tissues under conditions of maximum stress can go as low as 20% (a $pO^2$ of about 15 mm Hg). Thus, under maximum stress conditions $[O_2]_{red\ blood\ cell}$=0.040 ml $O_2$/ml blood, $[O_2]_{plasma}$=0.000 ml $O_2$/ml blood, and $[O_2]_{blood}$=0.040 ml $O_2$/ml blood. It follows that the normal $O_2$ delivery of 0.045 ml $O_2$/ml blood rises under maximum stress to 0.157 ml/$O_2$/ml blood, a 3.5-fold increase in tissue $O_2$ availability.

During normal conditions, the average blood flow in the coronary arteries is 1.06 ml/sec or 63.6 ml/min. This flow rate results in an average volume of $O_2$ delivered of 1.06 ml blood/sec·0.045 ml $O_2$/ml blood=0.048 ml $O_2$/sec or 2.86 ml $O_2$/min. During conditions of maximum stress and increased cardiac output, the average blood flow per sec in the coronary arteries can increase 2.39-fold, so that the average blood flow is 2.39·1.06 ml/sec=2.53 ml/sec or 151.8 ml/min. This flow rate results in an average volume of $O_2$ delivered of 2.53 ml blood/sec·0.157 $O_2$/ml blood=0.379 ml $O_2$sec or 23.83 ml $O_2$/min. The maximum stress-induced 2.39-fold increase in coronary blood flow is designated the coronary flow reserve factor, which represents 152 ml blood/min in an unimpeded coronary arterial system.

During normal conditions, the area of the heart served by the coronary artery system (the ventricles) needs 1.3 ml $O_2$/min/100 g. During conditions of maximum stress, this value increases to 8.0 ml $O_2$/min/100 g. Reciprocal blood transit times through the heart have been calculated to be 0.2 $sec^{-1}$ to 1.0 $sec^{-1}$ (median, 0.6 $sec^{-1}$). These reciprocal blood transit times correspond to cardiac transit times of 1 to 5 sec (median, 1.6 sec). Under conditions of maximum stress, cardiac transit time decreases to less than 1 sec. The minimum $O_2$ unloading time of normal red blood cell with a membrane thickness of 1 µM has been given as 0.063 sec, with more likely times in vitro of 0.4 to 1.0 sec. These values are close to the average cardiac transit time, but still lower than cardiac transit time under maximum stress.

Oxygen Transport in a Gas Exchange Apparatus

Although not limiting to the present invention, transport of oxygen from a red blood cell to surroundings in a gas exchange apparatus can be modeled as follows.

A First Mathematical Model

The requirements described above for delivery of blood through the coronary arteries can be met by a coronary embodiment of the device of the invention fitting parameters described below. For example, a coronary embodiment typically will have a $SO_2$ into the apparatus of 97%, corresponding to a $pO^2$ of 95.7 mm Hg; an $SO_2$ out of the apparatus of 75%, corresponding to a $pO^2$ of 40 mm Hg (normal conditions); or an $SO_2$ out of the apparatus of 20%, corresponding to a $pO^2$ of 15 mm Hg (maximum stress conditions). These parameters describe a rate of $O_2$ delivery to the tissue of 2.86 ml $O_2$/min under normal conditions and a rate of $O_2$ delivery to the tissue of 23.83 ml $O_2$/min under conditions of maximum stress. This corresponds to a total $O_2$ delivery to the tissue of about 0.24 ml $O_2$/pass under normal conditions and a total $O_2$ delivery to the tissue of about 0.40 ml $O_2$/pass under conditions of maximum stress.

Although not limiting to the present invention, a coronary embodiment of the apparatus can be envisioned as having two compartments that are separated by a membrane or tubing barrier permeable to $O_2$ but not to a liquid such as blood plasma: In this embodiment: $V_1$=volume of the sample; $V_2$=volume of the "environment"; $C_1$=oxygen concentration in the sample; $C_2$=oxygen concentration in the "environment"; $\Delta C = C_1 - C_2$; A=membrane area; P=membrane permeability to $O_2$; $\Delta x$=membrane or tubing thickness; $(pO_2)_1$=partial pressure of $O_2$ in sample; $(pO_2)_2$=partial pressure of $O_2$ in environment; $\Delta pO_2 = (pO_2)_1 - (pO_2)_2$; $J_S$=current across membrane; $N_1$=amount of $O_2$ in sample compartment; $N_2$=amount of $O_2$ in environmental compartment; $N = N_1 + N_2$=total amount of $O_2$ in system=constant. Each of these variables can be present in a coronary embodiment including two compartments separated by a barrier permeable to oxygen.

The following equations can describe such a coronary embodiment. Equation 1:

$$J_S = P \cdot \Delta C = P \cdot \alpha \cdot \Delta pO_2$$

Equation 1 describes the relationship between current across membrane (J), $O_2$ pressure gradient ($\Delta pO_2$) and concentration gradient. $\Delta C\alpha$=relationship between $\Delta C$ and $\Delta pO_2 = 3 \cdot 10^{-5}$ ml $O_2$/(ml blood·mm Hg). P is a constant. Equation 2:

$$N_1(t) = C_1(t) \cdot V_1 :$$
$$N_2(t) = C_2(t) \cdot V_2 :$$
$$N = N_1 + N_2$$

Equation 2 describes the relationship between amount of $O_2$ and volumes and concentrations in each compartment. N(t)= number of $O_2$ molecules at time (t), C(t)=$O_2$ concentration at time (t) and V=volume of compartments 1 and 2. Equation 3:

$$dN_1(t)/dt = V_1 \cdot dC_1(t)/dt$$
$$dN_2(t)/dt = V_2 \cdot dC_2(t)/dt$$

Equation 3 describes the relationship between rate of change of amount of $O_2$ and volumes and concentrations in each compartment.

Combining these equations yields equation 4 (remembering that N is a constant):

$$d(\Delta C)/dt = -A \cdot P \cdot \left[\frac{1}{V_1} + \frac{1}{V_2}\right] \cdot (\Delta C)$$

Equation 4 is the differential equation derived by adding the equations for continuity and diffusion. Equation 4 has a solution of the form of equation 5:

$$\Delta C(t)/\Delta C(0) = e^{-A \cdot P \cdot [1/V_1 + 1/V_2] \cdot t} = e^{-\frac{t}{t_0}}$$

Equation 5 represents a solution of equation 4 for concentration as a function of time.

Equation 5 can be applied specifically to a coronary embodiment of the present apparatus as follows: In applying it to oxygen transfer through the oxygen porous tubing used in the embodiment from blood or plasma to the environment, the environment has a much larger volume than the tubing and the following approximations hold, $V_2 \gg V_1$ and thus $1/V_2 \sim 0$.

The permeability constant of typical gas permeable tubing is shown in equation 6:

$$\Phi = 7961 \cdot 10^{-10} \frac{cm^3 \cdot mm}{cm^2 \cdot sec \cdot cm\, Hg} :$$

Equation 6 describes the value of the permeability constant under physiological conditions for silicone gas permeable tubing material suitable for an apparatus of the invention. Therefore, the time constant is described by equation 7:

$$\frac{1}{t_0} = \frac{A \cdot \Phi}{\Delta x \cdot \alpha \cdot V_1 \cdot 10}$$

$\Delta C$ expressed as $\Delta pO_2$

Equation 7 describes the value a of research apparatus time constant expressed in terms of $pO_2$. One apparatus suitable for a coronary embodiment can have $\Delta x=0.2415$ mm., $A=92.55$ cm$^2$, $V_1=15$ ml. And $\alpha=3.0\,C10^{-5}$ ml $O_2$/ml blood/mm Hg. Therefore, for such an apparatus, equation 7 yields equation 8:

$$\frac{1}{t_0} = \frac{92.55 \cdot 7916 \cdot 10^{-10}}{0.2415 \cdot 3 \cdot 10^{-5} \cdot 15 \cdot 10}$$

$$\frac{1}{t_0} = 6.78 \cdot 10^{-2} \text{sec}^{-1}$$

Equation 8 shows the value of a time constant for one apparatus suitable for a coronary embodiment as determined by substitution of suitable values in equation 7. Under typical physiological conditions, equation 7 reduces to equation 9:

$$\frac{\ln\left[\frac{40}{95.7}\right]}{-6.78 \cdot 10^{-2}} = t = 13 \text{ sec}$$

Equation 9 illustrates the time of oxygen to leave one apparatus suitable for a coronary embodiment for normal conditions. Under conditions of maximum stress these same equations yield, for a final oxygen pressure of 20 mm Hg, $t=23.1$ sec.

Due to several approximations made in this derivation, and known variations in certain of the factors included in these equations, it is believed that the interface between plasma and the gas permeable surface of an apparatus of the invention can introduce a t of from 2 to 26 seconds under typical conditions.

The above equations can be readily visualized as applying to blood, that is red blood cells and plasma, in an apparatus of the invention by envisioning that equation 5 applies to the diffusion from the red blood cell, with compartment one referring to the red blood cell and 2 referring to the plasma. The volume of the plasma is assumed to be much greater than that of the red blood cell, thus $1/V_2 \approx 0$, as in the above derivation. Further, the $O_2$ content of the plasma can be assumed to be nearly 0, since $\alpha$ is so small. Since the method and apparatus of the invention can employ oxygen saturation, $SO_2$, for a measurement of C in a red blood cell, the method and apparatus can relate this to the concentration. Equation 9 leads to equation 10, which shows this relationship. Equation 10:

$$d(\Delta C)/dt = -A \cdot D_0 \cdot \left[\frac{1}{V_1}\right] \cdot (\Delta C)$$

Equation 10 is a preliminary step on the way to equation 12 showing the differential equation derived by adding the equations for continuity and diffusion for red blood cells. In equation 10, $D_o$ is the oxygen diffusion coefficient for the red blood cell. The concentration of oxygen relates to the $SO_2$ by equation 11:

$$[O_2] = SO_2 \cdot 1.34 \frac{ml\,O_2}{g\,Hb} \cdot \frac{g\,HB}{ml\,blood} \approx SO_2 \cdot 20.1 \frac{ml\,O_2}{ml\,blood}$$

Equation 11 describes the relationship between oxygen concentration and oxygen saturation in the red blood cell. This leads to a solution of equation 11 in terms of $SO_2$ shown in equation 12.

$$SO_2(t) = SO_2(0) \cdot e^{-\frac{t}{t_0}} : \frac{1}{t_0} = \frac{A \cdot D_0}{V_1 \cdot 20.1}$$

Equation 12 shows a solution of equation 8 in terms of oxygen saturation in a red blood cell. The value of $D_o$ as $9.5 \cdot 10^{-6}$ cm$^3$/sec is known to be and the value of $V_1/A$ is approximately $1 \cdot 10^{-4}$ cm. Thus, equation 13 is:

$$\frac{1}{t_0} = \frac{9.5 \cdot 10^{-6}}{1 \cdot 10^{-4} \cdot 20.1} = 4.73 \cdot 10^{-3} \text{sec}^{-1}$$

Equation 13 describes the value for the time constant of the diffusion of oxygen from the red blood cell using a large, it is believe the largest reasonable value of $D_o$. A smaller, but still reasonable, value of $D_o$ including the "dead space" around the red blood cell is 2.0 to $4.0 \cdot 10^{-7}$ cm$^3$/sec. This increases the time constant of the red blood cell as shown in equation 14.

$$\frac{1}{t_0} = \frac{4.0 \cdot 10^{-7}}{1 \cdot 10^{-4} \cdot 20.1} = 2 \cdot 10^{-4} \text{sec}^{-1}$$

Equation 14 describes the value for the time constant of the diffusion of oxygen from the red blood cell using a smaller, but still reasonable, value of $D_o$.

Applying these values for the red blood cell to a normal case ($SO_2(t)=75\%$) and a maximum stress case ($SO_2(t)=20\%$), both with initial values of 97%, the times for discharge are in equations 15 and 16 for the higher value of the diffusion constant and equations 17 and 18 for the lower value of the diffusion constant. Equation 15:

$$\ln\left[\frac{.75}{.97}\right] = -4.73 \cdot 10^{-3} \cdot t : t = 54.3 \text{ seconds}$$

Equation 15 describes the time for red blood cell oxygen diffusion under normal conditions with higher $D_o$. Equation 16:

$$\ln\left[\frac{.75}{.97}\right] = -2 \cdot 10^{-4} \cdot t : t = 1286 \text{ seconds}$$

Equation 16 describes the time for red blood cell oxygen diffusion under normal conditions with lower $D_o$. Equation 17:

$$\ln\left[\frac{.20}{.97}\right] = -4.73 \cdot 10^{-3} \cdot t : t = 333.8 \text{ seconds}$$

Equation 17 describes the time for red blood cell oxygen diffusion under maximum stress with higher $D_o$. Equation 18:

$$\ln\left[\frac{.20}{.97}\right] = -2 \cdot 10^{-4} \cdot t : t = 7895 \text{ seconds}$$

Equation 18 describes the time for red blood cell oxygen diffusion under maximum stress with lower $D_o$.

These equations illustrate that the time required for oxygen to diffuse from a red blood cell to the plasma are long compared with the times required for oxygen to diffuse through a tubing or membrane employed in the present invention. Therefore diffusion through such tubing or membrane is fast and does not hinder measurement of rates of diffusion of oxygen through the cholesterol containing membrane of the red blood cell.

A Second Mathematical Model

In another modeling embodiment, also not limiting to the present invention, transport of oxygen from a red blood cell to surroundings in a gas exchange apparatus can be modeled as follows.

Red blood cells have a concentration of $O_2$, $C_I$, equal to $N_I/V_I$, where $N_I$ is the total number of oxygen molecules in the sample (Equation 19) and $V_I$ is the total volume of the red blood cells in the sample (Equation 20). $N_I$ is given by four times $n_0$, the number of possible oxygen molecules in one red blood cell, times $n_I$, the number of red blood cells in the sample times $SO_2$, the % oxygen saturation of the sample. $V_I$ is equal to $n_I$ times $v_{RBC}$, the average volume of each red blood cell (Equation 20). $V_I$ is also equal to the hematocrit times the total volume of the sample, $V_s$.

$$N_I = 4 \cdot n_0 \cdot n_I \cdot SO_2 \qquad \text{Equation 19}$$

$$V_I = n_I \cdot v_{RBC} = Hct \cdot V_S \qquad \text{Equation 20}$$

Equation 21 shows the oxygen concentration of the red blood cells and the $O_2$ content $[O_2]$ of the red blood cells in a blood sample is shown in Equation 22.

$$C_I = N_I/V_I = 4 \cdot n_0 \cdot n_I \cdot SO_2/n_I \cdot v_{RBC} = \qquad \text{Equation 21}$$
$$4 \cdot n_0 \cdot SO_2/v_{RBC} = 4 \cdot n_0 \cdot n_I \cdot SO_2/(Hct \cdot V_S)$$

$$[O]_I = C_I \cdot V_I = 4 \cdot n_0 \cdot n_I \cdot SO_2 = 4 \cdot n_0 \cdot SO_2 \cdot Hct \cdot V_s/v_{RBC} \qquad \text{Equation 22:}$$

The plasma has a dissolved oxygen concentration $C_{II}$ given by Equation 23 where $\alpha$ is the Bunsen coefficient and $pO_2$ is the partial pressure of oxygen in the plasma, and an oxygen $[O]_{II}$ content given by Equation 24.

$$C_{II} = \alpha \cdot pO_2 = N_{II}/V_{II} \qquad \text{Equation 23}$$

$$[O]_{II} = \alpha \cdot pO_2 \cdot V_S \cdot (1 - Hct) \qquad \text{Equation 24}$$

The flux of particles across each barrier is defined by $J$ which equals $\Delta N/\Delta t$. In equilibrium, the flux across barrier A equals the flux across barrier B equals the total flux across both barriers (Equation 25). Thus:

$$J_A = J_B = J_T \text{ or } \Delta N_I/\Delta t = \qquad \text{Equation 25}$$
$$\Delta N_{II}/\Delta t = -\Delta N_{III}/\Delta t \text{ for a closed system}$$

But the flux $J$ is also defined by the Fick relationship (Equation 26).

$$J = A \cdot D \cdot \Delta C/\Delta x = A \cdot D \cdot \Delta N/(V \cdot \Delta x) \qquad \text{Equation 26}$$

where A is the area of the membrane, D is the diffusion constant of the material of the membrane, $\Delta x$ is the thickness of the membrane and $\Delta C$ is the difference in concentration across the membrane.

Again in equilibrium; the flux across each membrane, $J_A$ and $J_B$ and the total flux $J_T$ are equal. Thus: where the subscripts A, B, and T represent barriers A, B and the equivalent barrier of A and B together. $J_A$ and $J_B$ are set equal and $C_{II}$ is eliminated. Then, $J_A$ and $J_T$ are set equal and solved for $D_T$, a combined diffusion constant (Equation 27 to Equation 29).

$$D_T = (\Delta x_T \cdot A_A \cdot D_A \cdot A_B \cdot D_B)/[ \qquad \text{Equation 27}$$
$$A_T \cdot (A_A \cdot D_A \cdot \Delta x_B + A_B \cdot D_B \cdot \Delta x_A)]$$

$$J_T = A_T \cdot D_T \cdot \Delta C/\Delta x_T = \qquad \text{Equation 28}$$
$$(A_A \cdot D_A \cdot A_B \cdot D_B \cdot)/(A_A \cdot D_A \cdot \Delta x_B + A_B \cdot D_B \cdot \Delta x_A) \cdot$$
$$(C_{III} - C_I)$$

Substituting the values of $C_I$ and $C_{III}$ $$J_T = -(4 \cdot n_I \cdot n_0 \cdot SO_2/(v_{RBC} \cdot n_I) - N_{III}/V_{III}) \cdot \qquad \text{Equation 29}$$
$$(A_A \cdot D_A \cdot A_B \cdot D_B)/(A_A \cdot D_A \cdot \Delta x_B + A_B \cdot D_B \cdot \Delta x_A)$$

The volume of the environment, $V_{III}$, can be made very much larger than $V_I$ and the number of oxygen molecules in the environment $N_{III} \approx 0$. Thus, since $J_T = (N_{III} - N_I)/\Delta t$,:

$$(4 \cdot n_0 \cdot n_I \cdot d(SO_2))/dt = - \qquad \text{Equation 30}$$
$$(4 \cdot n_0 \cdot SO_2/v_{RBC}) \cdot (n_I \cdot a_{RBC} \cdot D_A \cdot A_B \cdot D_B)/$$
$$(n_I \cdot a_{RBC} \cdot D_A \cdot \Delta x_B + A_B \cdot D_B \cdot \Delta x_A)$$

This can be expressed as:

$$d(SO_2))/SO_2 = -(a_{RBC}/v_{RBC}) \cdot \qquad \text{Equation 31}$$
$$(D_A \cdot A_B \cdot D_B \cdot dt)/(n_I \cdot a_{RBC} \cdot D_A \cdot \Delta x_B + A_B \cdot D_B \cdot \Delta x_A).$$

Equation 31 can be integrated t between the limits of $t=0$ and $t=t$, to give Equation 32.

$$\text{Ln}(SO_2)]_0^t = -(a_{RBC}/v_{RBC}) \cdot \qquad \text{Equation 32}$$
$$(D_A \cdot A_B \cdot D_B \cdot t)/(n_I \cdot a_{RBC} \cdot D_A \cdot \Delta x_B + A_B \cdot D_B \cdot \Delta x_A)$$

Since $V_I$ is the total volume of all the red blood cells: and $A_A$ is the total surface area of all the red blood cells $$V_I = n_I \cdot v_{RBC} = Hct \cdot V_s; v_{RBC} = \frac{Hct \cdot V_s}{n_I} \qquad \text{Equation 33}$$

$$A_A = n_I \cdot a_{RBC} \qquad \text{Equation 34}$$

Then can be expressed in terms of the oxygen saturation between time=0, the start of the experiment and any subsequent time t to obtain Equation 35

$$\frac{(SO_2)_t}{(SO_2)_0} = e^{-[(\cdot a_{RBC} \cdot D_A \cdot A_B \cdot D_B \cdot t)/[\cdot v_{RBC} \cdot (n_I \cdot a_{RBC} \cdot D_A \Delta x_B + A_B \cdot D_B \cdot \Delta x_A)]]} \quad \text{Equation 35}$$

If sequential relative SO$_2$ values are plotted against time the negative slope of the exponential curve is a straight line (Equation 36).

$$\text{slope} = -[(\cdot a_{RBC} \cdot D_A \cdot A_B \cdot D_B)/[\cdot v_{RBC} \cdot (n_I \cdot a_{RBC} \cdot D_A \cdot \Delta x_B + A_B \cdot D_B \cdot \Delta x_A)]] \quad \text{Equation 36}$$

Equation 35 can be expressed as:

$$\frac{(SO_2)_t}{(SO_2)_0} = e^{-\left[\frac{t}{t_0}\right]} \quad \text{Equation 37}$$

The term in the denominator of Equation 36 dictates the extremes of the slope.

If the condition shown in Equation 38 is true, then oxygen diffusion is governed by the red blood cell and is approximated by Equation 39, all variables mentioned in the literature as being affected by cholesterol.

$$[n_I \cdot a_{RBC} \cdot D_A / \Delta x_A << A_B \cdot D_B / \Delta x_B]] \quad \text{Equation 38}$$

$$\text{slope} = -[a_{RBC} \cdot D_{RBC} / \Delta x_{RBC}) / [v_{RBC}]] \quad \text{Equation 39}$$

Conversely, if the slope is governed by the apparatus as in Equation 40, and the slope is shown in Equation 41, then the measured value is governed by the apparatus.

$$[n_I \cdot a_{RBC} \cdot D_A / \Delta x_A >> A_B \cdot D_B / \Delta x_B]] \quad \text{Equation 40}$$

$$\text{slope} = -[(A_B \cdot D_B) / [(V_S \cdot Hct \cdot \Delta x_B]]. \quad \text{Equation 41}$$

Equation 41 shows a way to compare two apparati. Examples of calculations employing these equations are illustrated herein below.

From the equations above, it is known that $(SO_2)_t$, the red blood cell oxygen saturation at time t, shows an exponential decrease in an environment of 0% oxygen from the initial value $(SO_2)_0$ (Equation 1) with a time constant $t_0$.

$$\frac{(SO_2)_t}{(SO_2)_0} = e^{-\left[\frac{t}{t_0}\right]} \quad \text{Equation 42}$$

Table 2 shows measured and calculated values of the time constant $t_0$. S denotes the proportion of the sample in contact with the diffusion membrane (barrier B) at any time.

TABLE 2

Time constant (t$_0$) for oxygen release from a red blood cell and from blood samples

| t$_0$ in seconds | Method | Comment |
| --- | --- | --- |
| 1.5 sec | Microvessel; S ≈ 1 | Comparing artificial and human blood |
| 0.06 sec | Theoretical | red blood cells |
| 0.15–0.5 sec | Theoretical | Shape dependent |
| 2.5 sec | Microvessel; S ≈ 1 | Comparing artificial and human blood |

The sample time constant (t$_0$) is proportional to the total volume of red blood cells in the sample, which can be approximated by the hematocrit multiplied by the sample volume, and the combined permeability of the red blood cell and the apparatus. Values of the time constant for deoxygenation of one ml of red blood cells have been estimated at 0.01 to 0.03 sec for each mm Hg of the environment, thus making the time for a ml of red blood cells to go from 96 to 15 mm Hg approximately 0.8 to 2.4 sec.

$$P_d = \frac{D_d \cdot A_d}{\Delta x_d} \quad \text{Equation 43}$$

Permeability (P) is defined in equation 43, where D is the diffusion constant, A is the area of the membrane and $\Delta x$ is the membrane thickness. Since the barriers A and B in FIG. 14 are in series, that is; the oxygen molecules must pass through both barrier A and barrier B to reach the environment, the permeabilities of the red blood cell membranes (P$_{RBC}$) and the vessel wall or apparatus membrane (P$_{wall}$) are combined for a total permeability (P$_{Total}$) in Equation 44.

$$\frac{1}{P_{Total}} = \frac{1}{P_{RBC}} + \frac{1}{P_{Wall}} \quad \text{Equation 44}$$

Thus, if P$_{Wall}$ can be made large compared to P$_{RBC}$, P$_{Total}$, the measured permeability, approximates P$_{RBC}$, the permeability of the assemblage of red blood cells in Compartment A. as shown in Equation 45. Recalling that the SO$_2$ is a concentration, Equation 46 gives the value of the constant 1/t$_0$ in Equation 42, assuming the entire sample is in contact with (Barrier B).

$$P_{RBC} = [n_I \cdot a_{RBC} \cdot D_{RBC}] / \Delta x_{RBC} \quad \text{Equation 45}$$

The time constant is a function of the averaged properties of the red blood cell. The value of $n_I \cdot v_{RBC}$ can be approximated by the V$_S$·Hct, where V$_S$ is the sample volume and Hct is the hematocrit.

$$\frac{1}{t_0} = \frac{P_{RBC}}{V_{RBC}} = \frac{n_I \cdot a_{RBC} \cdot D_{RBC}}{\Delta x_{RBC} \cdot n_I \cdot v_{RBC}} = \frac{a_{RBC} \cdot D_{RBC}}{\Delta x_{RBC} \cdot v_{RBC}} \quad \text{Equation 46}$$

However, the entire sample is not in proximity to Barrier B. The plasma (compartment two) contains less than 2% of the oxygen in the blood but does pose a barrier to the oxygen from the red blood cells due to the time ($t_p$) required for diffusion through the liquid. This time is inversely proportional to sample flow rate (F) through the apparatus and the volume of the sample ($V_d$) in the diffusive section of the apparatus (Equation 47)

$$t_p = \frac{V_d}{F} \qquad \text{Equation 47}$$

The thickness of the diffusive layer is defined by the distance from the apparatus membrane at which the plasma $pO_2$ has fallen by 1/e from its mean value ($\Delta x_p$.) Equation 48 relates ($\Delta x_p$.) and ($t_p$) with $D_O$, equal the diffusion constant of oxygen in water ($2.0 \cdot 10^{-4}$ cm$^2$/sec). If $\Delta x_p$ is greater than the actual thickness of the sample chamber, then the value used in Equation 49 is the actual sample chamber thickness.

$$\Delta x_p \approx 2 \cdot \sqrt{D_0 \cdot t_p} \approx 2.8 \cdot 10^{-2} \cdot \sqrt{t_p} \qquad \text{Equation 48}$$

Equation 49 shows the approximate volume of the sample near the apparatus membrane.

$$V_D \approx \Delta x_p \cdot A_D \qquad \text{Equation 49}$$

Equation 50 defines the variable S, a scaling factor which accounts for the approximate proportion of red blood cells undergoing oxygen diffusion at any one time.

$$S = \frac{V_d}{V_s} \qquad \text{Equation 50}$$

Thus the time constant for release of oxygen from the red blood cells, which is of the order of 1 to 3 seconds, is "scaled" in the apparatus by a factor (S) as shown in Equation 50. For example, if $V_S$ is 5 ml, $A_D$=4 cm$^2$, $V_D$=1 cm$^3$. and the flow rate is 3 cm$^3$/min or 0.05 cm$^3$/sec, $t_p$=20 seconds from Equation 6, $\Delta x_p$.=0.13 cm. from Equation 48 and S≈0.10 from Equation 50. S is minimized by using a thin sample cassette (d is small), a fast pumping rate (F is large) and adjusting the deoxygenation membrane so that the change in oxygenation for each pass of an red blood cell is small. However, the time for a particular red blood cell to traverse the area of the cassette containing the diffusion barrier should be at least three times the time constant of the red blood cell oxygen release so that the apparatus value of S is not affected by the red blood cell values. From Table 2, this would indicate a time to traverse the region of deoxygenation of approximately 20 seconds. So the shape of the deoxygenating membrane and the flow rate should preferably be such to allow a time of at least 20 seconds residence time.

The combined value for the constant $1/t_0$ is given by Equation 10.

$$\frac{1}{t_0} = \frac{S \cdot a_{RBC} \cdot D_{RBC}}{\Delta x_{RBC} \cdot v_{RBC}} = \frac{S \cdot n_l \cdot a_{RBC} D_{RBC}}{\Delta x_{RBC} \cdot V_s \cdot Hct} \qquad \text{Equation 51}$$

A Third Mathematical Model

In yet another modeling embodiment, also not limiting to the present invention, transport of oxygen from a red blood cell to surroundings in a gas exchange apparatus can be modeled as follows.

Analysis of the effect of the time constant for oxygen release by a red blood cell on the rate of oxygen delivery to the myocardium or to the surroundings of an apparatus. This model employs diffusion only. The equation below illustrates the reaction that must appear before diffusion of the oxygen from the red blood cell.

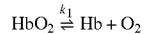

$k_1 = 44$ sec$^{-1}$ or $t = 16 \times 10^{-3}$ sec

Next, this model assumes that oxygen diffuses from the center of a red blood cell with a rate of diffusion described as $D_0$=7.0×10$^{-5}$ cm$^2$/sec. This diffusion is "facilitated" by hemoglobin. The red blood cell has a maximum radius, for these purposes, of 2.0×10$^{-4}$ cm. This yields:

$\Delta x = 2\sqrt{D_0 t}$ or $$\frac{\Delta x^2}{4D_0} = t$$

Plugging in the values above yields:

$$\frac{(2x10^{-4})^2}{4(7.0x10^{-5})} = t$$

or $t$=1.5×10$^{-4}$ sec

This calculated value is consistent with values for diffusion of oxygen through a red blood cell, including its wall, of 3×10$^{-1}$ sec and 2×10$^{-1}$ sec. The rate of diffusion in the red blood cell is faster than these measured rates, as required.

This model can also calculate a maximum diffusion time through plasma from capillary center. Assuming $\pi$=1×10$^{-4}$ cm & $D_o$=10$^{-5}$ cm$^2$/sec, then:

$\Delta x = 2\sqrt{D_o t}$ or $$\frac{\Delta x^2}{4D_0} = t$$

These equations yield:

$$\frac{(1x10^{-4})^2}{4 \cdot 10^{-5}} = 2.5x10^{-4} \text{sec}$$

This equation shows that diffusion outside the red blood cell is also much faster than diffusion through the red blood cell membrane.

Thus, the rate at which oxygen diffuses from the center of a red blood cell to the edge of a capillary or other tube or chamber containing the red blood cell is determined by the rate of diffusion through the red blood cell membrane.

Now, similar calculations can yield the time required to move through an apparatus. First, assume a maximum distance from the red blood cell to the diffusion membrane of $1 \times 10^{-1}$ cm (1 mm). This yields a time of:

$$t = \frac{\Delta x^2}{4D_o} = \frac{10^{-2}}{4 \times 10^{-5}} = 250 \sec$$

Similar calculations can model release of oxygen in the myocardium, for example, the effect of $t_o$ on oxygen release in myocardium. These calculations include two components. First, how much $D_2$/time is released by an red blood cell during passage through myocardium. Second how many red blood cell pass through the myocardium/time. For these calculations let Q=initial value of $O_2$ in one red blood cell; A=x sectional area; l=length; $t_N$=normal time for one red blood cell to pass through myocardium; $t_s$=time to pass through myocardium during time of stress; $t_N > t_s$; and $T_o$=time constant for release of $O_2$ from red blood cells. Then for each red blood cell, initial oxygen constant=Q; and:

final oxygen content=$Q(e^{-t/t_o})$, oxygen delivered=$Q(1-e^{-t/t_o})$ normally $Q(1-e^{t_N/t_o})$, stress $Q(1-e^{t_s/t_o})$ Calculating the number of red blood cells delivered to myocardium N:

N $\alpha$ A 1/t, Normally $$N \alpha \frac{A_N l_N}{t_N}$$

Stress $$N \alpha \frac{A_s l_s}{t_s}$$

and assume $A_N = A_S$, $1_N = 1_s$

Then the total oxygen delivered can be represented as:

Total $[O_2]$ delivered $\alpha \cdot N \cdot Q(1-e^{-t/t_o})$

Normally $[O_2]_N$ delivered $$\alpha \frac{Al}{t_N}(1 - e^{-t_N/t_o})$$

Stress $[O_2]_s$ delivered $$\alpha \frac{Al}{t_s}(1 - e^{-t_s/t_o})$$

Ratio of $[O_2]$ delivered $$\left(\frac{[O_2]_s}{[O_2]_{ND}}\right) = \frac{t_N}{t_s} \frac{(1-e^{-t_s/t_o})}{1-e^{-t_N/t_o}}$$

But the myocardium has requirements for $[O_2]$ independent of what the red blood cells can deliver $$\left(\frac{[O_2]_s}{[O_2]_N}\right)_R$$

& doesn't depend on $t_o$. If $$\left(\frac{[O_2]_s}{[O_2]_N}\right)_R > \left(\frac{[O_2]_s}{[O_2]_N}\right)_D$$

symptoms result. If $t_o$ were very short $$\left(\frac{[O_2]_s}{[O_2]_N}\right) \approx \frac{t_N}{t_s}$$

and the $O_2$ delivery ratio would follow the flow rate proportionally.

If $t_o$ is significant compared to $t_N$ and especially $t_s$ then the $O_2$ delivery ratio would be less than expected from the flow rates alone. Assuming $t_s=1$ sec and $t_N=5$ sec, then the variation of the delivery ratio with $t_o$ is shown by the following. If $t_o$ is 300 msec as defined above as "normal" then the $O_2$ delivery ratio is 4.82 and is controlled by flow rate. If $t_o$ however increases to 1 second, the $O_2$ delivery ratio decreases to 3.18. If $t_o$ increases to 2 seconds the $O_2$ delivery ratio decreases to 2.00. In these circumstances, the subject's required $O_2$ delivery ratio remains the same; that is, it is independent of $t_o$.

Thus if $t_o$ increases so as to make $$\left(\frac{[O_2]_s}{[O_2]_N}\right)_R > \left(\frac{[O_2]_s}{[O_2]_N}\right)_D$$

then symptoms could occur on exertion. Conversely, if $t_o$ decreases so as to make $$\left(\frac{[O_2]_s}{[O_2]_N}\right)_R < \left(\frac{[O_2]_s}{[O_2]_N}\right)_D$$

due to cholesterol lowering therapy, then symptoms could decrease.

It is believed that the half life of red blood cells in the body is far less than the time needed to "open up" (remove plaque from) arterioles. Thus, lowering cholesterol could lead to cessation of symptoms on exertion by decreasing $t_o$ far more rapidly than by increasing flow without increasing:

$$\left[\frac{[O_2]_s}{[A-7]}\right]_R$$

by increasing A.

A Fourth Mathematical Model

Although not limiting to the present invention, a fourth mathematical model can be employed to compare different apparatus constructed to different specifications. For example, two apparati may be compared as shown in Equation 52.

$$\frac{D_d \cdot A_d \cdot t_d}{\Delta x_d \cdot V_d} = \frac{D_c \cdot A_c \cdot t_c}{\Delta x_c \cdot V_c} \text{ or } \frac{t_d}{t_c} = \frac{D_d \cdot A_d \cdot \Delta x_c \cdot V_c}{D_c \cdot A_c \cdot \Delta x_d \cdot V_d} \qquad \text{Equation 52}$$

Table 3 provides further illustration of this comparison. The effect of S, as defined above, is not included.

TABLE 3

Comparison of Apparati

| $D_0$ | Volume | Area | Length | Comment |
|---|---|---|---|---|
| tubing = tissue | Assumed t/r² = constant; cm tissue; | r = 1 · 10⁻⁴ r = 1.1 · 10⁻¹ cm tubing | | seconds in tubing = 10 seconds in capillary |
| tubing = tissue | r = 12.5 · 10⁻⁴ cm. l = 3 · 10⁻¹ cm | Δr = 62.5 · 10⁻⁴ cm; | | Measures SO₂ every 0.5 mm. at rates of 5–50 ml/hr. |

When are two apparati equivalent? They will be equivalent when the same $d[O_2]/dt$ per ml is achieved; i.e. when the same volume of $O_2$ is extracted from the blood sample per ml. If the values of $d[O_2]/dt$ are not equal, the slopes of the graph of ln $[SO_2]_t/[SO_2]_0$ vs t may be scaled proportionally to $d[O_2]/dt$.

Oxygen content of the blood: For normal blood, each 100 ml (deciliter) contains an average of 15 g. of hemoglobin (Hb). Each gram of Hb binds 1.34 ml of $O_2$ under normal physiological conditions. Thus each deciliter of blood can bind up to 20.1 ml of $O_2$ or 0.201 ml $O_2$ per ml blood. (20 volume %). For any Hb, $[O_2]$=1.34·g. Hb/ml of blood.=0.201 ml $O_2$/ml blood. For unsaturated blood, $[O_2]$=SO₂C1.34·g. $O_2$/g Hb·g Hb/ml of blood≈SO₂ C0.201 ml $O_2$/ml blood.

In addition to the oxygen contained in the red blood cells, the plasma obeys Henry's law, $[O_2]$=α·p $O_2$, ·(1-Hct) where α equals 2–3×10⁻⁵ ml $O_2$ per mm Hg, Hct is the hematocrit (% of blood that is red blood cells) and $pO^2$ is the partial pressure of $O_2$ dissolved in plasma in mm Hg. At maximum plasma $pO^2$ of 149 mm Hg and a Hct of 40%, this is about 0.002 ml $O_2$ per ml plasma, about 1% of that in the red blood cell. Thus, the total $[O_2]$ of blood at 100% saturation is 0.203 ml $O_2$/ml blood at full saturation and 0.203 ml $O_2$/ml blood·SO₂ at any saturation. Thus, fully oxygenated blood has an oxygen content, $[O_2]$, of approximately 0.203 ml $O_2 \cdot V_{SAMPLE}$.

Although not limiting to the present invention, the mass transfer of oxygen, $Q=K \cdot A \cdot \Delta p$ where: Q=volume rate of oxygen passing through membrane to plasma in ml/sec, K=membrane permeability to oxygen. A typical value is $2 \cdot 10^{-4}$ cm³/(sec·cm²·cm Hg). Note that K includes the thickness of the membrane. Δp is the oxygen $pO^2$ between the apparatus and the environment. The partial pressure of oxygen, $pO_2$, follows the oxygen dissociation curve of blood and is thus almost constant until the oxygen saturation is less than 50%. Thus a constant value for Δp can be used in the range of $SO_2$ from 0%–100%. Similarly, the red blood cells contain at least 97% of the oxygen, so the oxygen sample volume can be approximated by Hct·$V_S$. Thus, the time for an apparatus to go from full saturation $(SO_2)_0$ to a given desaturated state $(SO_2)_t$ equals the change in oxygen content divided by the rate of mass transfer:

$$\frac{d[O_2]}{V_s \cdot Hct \cdot dt} \approx \frac{0.203 \cdot \{(SO_2)_0 - (SO_2)_t\}}{K \cdot A \cdot \Delta p} \qquad \text{Equation 53}$$

The present invention may be better understood with reference to the following examples. These examples are intended to be representative of specific embodiments of the invention, and are not intended as limiting the scope of the invention.

EXAMPLES

Example 1

Correlation of Cholesterol Levels With Red Blood Cell Oxygen Diffusion in an Animal Model This study determined a correlation between the level of a blood lipid, cholesterol, and the rate at which oxygen diffused out of red blood cells.

Materials and Methods

Ten New Zealand White Rabbits were divided into an experimental group and a control group. The six experimental rabbits were fed for eight weeks a diet of standard laboratory rabbit chow supplemented with 0.25% cholesterol. The four control rabbits received, for the same period, the same diet lacking the added cholesterol. After eight weeks on this diet, blood samples were collected from each rabbit by standard methods using sodium heparin as an anticoagulant. The plasma and red blood cell cholesterol levels were determined in an aliquot of each blood sample by the Allain's assay and Abell's methods, each of which is a standard method.

Figure 15:
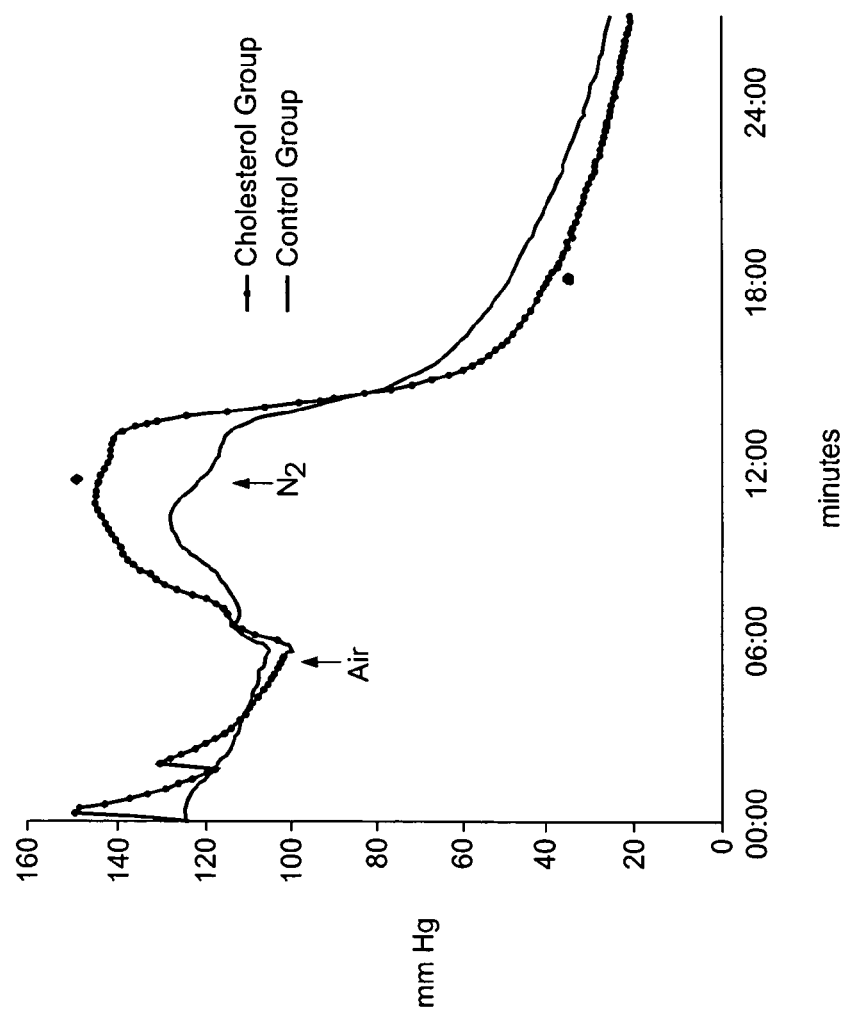
FIG. 15 illustrates the plasma oxygen levels for cholesterol-fed and control animals as determined by an embodiment of the method of the invention.

Another aliquot of each blood sample was circulated through a closed circuit diffusion chamber in gas permeable tubing and exposed to atmospheric pressures of oxygen (160 mm Hg) and carbon dioxide (4 mm Hg) for 6 minutes (time 6–12 minutes in FIG. 15). This was considered full saturation of the blood with oxygen. Each blood sample was then subjected to desaturation by circulating the blood sample through the closed circuit diffusion chamber and exposing the sample to nitrogen gas for 15 minutes (time 12–27 minutes in FIG. 15). During exposure to oxygen and during exposure to nitrogen, each sample was subjected to continuous blood gas monitoring for pH, $P_{CO2}$, and $P_{O2}$.

Results

The results of this study are shown in Table 4 and FIG. 15. Table 4 illustrates that the experimental, cholesterol-fed animals had higher levels of cholesterol both in their plasma and in their red blood cell membranes than the control animals.

This higher level of cholesterol in plasma and in red blood cell membranes correlated with slower diffusion of oxygen through the red blood cell membrane (FIG. 15). FIG. 15 shows that the cholesterol-fed animals achieved higher levels of plasma oxygen during the saturation phase due to slower uptake by the red blood cells. When the cells were exposed to the nitrogen atmosphere, oxygen was exchanged out of the cholesterol-fed rabbit plasma more quickly than the control rabbit plasma. This indicates that red blood cell oxygen diffused more slowly into the plasma from the red blood cells from the cholesterol-fed rabbits than in the control blood.

TABLE 4

Cholesterol levels in rabbit plasma and red blood cell membranes in control and experimental groups after eight weeks of feeding.

| | Cholesterol (mg/dl) | | | |
|---|---|---|---|---|
| | Plasma | | Red Blood Cell Membrane | |
| Group | Mean | SEM | Mean | SEM |
| Control | 60 ± 1.2 | | 22 ± 1.7 | |
| Cholesterol | 928 ± 31* | | 121 ± 3* | |

*$p < 0.05$ vs. Control Group

Conclusion

Oxygen diffused more slowly across the red blood cell membranes of animals with the higher level of cholesterol in plasma or in red blood cell membrane. This indicates that the rate of diffusion of oxygen across a red blood cell membrane correlates with increased levels of the blood lipid cholesterol in an animal model commonly used in this field for study of blood lipids.

Example 2

Correlation of Cholesterol Levels With Red Blood Cell Oxygen Diffusion in Humans Study 1

This study determined a correlation between the level of a blood lipid, cholesterol, and the amount of oxygen that diffused into human red blood cells in 15 minutes.

Materials and Methods

Blood samples were collected by standard methods from four informed human volunteers with varying cholesterol levels. Cholesterol levels were determined in one aliquot of each blood sample by Abell's assay, a standard method. Another four aliquots from each blood sample were subjected to blood gas analysis as follows: Each aliquot was subjected to desaturation as described in Example 1 and the amount of oxygen bound to hemoglobin (Hb) was determined. Then, the aliquot was circulated through a diffusion chamber and exposed to capillary gas pressures, 23 mm Hg of $O_2$ and 46 mm Hg $CO_2$. After 15 minutes of circulation, the amount of oxygen bound to hemoglobin (Hb) was determined again.

Results

The results of this study are presented in Table 5. The results presented in Table 5 show that the amount of oxygen that crossed the red blood cell membrane decreased as the cholesterol level increased.

TABLE 5

Correlation with cholesterol levels of amounts of oxygen bound to hemoglobin in human red blood cells before and after exposure to oxygen.

| | | $O_2$ Content (ml/gm of Hb) | | | | | |
|---|---|---|---|---|---|---|---|
| | P Chol | Pre-Diffusion | | Post-Diffusion | | % | p |
| Sample | (mg/dl) | Mean | SEM | Mean | SEM | Change | Value |
| A | 87 | 13.3 ± 0.391 | | 20.5 ± 0.478 | | 35% | 0.037 |
| B | 157 | 14.8 ± 0.091 | | 19.5 ± 0.270 | | 24% | 0.041 |
| C | 241 | 15.8 ± 0.013 | | 20.2 ± 0.551 | | 22% | 0.020 |
| D | 400 | 16.3 ± 0.079 | | 17.5 ± 0.196 | | 7% | 0.014 |

Conclusion

Oxygen diffused more quickly across the red blood cell membranes of humans with the lower level of cholesterol. This indicates that the rate of diffusion of oxygen across a red blood cell membrane correlates inversely with increasing levels of the blood lipid cholesterol in humans.

Study 2

This study determined that plasma cholesterol levels and red blood cell membrane cholesterol levels in humans inversely correlate with the rate of oxygen diffusion from the human subject's red blood cells.

Materials and Methods

In this second study, venous blood was collected from 22 volunteers, standardized to a hematocrit level of the blood of 40%, and circulated in a closed-loop $O_2$ diffusion chamber to full saturation and subjected it to desaturation, while continuously measuring the $O_2$ saturation.

Figure 16A:
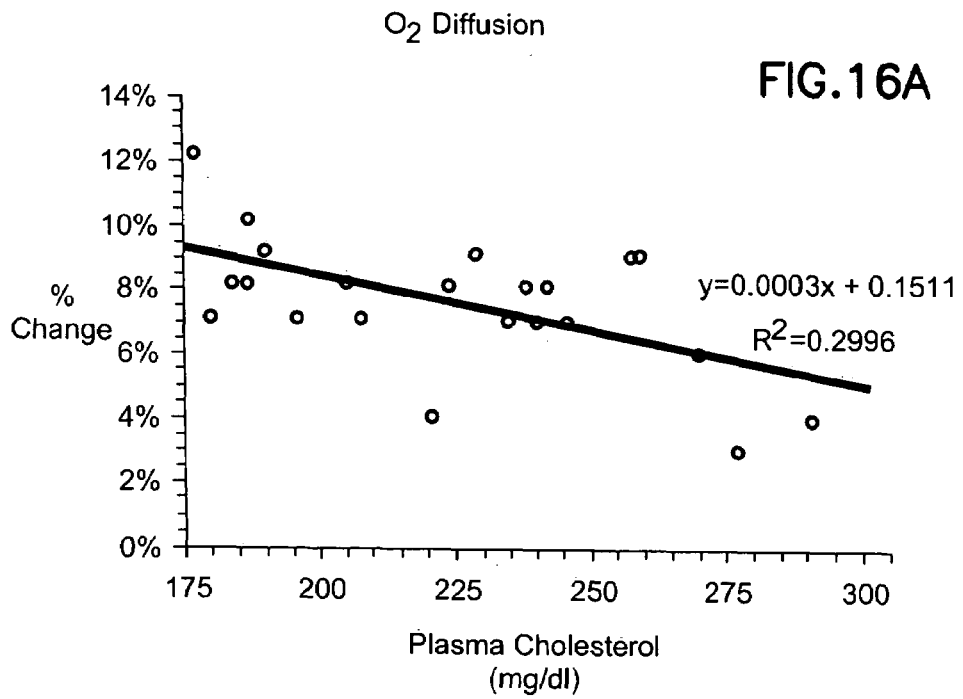
FIGS. 16A and 16B illustrate correlations of plasma cholesterol (A) and red blood cell membrane cholesterol (B) levels with percent changes per unit time in $O_2$ saturation.
Figure 16B:
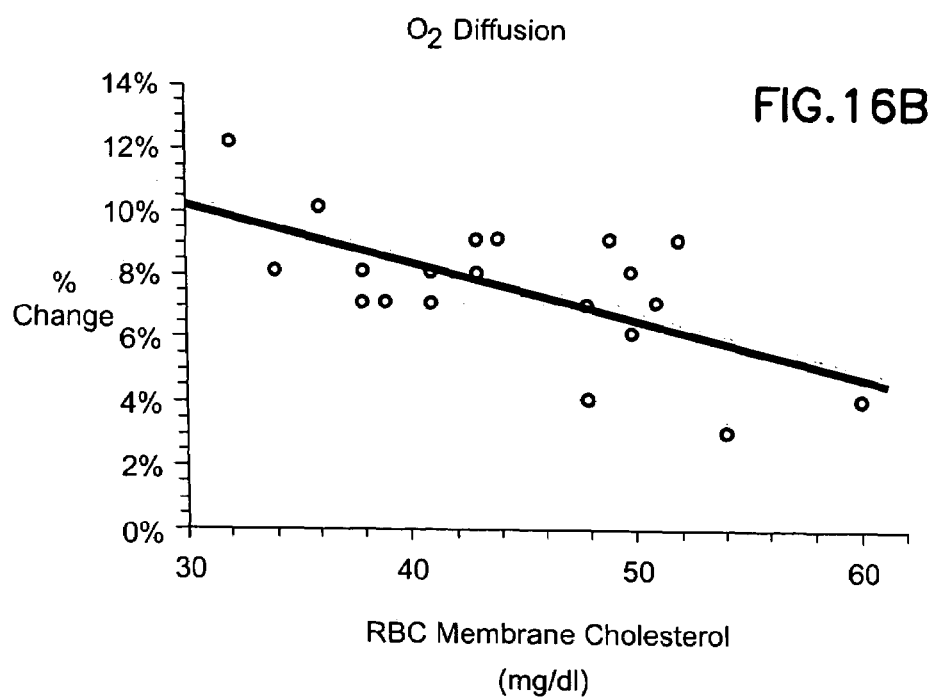

Results $O_2$ diffusion from inside to outside the red blood cell was represented by the percent change of $O_2$ saturation in a controlled time interval. The plasma cholesterol and red blood cell membrane cholesterol levels were inversely correlated with the percent changes in $O_2$ saturation: $R^2=0.2996$ and $R^2=0.3870$, respectively (FIG. 16).

Conclusions

Again, plasma cholesterol and red blood cell membrane cholesterol levels inversely correlated with the trans-red blood cell membrane $O_2$ diffusion rate, and high blood cholesterol restricted $O_2$ transport.

Study 3

This study determined that groups of patients with ranges of cholesterol levels can also be grouped by the rate at which oxygen diffuses from their red blood cells.

Materials and Methods

In this third study, red blood cell $O_2$ diffusion was studied as described above in blood from 54 volunteers, whose blood hematocrit was again standardized to 40%. Patients were grouped by plasma cholesterol (mg/dl) of <199 (n=11, 200 to 224 (n=15), 225 to 249 (n=23), and 275 to 299 (n=5).

Results

Figure 17:
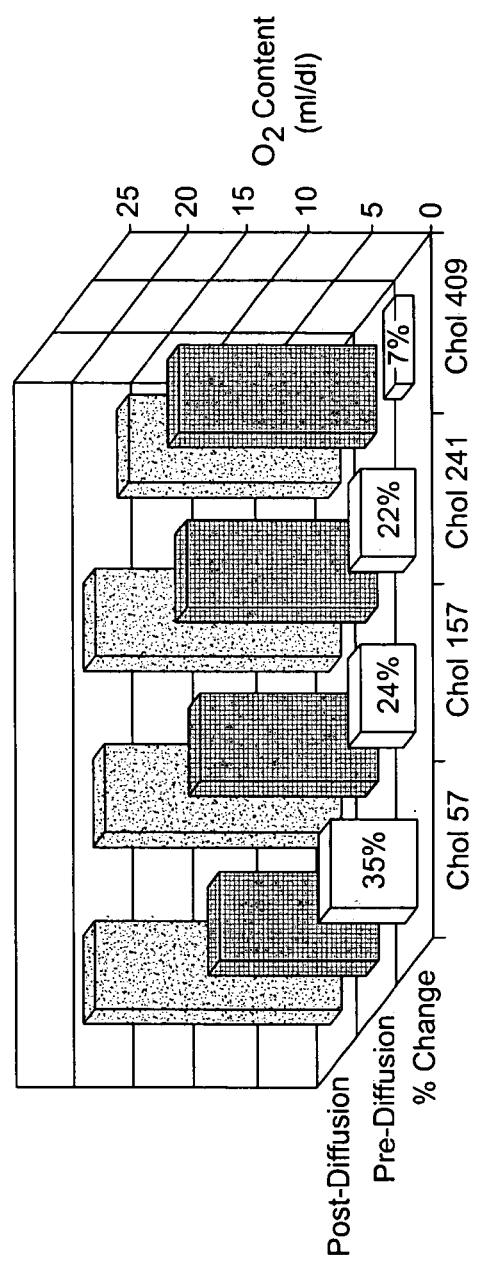
FIG. 17 illustrates that groups of patients with ranges of cholesterol levels can also be grouped by the rate at which oxygen diffuses from their red blood cells

The results of this study are reported in FIG. 17. FIG. 17 illustrates that the 3 plasma cholesterol groups >200 mg/dl all had marked $O_2$ diffusion reductions, compared with the <199 mg/dl group, at 1 min: 82% (p=0.080), 70% (p=0.036), and 100% (p=0.012), respectively; and at 2 min: 32% (p=0.05), 45% (p=0.008), and 66% (p=0.001), respectively. When the hypoxic conditions were maintained over 12 min, the $O_2$ diffusion depravation induced by hypercholesterolemia was cumulative.

Conclusions

This study determined that groups of patients with ranges of cholesterol levels can also be grouped by the rate at which oxygen diffuses from their red blood cells.

Study 4

This study provided an extended analysis of groups of patients with ranges of cholesterol levels and determined short measurement times that revealed different oxygen diffusion rates from red blood cells.

Materials and Methods

This study was an extended analysis involving 93 patents. The patients were grouped into 5 quintiles by plasma cholesterol concentrations: 175 to 199 mg/dl, 200 to 224 mg/dl, 225 to 249 mg/dl, 250 to 274 mg/dl, and 275 to 299 mg/dl.

Results

The 5 cholesterol groups layered out as expected with respect to the percent change in blood $O_2$ diffusion. The greatest percentage change occurred in the lowest cholesterol group; the least percent change in the highest cholesterol group.

Conclusions

Figure 18:
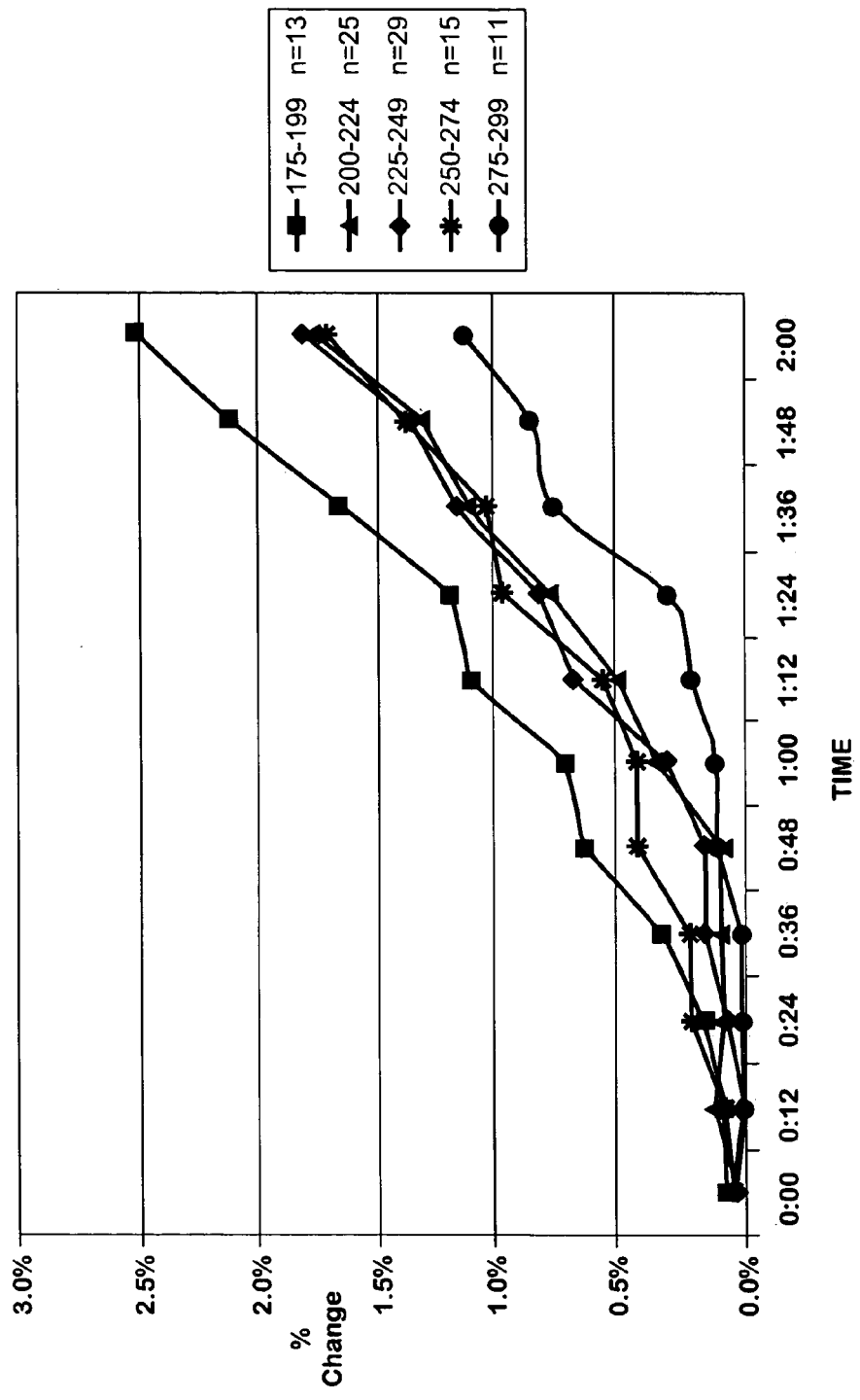
FIG. 18 illustrates timecourses for oxygen release from red blood cells for patients grouped by cholesterol level.

A very clear differentiation between these groups could be seen within the first 2 min of circulation in an apparatus according to the invention, the equivalent of about 2 sec of cardiac circulation (FIG. 18).

Example 3

Correlation of Cholesterol Levels With Red Blood Cell Oxygen Diffusion Measured by Sequential Detection An apparatus according to a preferred embodiment of the present invention was employed to gather data comparing the slopes of the natural log of the plot of $SO_2$ vs. time for different values of serum cholesterol. This device included a set up as illustrated in FIG. 1.

Figure 19:
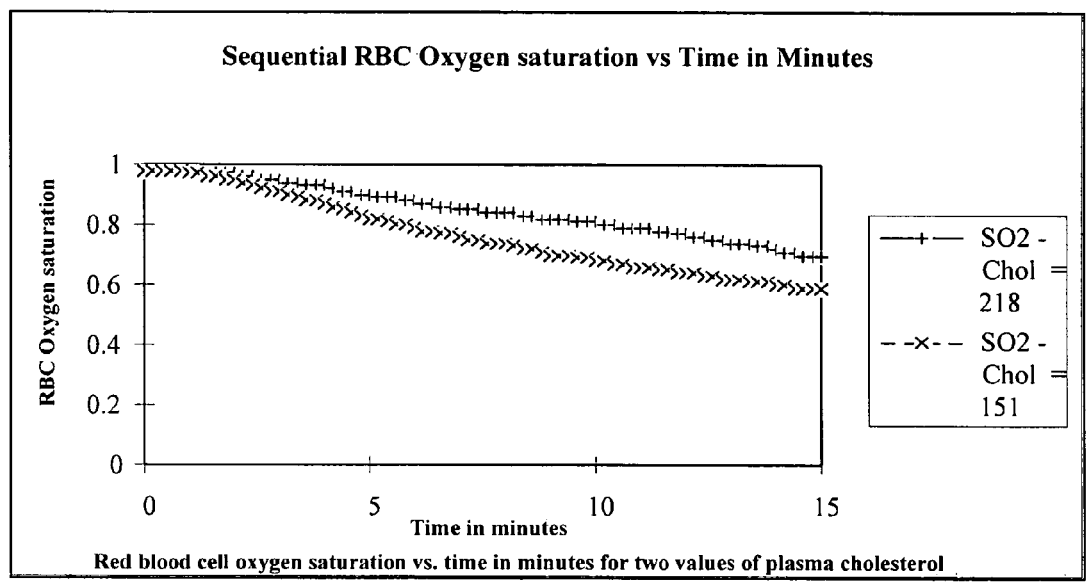
FIG. 19 illustrates a plot of red blood cell oxygen saturation against time in minutes for 2 values of plasma cholesterol; +corresponds to a cholesterol level of 218 mg per dl; x corresponds to a cholesterol level of 151 mg per dl.

Time constants obtained for two different cholesterol concentrations are shown in Table 4 below and in FIG. 19, Ratios of the time constants between high and low cholesterol concentrations, in this case 1.7, is independent of the apparatus, as long as the apparatus remains constant. Thus the apparatus can be calibrated with a set of samples of known plasma concentration of cholesterol and the ratios determined. From the curves, it can be seen that the times for desaturation are long compared to previously published values. The scaling factor of the apparatus (S) can thus quantify the effect that only a small proportion of the total red blood cell sample is subjected to a $pO_2$ at any one time

TABLE 6

Values of exponents,
correlation coefficient and time constants from FIG. 16

|  | Value | Exponent | $R^2$ | time constant (minutes) |
|---|---|---|---|---|
| High Cholesterol | 218 | −0.0224 | 0.99 | 44.6 |
| Low Cholesterol | 151 | −0.0372 | 0.99 | 26.9 |

The invention has been described with reference to various specific and preferred embodiments and techniques. However, it should be understood that many variations and modifications may be made while remaining within the spirit and scope of the invention.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration to. The phrase "adapted and configured" can be used interchangeably with other similar phrases such as arranged and configured, constructed and arranged, adapted, constructed, manufactured and arranged, and the like.

What is claimed is:

1. An apparatus for measuring diffusion of oxygen across a red blood cell membrane, the apparatus comprising:
    an oxygen level detector, a gas exchange system, and a red blood cell transport system;
        the red blood cell transport system being adapted and configured for transporting red blood cells through the gas exchange system and the oxygen level detector;
        the gas exchange system being adapted and configured to exchange gasses with the red blood cell;
        the oxygen level detector being adapted and configured for detecting oxygen levels in a red blood cell or in fluid surrounding a red blood cell; and
    a modular transport system; the modular transport system comprising a sampling apparatus, a pump, a diffusion apparatus, and a transparent optical system;
        the modular transport system being adapted and configured for reversibly coupling to a main body of the apparatus which comprises a gas inlet, a gas outlet, a pump motor, a measuring system, and a control system, wherein the measuring system measures a) an amount of oxygen inside of a red blood cell, b) an amount of oxygen outside of a red blood cell, or c) an amount of oxygen inside and outside of a red blood cell;
        the sampling apparatus being adapted and configured for introducing a fluid containing red blood cells into the red blood cell transport system;
        the pump being adapted and configured for moving a fluid containing red blood cells into and through the red blood cell transport system, and through the diffusion apparatus and the transparent optical system;
        the diffusion apparatus being adapted and configured for providing contact between a gas and a red blood cell; and
        the transparent optical system being adapted and configured for providing a generally transparent pathway for light to access the fluid containing red blood cells.

2. The apparatus of claim 1, wherein the modular transport system and the pump are adapted and configured for coupling the pump to a motor, the motor being housed in the main body of the apparatus and adapted and configured for driving the pump.

3. The apparatus of claim 2, wherein the pump comprises a reciprocating piston pump and the motor comprises one or more cams adapted and configured to drive the reciprocating piston.

4. The apparatus of claim 1, wherein the modular transport system and the diffusion apparatus couple with the main body of the apparatus to cooperatively form an environmental chamber, the environmental chamber being adapted and configured to retain a gas mixture in contact with a membrane of the diffusion apparatus.

5. The apparatus of claim 1, wherein the modular transport system and the transparent optical system couple with the measuring system, the measuring system being housed by the main body of the apparatus and adapted and configured for directing light upon the transparent optical system.

6. The apparatus of claim 1, wherein the modular transport system comprises a cassette.

7. The apparatus of claim 1, wherein the modular transport system houses a first fluid circuit.

8. The apparatus of claim 1, wherein the sampling apparatus comprises a puncture system, which comprises a vented puncture spike.

9. The apparatus of claim 1, wherein the pump comprises a reciprocating piston pump.

10. The apparatus of claim 1, wherein the diffusion apparatus comprises a hydrophobic microporous membrane.

11. The apparatus of claim 10, wherein the hydrophobic microporous membrane comprises a polypropylene membrane.

12. The apparatus of claim 1, wherein the transparent optical system comprises a cuvette.

13. The apparatus of claim 1, wherein the main body defines a portion of an environmental chamber;
the gas exchange system comprising the gas inlet, the gas outlet, a main body portion of the environmental chamber, and the diffusion apparatus, wherein the gas inlet, gas outlet, and the main body portion of the environmental chamber are adapted and configured for coupling with the diffusion apparatus;
the red blood cell transport system comprising the pump and pump motor, the pump motor being adapted and configured for coupling to and driving the pump;
the oxygen level detector comprising the measuring system and the transparent optical system, the measuring system being adapted and configured for directing light upon the transparent optical system.

14. The apparatus of claim 1, wherein the gas exchange system comprises a closed circuit diffusion system; the closed circuit diffusion system comprising a gas permeable tubing and a housing; the gas permeable tubing having a lumen effective for containing red blood cells; the housing being adapted and configured for containing successive samples of gases.

15. The apparatus of claim 1, wherein the red blood cell transport system comprises a pump.

16. The apparatus of claim 1, wherein the oxygen level detector comprises an oxygen electrode.

17. The apparatus of claim 1, wherein the oxygen level detector comprises a spectrophotometric detector.

18. The apparatus of claim 1, wherein the oxygen level detector comprises a fluorometric detector.

19. The apparatus of claim 1, comprising:
a first LED, a second LED, a third LED, a detector, and a reflector;
the first LED emitting at wavelengths comprising about 650 nm, the second and third LEDs emitting at wavelengths comprising about 805 mm;
the detector being arranged and configured for detecting light emitted by the first, second or third LED and reflected by the reflector.

20. A method for determining a patient's susceptibility to a disease or disorder of oxygen release or uptake, the method comprising:
obtaining a blood sample from the patient;
measuring a rate of oxygen diffusion across a membrane of a red blood cell of the blood sample with the apparatus of claim 1; and
correlating the measured rate with the susceptibility at the measured rate of the patient or of a control population to the disease or disorder of oxygen release or uptake, including, correlating the measure rate with the patient's response to a therapeutic agent or protocol.

21. The method of claim 20, wherein correlating further comprises correlating a cholesterol level with one or more of the measured rate or the patient's response to a therapeutic agent or protocol.

22. A method for determining a patient's susceptibility to a disease or disorder of oxygen release or uptake, the method comprising:
obtaining a blood sample from the patient;
measuring a rate of oxygen diffusion across a membrane of a red blood cell of the blood sample with the apparatus of claim 1, the step of measuring including:
exposing the red blood cell to oxygen b at atmospheric gas pressures;
desaturating the oxygenated red blood cell by exposing said red blood cell to a gas environment depleted of oxygen by circulating the blood sample in a closed circuit diffusion chamber, the chamber housing an atmosphere depleted of oxygen; and
monitoring either a blood level of oxygen, a level of oxygen bound to hemoglobin, or both; and
correlating the measured rate with the susceptibility at the measured rate of the patient or of a control population to the disease or disorder of oxygen release or uptake.

23. The method of claim 22
wherein the disease or disorder comprises coronary artery disease; angina pectoris; pulmonary disease; peripheral vascular disease; a disease or disorder of endothelial function; a disease or disorder of the release of transmitters; or a combination thereof.

24. A method for determining a patient's susceptibility to a disease or disorder of oxygen release or uptake, the method comprising:
subjecting the patient to a cardiac stress test;
obtaining a blood sample from the patient;
measuring a rate of oxygen diffusion across a membrane of a red blood cell of the blood sample with the apparatus of claim 1;
correlating the measured rate with the susceptibility at the measured rate of the patient or of a control population to the disease or disorder of oxygen release or uptake;
wherein the disease or disorder comprises heart disease; pulmonary disease; peripheral vascular disease; a disease or disorder of endothelial function; a disease or disorder of the release of transmitters; or a combination thereof.

25. A method for determining a patient's susceptibility to a disease or disorder of oxygen release or uptake, the method comprising:
obtaining a blood sample from the patient;
measuring a rate of oxygen diffusion across a membrane of a red blood cell of the blood sample with the apparatus of claim 1;
correlating the measured rate with the susceptibility at the measured rate of the patient or of a control population to the disease or disorder of oxygen release or uptake;
wherein the disease or disorder comprises heart disease; pulmonary disease; peripheral vascular disease; a disease or disorder of endothelial function; a disease or disorder of the release of transmitters; or a combination thereof;
wherein a cardiac stress test is contraindicated for the patient.

* * * * *

UNITED STATES PATENT AND TRADEMARK OFFICE
CERTIFICATE OF CORRECTION

| | | |
|---|---|---|
| PATENT NO. | : 7,687,272 B1 | Page 1 of 1 |
| APPLICATION NO. | : 09/645236 | |
| DATED | : March 30, 2010 | |
| INVENTOR(S) | : Buchwald et al. | |

It is certified that error appears in the above-identified patent and that said Letters Patent is hereby corrected as shown below:

Title Page 2, (56) References Cited, Other Publications: "Koyama, T. et al., "Diffision Pathway" should read --Koyama, T. et al., "Diffusion Pathway--

Col. 1, lines 13-14: "Jan. 12, 1998 now U.S. Pat. No. 6,037,181 issued on" should read --Jan. 12, 1998, now U.S. Pat. No. 6,037,181, issued on--

Col. 4, line 30: "in wbkh the present" should read --in which the present--

Col. 22, line 65: "The ratio Of" should read --The ratio of--

Signed and Sealed this

Ninth Day of November, 2010

David J. Kappos
*Director of the United States Patent and Trademark Office*